United States Patent
Silkoff et al.

(10) Patent No.: US 11,827,989 B2
(45) Date of Patent: Nov. 28, 2023

(54) SYSTEMS AND METHODS FOR PREVENTING AND TREATING INFECTIONS WITH NITRIC OXIDE

(71) Applicant: Third Pole, Inc., Waltham, MA (US)

(72) Inventors: Philip E. Silkoff, Philadelphia, PA (US); Gregory W. Hall, Belmont, MA (US); Wolfgang Scholz, Beverly, MA (US)

(73) Assignee: Third Pole, Inc., Waltham, MA (US)

( * ) Notice: Subject to any disclaimer, the term of this patent is extended or adjusted under 35 U.S.C. 154(b) by 0 days.

(21) Appl. No.: 17/837,416

(22) Filed: Jun. 10, 2022

(65) Prior Publication Data

US 2022/0298653 A1 Sep. 22, 2022

Related U.S. Application Data

(63) Continuation of application No. 17/352,225, filed on Jun. 18, 2021, now abandoned.
(Continued)

(51) Int. Cl.
*C25B 1/50* (2021.01)
*C01B 21/24* (2006.01)
*C25B 1/01* (2021.01)

(52) U.S. Cl.
CPC ............... *C25B 1/50* (2021.01); *C01B 21/24* (2013.01); *C25B 1/01* (2021.01)

(58) Field of Classification Search
CPC . C25B 1/50; C25B 1/01; C01B 21/24; A61M 16/1005; A61M 16/10;
(Continued)

(56) References Cited

U.S. PATENT DOCUMENTS 709,867 A 9/1902 Bradley et al.
2,485,478 A 10/1949 Cotton
(Continued)

FOREIGN PATENT DOCUMENTS

CA 2413834 6/2004
CN 1099997 3/1995
(Continued)

OTHER PUBLICATIONS

Arjunan Thesis—Plasma Produced Reactive Oxygen and Nitrogen Species in Angiogenesis—May 2011—Krishna Priya Arjunan.
(Continued)

*Primary Examiner* — Xiuyu Tai
(74) *Attorney, Agent, or Firm* — Greenberg Traurig, LLP; David J. Dykeman; Jaime Burke

(57) ABSTRACT

System and methods for providing nitric oxide can include at least one pair of electrodes configured to generate a product gas containing nitric oxide from a flow of a reactant gas, and at least one controller configured to regulate an amount of nitric oxide in the product gas generated by the at least one pair of electrodes using one or more parameters as an input to the controller. One or more sensors are configured to collect information relating to at least one of patient information, the reactant gas, the product gas, and an inspiratory gas into which at least a portion of the product gas flows, the sensors configured to communicate the information to the controller to be used as the one or more parameters. The patient information includes information relating to a methemoglobin (MetHg) measurement collected from a MetHg sensor.

19 Claims, 34 Drawing Sheets

Related U.S. Application Data

(60) Provisional application No. 63/194,145, filed on May 27, 2021, provisional application No. 63/159,981, filed on Mar. 11, 2021, provisional application No. 63/040,982, filed on Jun. 18, 2020.

(58) Field of Classification Search
CPC .......... A61M 16/0093; A61M 16/1065; A61M 16/125; A61M 2205/75; A61M 2016/0039; A61M 16/0683; A61M 2202/0208; A61M 16/209; A61M 16/085; A61M 2205/3331; A61M 16/06; A61M 2205/3368; A61M 2202/0275; A61M 16/0066; A61M 16/0833; A61M 2202/0007; A61M 16/12; A61M 2016/003; A61M 16/1015; A61M 16/208; A61M 2016/1035; A61P 11/00; A61P 9/08; A61P 7/06; A61P 7/08; A61P 43/00; A61P 9/10; A61P 9/00; A61K 33/00; A61K 2300/00; A61K 38/42; A61K 45/06
See application file for complete search history.

(56) References Cited

U.S. PATENT DOCUMENTS

| | | |
|---|---|---|
| 2,485,481 A | 10/1949 | Cotton |
| 2,525,938 A | 10/1950 | Peck |
| 2,684,448 A | 7/1954 | Nilles |
| 3,047,370 A | 7/1962 | Aviges et al. |
| 3,225,309 A | 12/1965 | Phelps |
| 4,287,040 A | 9/1981 | Alamaro |
| 4,500,563 A | 2/1985 | Ellenberger et al. |
| 4,505,795 A | 3/1985 | Alamaro |
| 4,680,694 A | 7/1987 | Huynh et al. |
| 4,695,358 A | 9/1987 | Mizuno et al. |
| 4,705,670 A | 11/1987 | O'Hare |
| 4,816,229 A | 3/1989 | JeRnsen et al. |
| 4,877,589 A | 10/1989 | Conrad |
| 5,285,372 A | 2/1994 | Huynh et al. |
| 5,378,436 A | 1/1995 | Endoh et al. |
| 5,396,882 A | 3/1995 | Zapol |
| 5,413,097 A | 5/1995 | Birenheide et al. |
| 5,471,977 A | 12/1995 | Olsson et al. |
| 5,485,827 A | 1/1996 | Zapol et al. |
| 5,531,218 A | 7/1996 | Krebs |
| 5,546,935 A | 8/1996 | Champeau |
| 5,558,083 A | 9/1996 | Bathe et al. |
| 5,573,733 A | 11/1996 | Salama |
| 5,674,381 A | 10/1997 | Dekker |
| 5,692,495 A | 12/1997 | Sheu |
| 5,732,693 A | 3/1998 | Bathe et al. |
| 5,749,937 A | 5/1998 | Detering et al. |
| 5,752,504 A | 5/1998 | Bathe |
| 5,827,420 A | 10/1998 | Shirazi et al. |
| 5,839,433 A | 11/1998 | Higenbottam |
| 5,845,633 A | 12/1998 | Psaros |
| 6,089,229 A | 7/2000 | Bathe et al. |
| 6,109,260 A | 8/2000 | Bathe |
| 6,125,846 A | 10/2000 | Bathe et al. |
| 6,164,276 A | 12/2000 | Bathe et al. |
| 6,186,140 B1 | 2/2001 | Hoague |
| 6,186,142 B1 | 2/2001 | Schmidt et al. |
| 6,197,091 B1 | 3/2001 | Ji et al. |
| 6,224,653 B1 | 5/2001 | Shvedchikov et al. |
| 6,250,302 B1 | 6/2001 | Rantala |
| 6,290,683 B1 | 9/2001 | Erez et al. |
| 6,296,827 B1 | 10/2001 | Castor et al. |
| 6,365,868 B1 | 4/2002 | Borowy et al. |
| 6,432,077 B1 | 8/2002 | Stenzler |
| 6,532,956 B2 | 3/2003 | Hill |
| 6,536,429 B1 | 3/2003 | Pavlov et al. |
| 6,581,599 B1 | 6/2003 | Stenzler |
| 6,668,828 B1 | 12/2003 | Figley et al. |
| 6,758,214 B2 | 7/2004 | Fine et al. |
| 6,920,876 B2 | 7/2005 | Miller et al. |
| 6,955,171 B1 | 10/2005 | Figley et al. |
| 6,955,790 B2 | 10/2005 | Castor et al. |
| 6,984,256 B2 | 1/2006 | Lamprecht et al. |
| 6,986,351 B2 | 1/2006 | Figley et al. |
| 7,025,869 B2 | 4/2006 | Fine et al. |
| 7,040,313 B2 | 5/2006 | Fine et al. |
| 7,122,018 B2 | 10/2006 | Stenzler et al. |
| 7,220,393 B2 | 5/2007 | Miller et al. |
| 7,255,105 B2 | 8/2007 | Figley et al. |
| 7,299,785 B1 | 11/2007 | Lee |
| 7,312,584 B2 | 12/2007 | Tamita et al. |
| 7,335,181 B2 | 2/2008 | Miller et al. |
| 7,485,324 B2 | 2/2009 | Miller et al. |
| 7,498,000 B2 | 3/2009 | Pekshev et al. |
| 7,516,742 B2 | 4/2009 | Stenzler et al. |
| 7,520,866 B2 | 4/2009 | Stenzler et al. |
| 7,523,752 B2 | 4/2009 | Montgomery et al. |
| 7,531,133 B2 | 5/2009 | Hole et al. |
| 7,560,076 B2 | 7/2009 | Rounbehler et al. |
| 7,589,473 B2 | 9/2009 | Suslov |
| 7,597,731 B2 | 10/2009 | Palmerton et al. |
| 7,618,594 B2 | 11/2009 | Rounbehler et al. |
| 7,744,812 B2 | 6/2010 | Witherspoon et al. |
| 7,861,516 B2 | 1/2011 | Allanson et al. |
| 7,861,717 B1 | 1/2011 | Krebs |
| 7,914,743 B2 | 3/2011 | Fine et al. |
| 7,947,227 B2 | 5/2011 | Fine et al. |
| 7,955,294 B2 | 6/2011 | Stenzler et al. |
| 8,030,849 B2 | 10/2011 | Suslov |
| 8,043,252 B2 | 10/2011 | Miller et al. |
| 8,057,742 B2 | 11/2011 | Rounbehler et al. |
| 8,066,904 B2 | 11/2011 | Fine et al. |
| 8,079,998 B2 | 12/2011 | Hole et al. |
| 8,083,997 B2 | 12/2011 | Rounbehler et al. |
| 8,091,549 B2 | 1/2012 | Montgomery et al. |
| 8,151,791 B2 | 4/2012 | Arlow et al. |
| 8,173,072 B2 | 5/2012 | Fine et al. |
| 8,187,544 B2 | 5/2012 | Fine et al. |
| 8,211,368 B2 | 7/2012 | Fine et al. |
| 8,221,800 B2 | 7/2012 | Fine et al. |
| 8,226,916 B2 | 7/2012 | Rounbehler et al. |
| 8,246,725 B2 | 8/2012 | Rounbehler et al. |
| 8,267,884 B1 | 9/2012 | Hicks |
| 8,268,252 B2 | 9/2012 | Fuller et al. |
| 8,277,399 B2 | 10/2012 | Hamilton et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,328,998 B2 | 12/2012 | Wada et al. |
| 8,344,627 B1 | 1/2013 | Hooke et al. |
| 8,371,296 B2 | 2/2013 | Fine et al. |
| 8,377,462 B2 | 2/2013 | DesNoyer et al. |
| 8,397,721 B2 | 3/2013 | Montgomery et al. |
| D679,366 S | 4/2013 | Fuller |
| 8,408,206 B2 | 4/2013 | Montgomery et al. |
| 8,431,163 B2 | 4/2013 | Baldassarre et al. |
| D688,352 S | 8/2013 | Montgomery et al. |
| 8,518,457 B2 | 8/2013 | Miller et al. |
| 8,573,209 B2 | 11/2013 | Bathe et al. |
| 8,573,210 B2 | 11/2013 | Bathe et al. |
| 8,574,531 B2 | 11/2013 | Miller et al. |
| 8,580,109 B2 | 11/2013 | Kruckenberg et al. |
| 8,607,785 B2 | 12/2013 | Fine et al. |
| 8,607,792 B2 | 12/2013 | Montgomery et al. |
| 8,609,026 B2 | 12/2013 | Fine et al. |
| 8,609,028 B2 | 12/2013 | Rounbehler et al. |
| 8,613,958 B2 | 12/2013 | Fine |
| 8,616,204 B2 | 12/2013 | Montgomery et al. |
| 8,646,445 B2 | 2/2014 | Fine et al. |
| D701,963 S | 4/2014 | Abarbanel et al. |
| 8,685,467 B2 | 4/2014 | Miller et al. |
| 8,701,657 B2 | 4/2014 | Fine et al. |
| 8,715,577 B2 | 5/2014 | Fine et al. |
| 8,717,733 B2 | 5/2014 | Gefter et al. |
| 8,720,440 B2 | 5/2014 | Montgomery et al. |
| 8,741,222 B2 | 6/2014 | Fine et al. |
| 8,757,148 B2 | 6/2014 | Montgomery et al. |
| 8,770,199 B2 | 7/2014 | Flanagan et al. |

(56) References Cited

U.S. PATENT DOCUMENTS

| | | |
|---|---|---|
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |
| 8,795,741 B2 | 8/2014 | Baldassarre |
| 8,808,655 B2 | 8/2014 | Solovyov et al. |
| 8,821,801 B2 | 9/2014 | Rounbehler et al. |
| 8,821,828 B2 | 9/2014 | Hilbig et al. |
| 8,846,112 B2 | 9/2014 | Baldassarre |
| 8,887,720 B2 | 11/2014 | Fine et al. |
| 8,893,717 B2 | 11/2014 | Montgomery et al. |
| 8,944,049 B2 | 2/2015 | Fine et al. |
| 9,035,045 B2 | 5/2015 | Chu et al. |
| 9,067,788 B1 | 6/2015 | Spielman et al. |
| 9,095,534 B2 | 8/2015 | Stenzler et al. |
| 9,108,016 B2 | 8/2015 | Acker et al. |
| 9,180,217 B2 | 11/2015 | Arnold et al. |
| 9,192,718 B2 | 11/2015 | Fine |
| 9,260,399 B2 | 2/2016 | Ruan et al. |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,351,994 B2 | 5/2016 | Montgomery et al. |
| 9,408,994 B2 | 5/2016 | Fine et al. |
| 9,408,993 B2 | 8/2016 | Bathe et al. |
| 9,522,249 B2 | 12/2016 | Rounbehler et al. |
| 9,550,039 B2 | 1/2017 | Flanagan et al. |
| 9,550,040 B2 | 1/2017 | Acker et al. |
| 9,562,113 B2 | 2/2017 | Ruan et al. |
| 9,573,110 B2 | 2/2017 | Montgomery et al. |
| 9,604,028 B2 | 3/2017 | Fine et al. |
| 9,701,538 B2 | 7/2017 | Fine et al. |
| 9,713,244 B2 | 7/2017 | Tabata et al. |
| 9,770,570 B2 | 9/2017 | Schnictman et al. |
| 9,795,756 B2 | 10/2017 | Flanagan et al. |
| 9,895,199 B2 | 2/2018 | Montgomery et al. |
| 9,896,337 B2 | 2/2018 | Montgomery et al. |
| 9,956,373 B2 | 5/2018 | Rounbehler et al. |
| 9,982,354 B2 | 5/2018 | Kim |
| 10,081,544 B2 | 9/2018 | Fine et al. |
| 10,086,352 B2 | 10/2018 | Fine et al. |
| 10,099,029 B2 | 10/2018 | Montgomery et al. |
| 10,124,142 B2 | 11/2018 | Rounbehler et al. |
| 10,179,222 B2 | 1/2019 | Fine et al. |
| 10,188,822 B2 | 1/2019 | Flanagan et al. |
| 10,213,572 B2 | 2/2019 | Gellman et al. |
| 10,226,592 B2 | 3/2019 | Acker et al. |
| 10,232,138 B2 | 3/2019 | Acker et al. |
| 10,239,038 B2 | 3/2019 | Zapol et al. |
| 10,279,139 B2 | 5/2019 | Zapol et al. |
| 10,286,176 B2 | 5/2019 | Zapol et al. |
| 10,293,133 B2 | 5/2019 | Zapol et al. |
| 10,328,228 B2 | 6/2019 | Zapol et al. |
| 10,398,820 B2 | 9/2019 | Potenziano et al. |
| 10,426,913 B2 | 10/2019 | Tolmie et al. |
| 10,434,276 B2 | 10/2019 | Zapol et al. |
| 10,532,176 B2 | 1/2020 | Zapol et al. |
| 10,548,920 B2 | 2/2020 | Montgomery et al. |
| 10,556,082 B2 | 2/2020 | Flanagan et al. |
| 10,556,086 B2 | 2/2020 | Goldstein et al. |
| 10,576,239 B2 | 3/2020 | Zapol et al. |
| 10,646,682 B2 | 5/2020 | Zapol et al. |
| 10,682,486 B1 | 6/2020 | Moon et al. |
| 10,695,523 B2 | 6/2020 | Zapol et al. |
| 10,737,051 B2 | 8/2020 | Gellman et al. |
| 10,750,606 B1 | 8/2020 | Liu et al. |
| 10,758,703 B2 | 9/2020 | Kohlmann et al. |
| 10,773,046 B2 | 9/2020 | Schnitman et al. |
| 10,773,047 B2 | 9/2020 | Zapol et al. |
| 10,780,241 B2 | 9/2020 | Fine et al. |
| 10,814,092 B2 | 10/2020 | Rounbehler et al. |
| 10,946,163 B2 | 3/2021 | Gillerman et al. |
| 11,007,503 B2 | 5/2021 | Zapol et al. |
| 11,033,705 B2 | 6/2021 | Zapol et al. |
| 11,045,620 B2 | 6/2021 | Hall et al. |
| 11,376,390 B2 | 7/2022 | Gillerman et al. |
| 11,478,601 B2 | 10/2022 | Hall et al. |
| 11,479,464 B2 | 10/2022 | Hall et al. |
| 11,524,134 B2 | 12/2022 | Zapol et al. |
| 11,554,240 B2 | 1/2023 | Hall et al. |
| 11,660,416 B2 | 5/2023 | McAuley et al. |
| 11,691,879 B2 | 7/2023 | Kondiboyina et al. |
| 2001/0031230 A1 | 10/2001 | Castor et al. |
| 2001/0035186 A1 | 11/2001 | Hill |
| 2002/0111748 A1 | 8/2002 | Kobayashi et al. |
| 2002/0185126 A1 | 12/2002 | Krebs |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsay |
| 2004/0050387 A1 | 3/2004 | Younes |
| 2004/0149282 A1 | 8/2004 | Hickle |
| 2004/0168686 A1 | 9/2004 | Krebs |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0274381 A1 | 12/2005 | Deane et al. |
| 2005/0281465 A1 | 12/2005 | Marquart et al. |
| 2006/0025700 A1 | 2/2006 | Fallik |
| 2006/0090759 A1 | 5/2006 | Howes et al. |
| 2006/0172018 A1 | 8/2006 | Fine et al. |
| 2006/0173396 A1 | 8/2006 | Hatamian et al. |
| 2006/0207594 A1 | 9/2006 | Stenzler et al. |
| 2006/0276844 A1 | 12/2006 | Alon et al. |
| 2007/0051712 A1 | 3/2007 | Kooken et al. |
| 2007/0113851 A1 | 5/2007 | Delisle et al. |
| 2007/0151561 A1 | 7/2007 | Laurila |
| 2007/0181126 A1 | 8/2007 | Tolmie et al. |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |
| 2008/0176335 A1 | 7/2008 | Alberti et al. |
| 2008/0202509 A1 | 8/2008 | Dillon et al. |
| 2010/0030091 A1 | 2/2010 | Fine |
| 2010/0043789 A1 | 2/2010 | Fine et al. |
| 2010/0051025 A1* | 3/2010 | Zapol ............... A61P 11/00 424/93.73 |
| 2010/0076325 A1 | 3/2010 | Cho et al. |
| 2010/0089392 A1 | 4/2010 | Fine et al. |
| 2010/0189808 A1 | 7/2010 | Gupta et al. |
| 2010/0275911 A1 | 11/2010 | Arlow et al. |
| 2010/0330193 A1 | 12/2010 | Baldassarre et al. |
| 2011/0140607 A1 | 6/2011 | Moore et al. |
| 2011/0240019 A1 | 10/2011 | Fine et al. |
| 2012/0093948 A1 | 4/2012 | Fine et al. |
| 2012/0279500 A1 | 11/2012 | Singvogel et al. |
| 2012/0285449 A1 | 11/2012 | Fine et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2013/0239963 A1 | 9/2013 | Goldstein et al. |
| 2013/0309328 A1 | 11/2013 | Watts et al. |
| 2014/0020685 A1 | 1/2014 | Szabo |
| 2014/0031668 A1 | 1/2014 | Mobasser et al. |
| 2014/0127081 A1 | 5/2014 | Fine et al. |
| 2014/0127330 A1 | 5/2014 | Fine et al. |
| 2014/0144436 A1 | 5/2014 | Fine et al. |
| 2014/0144444 A1 | 5/2014 | Fine et al. |
| 2014/0158121 A1 | 6/2014 | Flanagan et al. |
| 2014/0166009 A1 | 6/2014 | Flanagan et al. |
| 2014/0216452 A1 | 8/2014 | Miller et al. |
| 2014/0251787 A1 | 9/2014 | Montgomery et al. |
| 2014/0363525 A1 | 12/2014 | Montgomery et al. |
| 2014/0377378 A1 | 12/2014 | Baldassarre |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0075522 A1 | 3/2015 | Acker et al. |
| 2015/0090261 A1 | 4/2015 | Crosbie |
| 2015/0101604 A1 | 4/2015 | Crosbie |
| 2015/0174158 A1 | 6/2015 | Av-Gay et al. |

(56) References Cited

U.S. PATENT DOCUMENTS

| | | |
|---|---|---|
| 2015/0272988 A1 | 10/2015 | Av-Gay et al. |
| 2015/0328430 A1 | 11/2015 | Miller et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0045685 A1 | 2/2016 | Hyde et al. |
| 2016/0106946 A1 | 4/2016 | Gellman et al. |
| 2016/0106949 A1 | 4/2016 | Kohlmann et al. |
| 2016/0121071 A1 | 5/2016 | Moon et al. |
| 2016/0151598 A1 | 6/2016 | Fine |
| 2016/0183841 A1 | 6/2016 | Duindam et al. |
| 2016/0191887 A1 | 6/2016 | Casas |
| 2016/0193336 A1 | 7/2016 | Nelson et al. |
| 2016/0228670 A1 | 8/2016 | Av-Gay et al. |
| 2016/0243328 A1 | 8/2016 | Tolmie et al. |
| 2016/0271169 A1 | 9/2016 | Potenziano et al. |
| 2016/0279165 A1 | 9/2016 | Av-Gay et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0112871 A1 | 4/2017 | Nelson et al. |
| 2017/0128694 A1 | 5/2017 | Acker et al. |
| 2017/0143758 A1 | 5/2017 | Greenberg et al. |
| 2017/0165294 A1 | 6/2017 | Dasse et al. |
| 2017/0182088 A1 | 6/2017 | Dasse et al. |
| 2017/0232166 A1 | 8/2017 | Potenziano et al. |
| 2017/0239289 A1 | 8/2017 | Av-Gay et al. |
| 2017/0259025 A1 | 9/2017 | Fine et al. |
| 2017/0296463 A1 | 10/2017 | Minton et al. |
| 2017/0348503 A1 | 12/2017 | Westermark |
| 2018/0049622 A1 | 2/2018 | Ryan et al. |
| 2018/0104432 A1 | 4/2018 | Flanagan et al. |
| 2018/0125883 A1 | 5/2018 | Av-Gay et al. |
| 2018/0126111 A1 | 5/2018 | Moon et al. |
| 2018/0133246 A1 | 5/2018 | Av-Gay et al. |
| 2018/0169370 A1 | 6/2018 | Montgomery et al. |
| 2018/0228836 A1 | 8/2018 | Nelson et al. |
| 2018/0243527 A1 | 8/2018 | Zapol et al. |
| 2018/0243528 A1 | 8/2018 | Zapol et al. |
| 2018/0264032 A1 | 9/2018 | Jaffri et al. |
| 2018/0280920 A1 | 10/2018 | Zapol et al. |
| 2018/0296790 A1 | 10/2018 | Zapol et al. |
| 2018/0304038 A1 | 10/2018 | Jafri et al. |
| 2018/0311460 A1 | 11/2018 | Rounbehler et al. |
| 2018/0328842 A1 | 11/2018 | Kjaer |
| 2019/0038864 A1 | 2/2019 | Montgomery et al. |
| 2019/0092639 A1 | 3/2019 | Fine et al. |
| 2019/0127223 A1 | 5/2019 | Montgomery et al. |
| 2019/0135633 A1 | 5/2019 | Montgomery et al. |
| 2019/0143068 A1 | 5/2019 | Rounbehler et al. |
| 2019/0184116 A1 | 6/2019 | Acker et al. |
| 2019/0209993 A1 | 7/2019 | Fine et al. |
| 2019/0217042 A1 | 7/2019 | Zapol et al. |
| 2019/0217043 A1 | 7/2019 | Fine et al. |
| 2019/0233288 A1 | 8/2019 | Montgomery et al. |
| 2019/0233289 A1 | 8/2019 | Montgomery et al. |
| 2019/0276313 A1 | 9/2019 | Montgomery et al. |
| 2019/0314596 A1 | 10/2019 | Zapol et al. |
| 2019/0374739 A1 | 12/2019 | Tolmie et al. |
| 2020/0030553 A1 | 1/2020 | Keip et al. |
| 2020/0094011 A1 | 3/2020 | Zapol et al. |
| 2020/0139071 A1 | 5/2020 | Fine et al. |
| 2020/0139072 A1 | 5/2020 | Zapol et al. |
| 2020/0139073 A1 | 5/2020 | Tector et al. |
| 2020/0163989 A1 | 5/2020 | Montgomery et al. |
| 2020/0171259 A1 | 6/2020 | Flanagan et al. |
| 2020/0171264 A1 | 6/2020 | Goldstein et al. |
| 2020/0180958 A1 | 6/2020 | Fine et al. |
| 2020/0188319 A1 | 6/2020 | Quinn et al. |
| 2020/0254199 A1 | 8/2020 | Bassin |
| 2020/0282375 A1 | 9/2020 | Fine et al. |
| 2020/0360647 A1 | 11/2020 | Quinn et al. |
| 2020/0360649 A1 | 11/2020 | Hall et al. |
| 2020/0360690 A1 | 11/2020 | Evans et al. |
| 2020/0361772 A1 | 11/2020 | Hall et al. |
| 2020/0361773 A1 | 11/2020 | Gillerman et al. |
| 2020/0390994 A1 | 12/2020 | Gillerman et al. |
| 2021/0214222 A1 | 7/2021 | Kondiboyia et al. |
| 2021/0220586 A1 | 7/2021 | Shah et al. |
| 2021/0268221 A1 | 9/2021 | Gillerman et al. |
| 2021/0330957 A1 | 10/2021 | Potenziano et al. |
| 2021/0353898 A1 | 11/2021 | Hall et al. |
| 2021/0386954 A1 | 12/2021 | Tamiya et al. |
| 2021/0395905 A1 | 12/2021 | Silkoff et al. |
| 2022/0047837 A1 | 2/2022 | Zapol et al. |
| 2022/0080147 A1 | 3/2022 | Shah et al. |
| 2022/0096535 A1 | 3/2022 | Shah et al. |
| 2022/0135406 A1 | 5/2022 | Apollonio et al. |
| 2022/0162070 A1 | 5/2022 | Silkoff et al. |
| 2022/0211967 A1 | 7/2022 | Hall et al. |
| 2022/0296845 A1 | 9/2022 | Jackson et al. |
| 2022/0339391 A1 | 10/2022 | Gillerman et al. |
| 2023/0001119 A1 | 1/2023 | Richardson et al. |
| 2023/0053201 A1 | 2/2023 | Miles et al. |
| 2023/0098706 A1 | 3/2023 | Miles et al. |
| 2023/0112963 A1 | 4/2023 | Yuen et al. |
| 2023/0149556 A1 | 5/2023 | Hall et al. |
| 2023/0158064 A1 | 5/2023 | Shah |
| 2023/0158260 A1 | 5/2023 | Shah et al. |
| 2023/0158261 A1 | 5/2023 | Trias et al. |
| 2023/0201497 A1 | 6/2023 | Dekker |
| 2023/0263986 A1 | 8/2023 | Hall et al. |

FOREIGN PATENT DOCUMENTS

| | | |
|---|---|---|
| CN | 1730115 | 2/2006 |
| CN | 201037113 | 3/2008 |
| CN | 100404083 | 7/2008 |
| CN | 101036482 | 12/2010 |
| CN | 110872714 | 3/2020 |
| DE | 101 51 270 | 10/2006 |
| EP | 621051 | 10/1994 |
| EP | 0763500 | 3/1997 |
| EP | 0878208 A2 | 11/1998 |
| EP | 1036758 | 9/2000 |
| EP | 2151554 | 2/2010 |
| EP | 1854494 | 6/2012 |
| EP | 2565157 | 10/2017 |
| EP | 3372267 | 12/2018 |
| JP | H04132560 | 5/1992 |
| JP | 2000102616 | 4/2000 |
| JP | 2004065636 | 3/2004 |
| JP | 2006273677 | 10/2006 |
| KR | 100841741 B1 | 6/2008 |
| KR | 20100087977 | 8/2010 |
| RU | 2199167 | 2/2003 |
| WO | WO199507610 | 3/1995 |
| WO | WO2004032719 | 4/2004 |
| WO | WO2005094138 | 10/2005 |
| WO | WO2005110441 | 11/2005 |
| WO | WO2008/019102 | 2/2008 |
| WO | WO2008/112143 | 9/2008 |
| WO | 2008116991 A2 | 10/2008 |
| WO | WO2009018837 | 2/2009 |
| WO | WO2010021944 | 2/2010 |
| WO | WO2011/002606 | 1/2011 |
| WO | WO2012014805 | 2/2012 |
| WO | WO2012/034089 | 3/2012 |
| WO | WO2012/094008 | 7/2012 |
| WO | WO2012/155213 | 11/2012 |
| WO | WO2013/052548 | 4/2013 |
| WO | WO2013/070712 | 5/2013 |
| WO | WO2013/181179 | 12/2013 |
| WO | WO2014/085719 | 6/2014 |
| WO | WO2014/143842 | 9/2014 |
| WO | WO2014/144151 | 9/2014 |
| WO | WO2015/049783 | 4/2015 |
| WO | WO2015/066278 | 5/2015 |
| WO | WO2015/127085 | 8/2015 |
| WO | WO2016/064863 | 4/2016 |

(56) References Cited

FOREIGN PATENT DOCUMENTS

| | | |
|---|---|---|
| WO | WO2018/157172 | 8/2018 |
| WO | WO2018/157175 | 8/2018 |
| WO | WO2019/046413 | 3/2019 |
| WO | WO2019/046415 | 3/2019 |
| WO | WO2019/133776 | 7/2019 |
| WO | WO2019/133777 | 7/2019 |
| WO | WO2019/222640 | 11/2019 |
| WO | WO2020/033768 | 2/2020 |
| WO | 2020115473 A1 | 6/2020 |
| WO | WO2020/142658 | 7/2020 |
| WO | WO2020/148155 | 7/2020 |
| WO | WO2020/150195 | 7/2020 |
| WO | WO2020/232414 | 11/2020 |
| WO | WO2020/232419 | 11/2020 |
| WO | WO2021/087382 | 5/2021 |
| WO | WO2021/142472 | 7/2021 |
| WO | 2021154833 A1 | 8/2021 |
| WO | 2021245667 A1 | 12/2021 |
| WO | WO2021/258025 | 12/2021 |
| WO | 2022123567 A1 | 6/2022 |
| WO | 2022123574 A1 | 6/2022 |
| WO | 2022123580 A1 | 6/2022 |
| WO | 2022192757 A1 | 9/2022 |
| WO | 2023018992 A1 | 2/2023 |
| WO | 2023049873 A1 | 3/2023 |
| WO | 2023092103 A1 | 5/2023 |

OTHER PUBLICATIONS

Arora et al., Nitric Oxide Regulation of Bacterial Biofilms, Biochemistry, vol. 54, pp. 3717-3728, May 21, 2015.

Barraud et al., Involvement of Nitric Oxide n Biofilm Dispersal of Pseudomonas Aeruginosa, Journal of Bacteriology, vol. 188, No. 21, pp. 7344-7353, Nov. 2006.

Bellerophon, "Dose Escalation Study to Assess the Safety and Efficacy of Pulsed iNO in Subjects With Pulmonary Fibrosis", Aug. 30, 2017, https://clinicaltrials.gov/ct2/show/NCT03267108.

Bentur et al., Pilot Study to Test Inhaled Nitric Oxide in Cystic Fibrosis Patients with Refactory *Mycobacterium abscessus* Lung Infection, Journal of Cystic Fibrosis, vol. 19, pp. 225-231, May 23, 2019.

Birkeland, K., "On the Oxidation of Atmospheric Nitrogen in Electric Arc", A Paper read before the Faraday Society on Monday, Jul. 2, 1906, Published on Jan. 1, 1906.

Bogdonovski et al., Anti-Mycobacterial Activity of High-Dose Nitric Oxide Against *Mycobacterium abscessus* In Vitro, National Institutes of Health Poster, Jul. 8, 2018.

Charles, et al., "SiO2 Deposition from Oxygen/Silane Pulsed Helicon Diffusion Plasmas" Applied Physics Letters, vol. 67, No. 1, pp. 40-42, Jul. 3, 1995.

Deppisch et al., Gaseous Nitric Oxide to Treat Antibiotic Resistant Bacterial and Fungal Lung Infections in Patients with Cystic Fibrosis: A Phase I Clinical Study, Infection, vol. 44, pp. 513-520, Feb. 9, 2016.

Dobrynin et al. "Direct and Controllable Nitric Oxide into Biological Media and Living Cells by a Pin-to-Hole Spark Discharge (PHD) Plasma" Journal of Physics D: Applied Physics, vol. 44, pp. 1-10, Jan. 28, 2011.

Donohoe et al., "Production of O3, NO, and N2O in a Pulsed Discharge at 1 Atm", Ind. Eng. Chem., Fundam., vol. 16, No. 2, pp. 208-215, May 1977.

Encyclopaedia Britannica, "Soda Lime" published Nov. 12, 2018, https://www.britannica.com/science/soda-lime.

Feigerle, C., et al., "Multiphoton Ionization of Vibrationally Hot Nitric Oxide Produced in a Pulsed Supersonic Glow Discharge", Journal of Chemical Physics, vol. 90, Issue 6, pp. 2900-2908, Mar. 15, 1989.

Fowler, "Exercise Intolerance in Pulmonary Arterial Hypertension", Pulmonary Medicine, vol. 2012, Article ID 39204, 11 pages, (2012).

Habib, Bassam Hanna, "A Simple Model of Spark Gap Discharge Phase", Eng. & Tech. Journal, vol. 31, Part (A), No. 9, pp. 1692-1704, 2013.

Hanning et al., "Pulse Oximetry: A Practical Review", British Medical Journal, vol. 311, pp. 367-370, Aug. 5, 1995.

Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages (Includes English Language Translation of Title Page and Abstract).

Higenbottam et al., "The Direct and Indirect Action of Inhaled Agents on the Lung and Its Circulation: Lessons from Clinical Science," Environmental Health Perspectives, vol. 109, Supplement 4, pp. 559-562, Aug. 2001.

Howlin et al., Low-Dose Nitric Oxide as Targeted Anti-Biolfim Adjunctive Therapy to Treat Chronic Pseudomonas Aeruoginosa Infection in Cystic Fibrosis, Molecular Therapy, vol. 25, No. 9, pp. 2104-2116, Sep. 2017.

Hu, Hui et al., "Study on Production of Nitric Monoxide for Respiratory Distress by Pulsed Discharge", Proceedings of the CSEE, vol. 23, No. 2, Jan. 2005.

Hu, Hui et al., "Study on Pulse Arc Discharge Conditions on Production of Nitric Oxide for Medical Application", High Voltage Apparatus, Issue 3, Mar. 2005.

Hu et al., "Study on Production of Inhaled Nitric Oxide for Medical Applications by Pulsed Discharge", IEEE Transactions on Plasma Science, vol. 35, No. 3, pp. 619-625, Jun. 2007.

Hu, Hui et al., "The Effect of Flow Distribution on the Concentration of NO Produced by Pulsed Arc Discharge", Plasma Science and Technology, vol. 9, No. 6, pp. 766-769, Dec. 2007.

Hu, Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 128 pages (Includes English Language Translation of Title Page and Abstract).

Intersurgical Complete Respiratory Systems, Carbon Dioxide Absorbents Catalogue, www.intersurgical.com/distributors, Issue 5, Oct. 17, 2021.

Johns Hopkins University—"American Chemical Journal vol. XXXV"—No. 4, Reports Chapter, pp. 358-368, Apr. 1906.

Keshav, Saurabh. "Using Plasmas for High-speed Flow Control and Combustion Control" Diss. The Ohio State University, 2008.

Kornev, J., et al., "Generation of Active Oxidant Species by Pulsed Dielectric Barrier Discharge in Water-Air Mixtures", Ozone: Science & Engineering, vol. 28, Issue 4, pp. 207-215, Jul. 2006.

Kuo, Spencer P. "Air Plasma for Medical Applications" J. Biomedical Science and Engineering, vol. 5, pp. 481-495.

Li, Z. et al., "Development of Miniature Pulsed Power Generator," 2005 IEEE Pulsed Power Conference Monterey, CA, pp. 1053-1056, Jul. 2005.

Li et al., Production of Medically Useful Nitric Monoxide Using AC Arc Discharge, Nitric Oxide, vol. 73, pp. 89-95, Feb. 28, 2018.

Lorente L., "Respiratory Filters and Ventilator-Associated Pneumonia: Composition, Efficacy Tests and Advantages and Disadvantages", Humidification in the Intensive Care Unit, pp. 171-177, Springer, Berlin, Heidelberg 2012.

Matsuo, K. et al., "Nitric Oxide Generated by Atmospheric Pressure Air Microplasma," 2009 IEEE Pulsed Power Conference, Washington, DC, Jun. 28-Jul. 2, 2009, pp. 999-1003, Jan. 19, 2010.

McMullin et al., The Antimicrobial Effect of Nitric Oxide on the Bacteria That Cause Nosocomial Pneumonia in Mechanically Ventilated Patients in the Intensive Care Unit, Respiratory Care, vol. 50, No. 11, pp. 1451-1456, Nov. 2005.

Miller et al., Gaseous Nitric Oxide Bactericidal Activity Retained During Intermittent High-Dose Short Duration Exposure, Nitric Oxide, vol. 20, Issue 1, pp. 16-23, Feb. 2009.

Miller et al., Inhaled Nitric Oxide Decreases the Bacterial Load in a Rat Model of Pseudomonas Aeruginosa Pneumonia, Journal of Cystic Fibrosis, vol. 12, pp. 817-820, Mar. 6, 2013.

Miller et al., Nitric Oxide is a Potential Antimicrobial Against Slow and Fast Growing Mycobacteria, Online Abstracts Issue, American Journal Respiratory Care Medicine, vol. 193, A7498, May 18, 2016.

(56) References Cited

OTHER PUBLICATIONS

Miller et al., A Phase I Clinical Study of Inhaled Nitric Oxide in Healthy Adults, Journal of Cystic Fibrosis, vol. 11, pp. 324-331, Apr. 18, 2012.
Mok et al. "Application of Positive Pulsed Corona Discharge to Removal of SO2 and NOx," Proceedings, ICESP VII, Sep. 20-25, 1998, Kyongiu, Korea.
Namihira et al., Production of Nitric Oxide Using Pulsed Discharges for a Medical Application, IEEE Transactions on Plasma Science, vol. 28, No. 1, pp. 109-114, Feb. 2000.
Namihara et al., "Production of NO Using Pulsed Arc Discharges and Its Medical Applications", Journal of Plasma and Fusion Research, vol. 79, No. 1 pp. 35-38, Jun. 25, 2002.
Namihira et al., "Production of Nitric Monoxide in Dry Air Using Pulsed Discharge," Digest of Technical Papers. 12th IEEE International Pulsed Power Conference. (Cat. No. 99CH36358), Monterey, CA, pp. 1313-1316 vol. 2, Aug. 6, 2002.
Namihira et al., Production of Nitric Oxide Using a Pulsed Arc Discharge, IEEE Transactions on Plasma Science, vol. 30, No. 5, pp. 1993-1998, Oct. 2002.
Namihira et al., "Temperature and Nitric Oxide Generation in a Pulsed Arc Discharge Plasma" Plasma Science and Technology, vol. 9, No. 6, pp. 747-751, Dec. 2007.
Navarro-Gonzalez et al., "The Physical Mechanism of Nitric Oxide Formation in Simulated Lightning" Geophysical Research Letters, vol. 28, No. 20, pp. 3867-3870, Oct. 15, 2001.
Olivier et al., Treatment of Refractory *Mycobacterium abscessus* Lung Infection with Inhaled Intermittent Nitric Oxide, Poster, Jul. 8, 2018.
Overzet, et al. "Why and How to Pulse a Plasma"—slide show presentation, Oct. 1997.
Patil et al., Plasma Assisted Nitrogen Oxide Production from Air, AiChE Journal, vol. 64, Issue 2, Aug. 14, 2017.
Pawlat et al., Evaluation of Oxidative Species in Gaseous, Plasma Chemistry and Plasma Processing, vol. 39, pp. 627-642, Mar. 28, 2019.
Pontiga, F., et al., "Nitrogen Oxides Generation Induced by Negative Corona Discharge in N2+02 Mixtures," 2006 IEEE Conference on Electrical Insulation and Dielectric Phenomena, Kansas City, MO, pp. 264-267, Oct. 2006.
Sakai, et al., "A Compact Nitric Oxide Supply for Medical Application," 2007 16th IEEE International Pulsed Power Conference, Albuquerque, NM, 752-755, Oct. 14, 2008.
Sakai et al., "Nitric Oxide Generator Based on Pulsed Arc Discharge"Acta Physica Polonica A, vol. 115, No. 6, pp. 1104-1106, Jun. 2009.
Schilz, "Treatment of Pulmonary Hypertension Related to Disorders of Hypoxia" Advances in Pulmonary Hypertension, vol. 4, No. 2, pp. 14-22, May 2005.
Takaki, et al., "Resistance of Pulsed Arc Discharge in Air and SF/sub 6", Pulse Power Plasma Science, vol. 2, pp. 1758-1761, Jun. 2001.
Tal et al., Nitric Oxide Inhalations in Bronchiolitis: A Pilot, Randomized, Double-Blinded, Controlled Trial, Pediatric Pulmonology, vol. 53, Issue 1, pp. 95-102, Jan. 2018.
Tsukahara et al., "Gas-Phase Oxidation of Nitric Oxide: Chemical Kinetics and Rate Constant," Nitric Oxide: Biology and Chemistry, vol. 3, No. 3, pp. 191-198, Jun. 1999.
Wang et al., Gliding Arc Plasma for CO2 Conversion, Chemical Engineering Journal, vol. 330, pp. 11-25, 2017.
Yaacoby-Bianu et al., Compassionate Nitric Oxide Adjuvant Treatment of Persistent *Mycobacterium* Infection in Cystic Fibrosis Patients, The Pediatric Infectious Disease Journal, vol. 37, No. 4, Apr. 2018.

Yu, et al., "Detection and Removal of Impurities in Nitric Oxide Generated from Air by Pulsed Electrical Discharge", Nitric Oxide, vol. 60, pp. 16-23, Nov. 30, 2016.
Yu, et al. "Development of a Portable Mini-Generator to Safely Produce Nitric Oxide for the Treatment of Infants with Pulmonary Hypertension", Nitric Oxide, vol. 75, pp. 7-76, May 1, 2018.
International Search Report in PCT/US2021/038149 dated Nov. 12, 2021.
U.S. Appl. No. 15/907,241 2018/0243527 U.S. Pat. No. 10,286,176, filed Feb. 27, 2018 Aug. 30, 2018 May 14, 2019, Systems and Methods for Generating Nitric Oxide.
U.S. Appl. No. 15/907,258 2018/0243528 U.S. Pat. No. 10,328,228, filed Feb. 27, 2018 Aug. 30, 2018 Jun. 25, 2019, Systems and Methods for Ambulatory Generation of Nitric Oxide.
U.S. Appl. No. 16/363,505 2019/0217042 U.S. Pat. No. 10,576,329, filed Mar. 25, 2019 Jul. 18, 2019 Mar. 3, 2020, Systems and Methods for Ambulatory Generation of Nitric Oxide.
U.S. Appl. No. 16/388,464 2019/0314596 U.S. Pat. No. 10,532,176, filed Apr. 18, 2019 Oct. 17, 2019 Jan. 14, 2020, Systems and Methods for Generating Nitric Oxide.
U.S. Appl. No. 16/697,498 2020/0094011 U.S. Pat. No. 10,695,523, filed Nov. 27, 2019 Mar. 26, 2020 Jun. 30, 2020, Systems and Methods for Generating Nitric Oxide.
U.S. Appl. No. 16/724,233 2020/0139072 U.S. Pat. No. 11,033,705, filed Dec. 21, 2019 May 7, 2020 Jun. 15, 2021, Systems and Methods for Ambulatory Generation of Nitric Oxide.
U.S. Appl. No. 16/875,971 2020/0361772, filed May 15, 2020 Nov. 19, 2020, Systems and Methods for Generating Nitric Oxide.
U.S. Appl. No. 16/875,687 2020/0360649 U.S. Pat. No 11,045,620, filed May 15, 2020 Nov. 19, 2020 Jun. 29, 2021, Electrodes for Nitric Oxide Generation.
U.S. Appl. No. 16/875,914 2020/0361773, filed May 15, 2020 Nov. 19, 2020, Architectures for Production of Nitric Oxide.
U.S. Appl. No. 17/146,468 2021-0214222, filed Jan. 11, 2021, Systems and Methods for Nitric Oxide Generation with Humidity Control.
U.S. Appl. No. 16/909,722 2020/0390994 U.S. Pat. No. 10,946,163, filed Jun. 23, 2020 Dec. 17, 2020 Mar. 16, 2021, Systems and Methods for Generating Nitric Oxide.
U.S. Appl. No. 17/197,911 2021/0268221 U.S. Pat. No. 11,376,390, filed Mar. 10, 2021 Sep. 2, 2021 Jul. 5, 2022, Systems and Methods for Generating Nitric Oxide.
U.S. Appl. No. 17/332,915 2022/0047837, filed May 27, 2021 Feb. 17, 2022, Systems and Methods for Ambulatory Generation of Nitric Oxide.
U.S. Appl. No. 17/331,793 2021/0353898, filed May 27, 2021 Nov. 18, 2021, Electrodes for Nitric Oxide Generation.
U.S. Appl. No. 17/352,225 2021/0395905, filed Jun. 18, 2021 Dec. 23, 2021, Systems and Methods for Preventing and Treating Infections with Nitric Oxide.
U.S. Appl. No. 17/503,223 2022/0135406, filed Oct. 15, 2021 May 5, 2022, Nitric Oxide Generation Process Controls.
U.S. Appl. No. 17/670,655 2022/0162070, filed Feb. 14, 2022 May 26, 2022, Systems and Methods for Generating Nitric Oxide.
U.S. Appl. No. 17/693,279, filed Mar. 11, 2022, Systems and Methods for Nitric Oxide Generation and Delivery.
U.S. Appl. No. 17/703,497 2022/0211967, filed Mar. 23, 2022 Jul. 7, 2022, Systems and Methods for Ambulatory Generation of Nitric Oxide.
U.S. Appl. No. 17/773,369, filed Apr. 29, 2022, Systems and Methods for Increasing Nitrogen Monoxide Concentration and Removing Nitrogen Dioxide from a Gas Stream.
U.S. Appl. No. 17/855,592, filed Jun. 30, 2022, Systems and Methods for Generating Nitric Oxide.
Lovich et al., "Generation of Purified Nitric Oxide from Liquid N204 for the Treatment of Pulmonary Hypertension in Hypoxemic Swine", Nitric Oxide vol. 37, pp. 66-77.

* cited by examiner

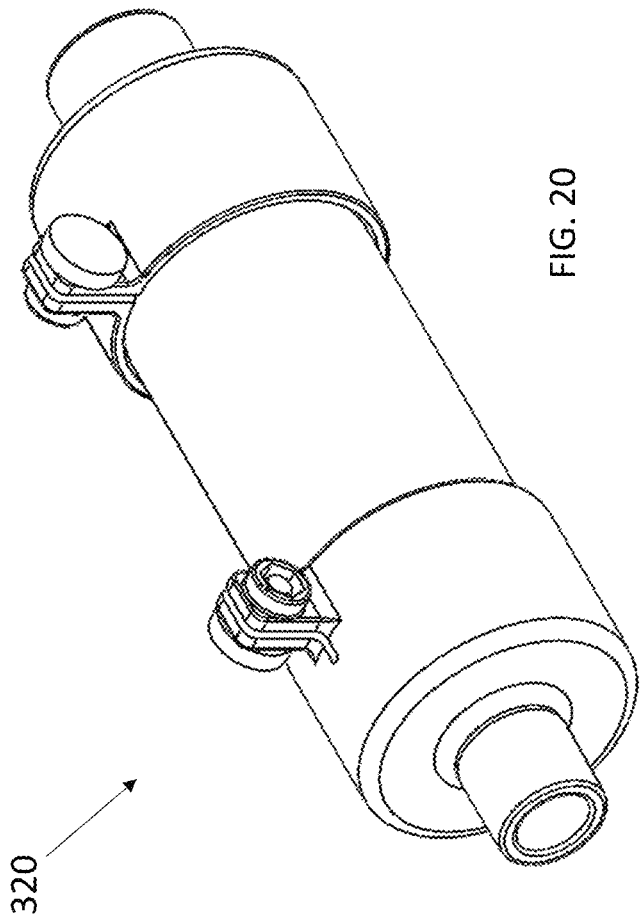

FIG. 20

- 22mm male (and internal 15mm female) / 22mm female connections
- Optional 15mm male inside 22mm female (not shown)
- O-ring seal (o-ring grooves shown in cap but could be on tube) -- simple radial seal and easily replaceable
- Allows the use of off the shelf tube cut to length (length can easily vary to support different amounts of soda lime).
- Open tube ends allow easy packing (tamping) of soda lime
- Open tube ends allow easy removal via "push through" of used soda lime
- Components easily cleaned
- Screen mesh to hold soda lime and trap larger particles (mounted inside and not shown)
- Can add borosilicate filter to trap smaller soda lime particles
- Cross pattern in cap supports screen
- Thumb screw (OTS) clamps cap to tube. Could have cam lever lock instead of thumb screw.

SYSTEMS AND METHODS FOR PREVENTING AND TREATING INFECTIONS WITH NITRIC OXIDE

RELATED APPLICATIONS

This application is a continuation patent application of U.S. application Ser. No. 17/352,225 filed Jun. 18, 2021, which claims the benefit of and priority to U.S. Provisional Application No. 63/194,145 filed May 27, 2021, U.S. Provisional Application No. 63/159,981 filed Mar. 11, 2021, and U.S. Provisional Application No. 63/040,982 filed Jun. 18, 2020, and the contents of each of these applications are hereby incorporated herein by reference in their entireties.

FIELD

The present disclosure relates to systems and methods for generating nitric oxide, and more particularly to the use of the generated nitric oxide for the prevention and/or treatment of infections, including microbial infections, fungal infections, bacterial infections and viral infections, including but not limited to COVID-19.

BACKGROUND

Low-dose inhaled nitric oxide treatment has been in practice for decades. Nitric oxide relaxes smooth muscle in the walls of pulmonary blood vessels, thereby decreasing the load on the right heart, decreasing pulmonary vascular resistance and increasing blood oxygen levels. Nitric oxide has also been shown to have viricidal and bactericidal effects. NO concentration within the nasal cavity of healthy volunteers has been measured to be 2 ppm, suggesting that low amounts of NO can be sufficient to stave off infection. In some applications, disinfection treatment is done at higher doses, 200 to 300 ppm NO for example, which has the potential of being faster-acting. For reference, typical inhaled NO concentrations to improve blood oxygenation are in the range of 1-80 ppm.

The objective of disinfection via NO is to dose the entire lung with sufficient concentration of NO to disinfect. In some applications, a minimum concentration of 150 ppm is applied for viricidal effect. In some applications, inhaled NO concentrations can be about 300 ppm, about 500 ppm, about 700 ppm, about 900 ppm, about 1100 ppm, or about 1300 ppm.

In some applications, inhaled NO concentrations reach as high as 1350 ppm. In some applications, inhaled NO concentrations range from 150 ppm to 1350 ppm, 200 ppm to 600 ppm, 300 ppm to 1200 ppm, 400 ppm to 1000 ppm, or 150 ppm to 1000 ppm.

NO changes the viscosity of mucous, improving the ability to clear gas pathways. In addition, NO changes the chemical properties of mucous, making it less hospitable for microbes. In addition, NO2 is water soluble and makes mucous more acidic which can deter/kill microbes.

Bacteria form a biofilm to protect themselves (i.e. a lipid boundary layer). Antibiotics are unable to pass through biofilms. Some drugs require entry into the bacteria so that their physiology can be altered leading to cell death. There are two strategies to gaining access for antibiotics to bacteria that are protected by a biofilm: 1) chemical break down the biofilm and 2) mechanical removal of biofilm. Both of these approaches can make drug-resistant bacteria susceptible to antibiotics. NO helps this process in three ways: 1) breaking down the biofilm chemically due to its lipophilic properties, 2) loosening mucus to facilitate mucous removal, and 3) acting directly on the bacteria to exact nitrosative and oxidative damage.

NO treatment can be done with tanks, however tanks are filled with high concentration NO gas (800 ppm typically) that gets diluted down to therapeutic concentration levels. It follows that tanks will last less time when higher concentrations of NO (less dilution) are delivered, because a tank begins with a finite number of NO molecules present. A further concern is that NO tanks are filled with a balance of $N_2$ (99.92%). Higher doses of NO result in higher levels of $N_2$ which can significantly decrease the inspired oxygen levels. As an example, a dose of 80 ppm from a tank of 800 ppm will dilute the inspired oxygen level by 10%. Since there is no oxygen in the tank NO, inspired oxygen decreases 10% from a typical atmospheric level of 21% to less than 19%. A dose of 160 ppm NO from an 800 ppm tank would dilute the inspired gas 20%, bringing inspired oxygen levels to roughly 17%. In many cases, supplemental oxygen is required in addition to tank NO to ensure adequate oxygen supply to a patient. This adds complexity and expense to a NO treatment. Thus, it is beneficial to have a system that is not limited by the volume and concentration of a tank, does not dilute atmospheric oxygen levels, and can generate NO on demand at the patient bedside.

SUMMARY

The present disclosure relates to systems, devices, and methods for nitric oxide generation for use with various ventilation and/or medical devices for the prevention and/or treatment of microbial infections, fungal infections, bacterial infections, viral infections, SARS, COVID-19, and other respiratory diseases and disorders. The systems and methods disclosed herein can be used to protect patients, caregivers, and the environment.

In some embodiments, a system for providing nitric oxide can include at least one pair of electrodes configured to generate a product gas containing nitric oxide from a flow of a reactant gas, and at least one controller configured to regulate an amount of nitric oxide in the product gas generated by the at least one pair of electrodes using one or more parameters as an input to the controller. One or more sensors are configured to collect information relating to at least one of patient information, the reactant gas, the product gas, and an inspiratory gas into which at least a portion of the product gas flows, the sensors configured to communicate the information to the controller to be used as the one or more parameters. The patient information includes information relating to a methemoglobin (MetHg) measurement collected from a MetHg sensor.

In some embodiments, the MetHg measurement from the MetHg sensor is used by the controller to generate an amount of the product gas based on at least one of a threshold MetHg level and a rate of change of the MetHg measurement. In some embodiments, the MetHg threshold level can be maintained by the controller for a predetermined time. In some embodiments, the MetHg measurement from the MetHg sensor is monitored by the controller such that the Methg measurement is maintained at less than the threshold MetHg level until a predetermined mass of NO has been delivered to the inspiratory gas.

In some embodiments, the MetHg measurement from the MetHg sensor is used by the controller to deliver an amount of the product gas based on at least one of a threshold MetHg measurement and a rate of change of the MetHg measurement. In some embodiments, a MetHg threshold level is maintained by the controller for a predetermined time. In some embodiments, the MetHg measurement from the MetHg sensor is monitored by the controller such that the Methg measurement is maintained at less than a threshold MetHg level until a predetermined mass of NO has been delivered to the inspiratory gas.

In some embodiments, the MetHg sensor is integrated into the system. In some embodiments, the controller is configured to dynamically change a NO dose using the MetHg measurement from the MetHg sensor to keep the MetHg measurement below a threshold while maximizing quantity of NO delivered. In some embodiments, the controller is configured to require an initial measurement from the MetHg sensor before NO delivery begins.

In some embodiments, the controller is configured to suspend NO generation based on the information from the MetHg sensor. In some embodiments, the controller is configured to resume NO generation when the MetHg measurement from the MetHg sensor decreases to a threshold level.

In some embodiments, the system can also include an injection pump configured to deliver methylene blue to a patient and in communication with the controller, the controller configured to control a delivery of the methylene blue to decrease a MetHg level.

In some embodiments, the controller is configured to vary a mass of NO delivered within each breath of the inspiratory gas from zero to a predetermined maximum value to deliver a target mass of NO per unit time. In some embodiments, a concentration of NO in the product gas is at least 150 ppm.

A method of generating nitric oxide (NO) can also be provided, and can include ionizing a reactant gas using at least one pair of electrodes to generate a plasma for producing a product gas containing nitric oxide within a flow comprising a reactant gas, and controlling an amount of nitric oxide in the product gas using one or more parameters as input to a control algorithm used by one or more controllers to control the electrodes, at least one of the one or more parameters being related to at least one of patient information, the reactant gas, the product gas, and an inspiratory gas into which at least a portion of the product gas flows. At least one of the parameters related to patient information is in the form of a methemoglobin (MetHg) measurement from a MetHg sensor such that the MetHg measurement is used by the controller to control the amount of nitric oxide delivered to a patient.

In some embodiments, controlling the amount of nitric oxide delivered to the patient includes the controller using a predetermined threshold MetHg level. In some embodiments, the controller monitors the MetHg measurement such that MetHg measurement remains below the predetermined MetHg threshold level. In some embodiments, the controller delivers a predetermined mass of NO to the inspiratory gas. In some embodiments, a MetHg level is maintained below the predetermined MetHg level until a predetermined mass of NO has been delivered to a portion of the inspiratory gas that is inhaled by a patient. In some embodiments, the controller is configured to vary a mass of NO delivered within each breath of the inspiratory gas to deliver a target mass of NO per unit time. In some embodiments, a concentration of NO in the product gas is at least 150 ppm.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 20 illustrates a perspective view of an embodiment of a tubular inspiratory gas scrubber;

Figure 1:
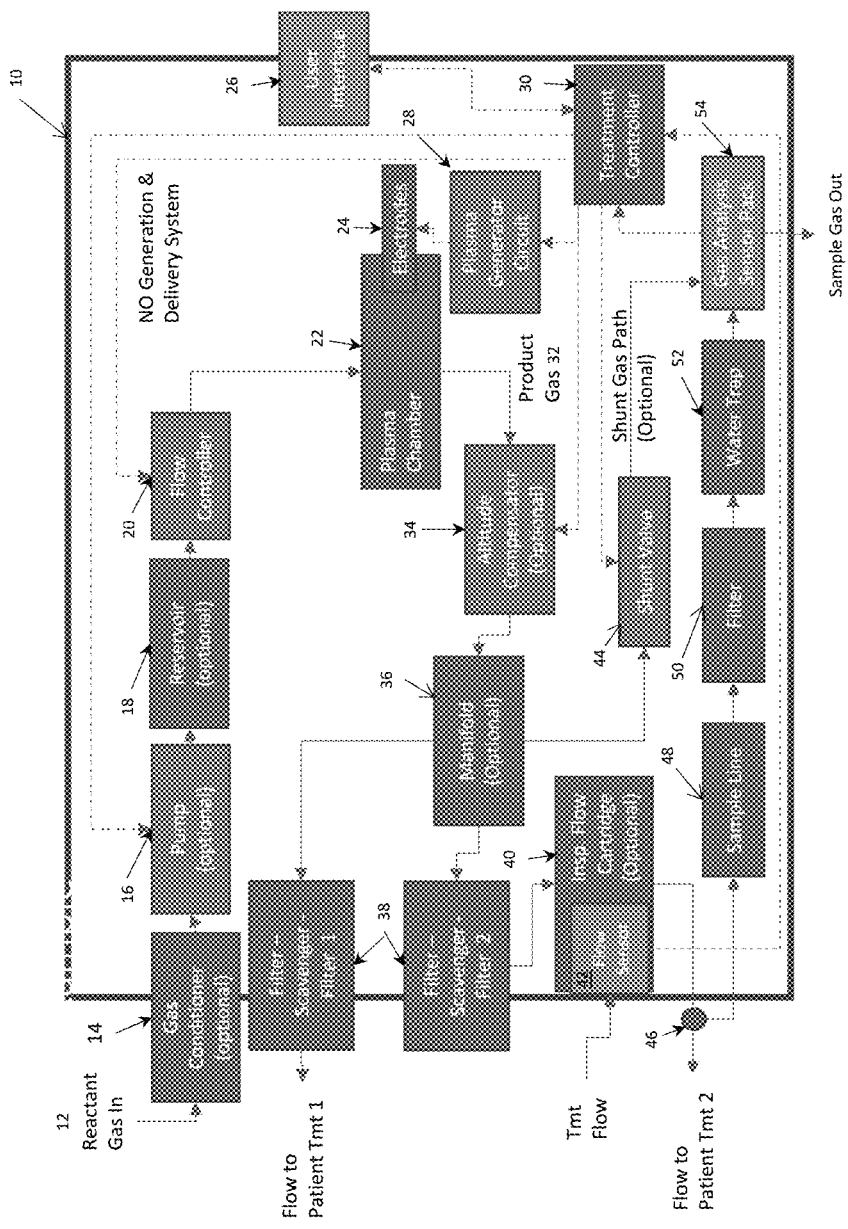
FIG. 1 is an exemplary embodiment of a system for generating NO-enriched product gas.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context. The term "flow" is inclusive of the terms "mass flow" and "standard flow" (i.e. the equivalent flow rate at standard temperature and pressure conditions).

Systems and methods for preventing and/or treating infections with nitric oxide (NO) are disclosed including systems, devices and methods for the generation, delivery and monitoring of nitric oxide to patients. Methods of delivering effective and controlled doses of nitric oxide are described. Applications including antimicrobial treatments are described for prophylactic applications to individuals and healthcare workers, as well as treatment of infected patients. Various treatment delivery methods and dosing strategies are described as well as a remote gas monitor device that can be mounted at or near the point of inspiration.

The presently disclosed embodiments can be used to prevent and/or treat infections, including microbial infections, fungal infections, bacterial infections and viral infections. The presently disclosed embodiments can be can be used to prevent and/or treat various respiratory ailments, disorders and diseases including, but not limited to, viruses, COVID-19, coronavirus, influenza, severe acute respiratory syndrome (SARS), Middle East respiratory syndrome (MERS), upper airway infections (i.e., sinusitis, stomatitis, etc.), lung infections (i.e., bronchitis, bronchiolitis, pneumonia, etc.), cystic fibrosis (CF), chronic obstructive pulmonary disease (COPD) or chronic obstructive lung disease (COLD), nontuberculous mycobacteria (NTM) or labored breathing, challenged breathing or any breathing difficulty It can also be used to treat blood prior to transfusion to bind with hemolyzed blood and prevent renal injury and hypertension.

The present disclosure relates to systems and methods of nitric oxide (NO) delivery for use in various applications, for example, inside a hospital room, in an emergency room, in a doctor's office, in a clinic, in an ambulance, in a patient transport helicopter, in the battlefield, in a patient transport fixed wing plane, in a ship hospital, nursing home, at home, and outside a hospital setting as a portable or ambulatory device. A NO generation and/or delivery system can take many forms, including but not limited to a device configured to work with an existing medical device that utilizes a product gas, a stand-alone (ambulatory) device, a module that can be integrated with an existing medical device, one or more types of cartridges that can perform various functions of the NO system, an electronic inhaler, and an electronic NO tank. The NO generation system uses a reactant gas containing nitrogen and oxygen, including but not limited to ambient air, to produce a product gas that is enriched with NO. In some embodiments, house compressed air from either a compressor or a cylinder is used. In some embodiments, a combination of one or more of house oxygen, house nitrogen, house air and ambient air are used as reactant gas. The NO generation device can include batteries, power supplies, connectors to receive external DC power, connectors to receive external AC power, a user interface, speaker, microphone, alarms, graphical display, carrying case, replaceable scrubber(s), replaceable filter(s), and other features that enable portability and use in the field.

A NO generation device can be used with any device that can utilize NO, including but not limited to a ventilator, an anesthesia device, house air compressor, a defibrillator, a ventricular assist device (VAD), a Continuous Positive Airway Pressure (CPAP) machine, a Bilevel Positive Airway Pressure (BiPAP) machine, a non-invasive positive pressure ventilator (NIPPV), high flow oxygen, a nasal cannula application, a nebulizer, an extracorporeal membrane oxygenation (ECMO), a bypass system, an automated CPR system, an oxygen delivery system, an oxygen concentrator, an oxygen generation system, and an automated external defibrillator AED, MRI, a humidifier, and a patient monitor. In addition, the destination for nitric oxide produced can be any type of delivery device associated with any medical device, including but not limited to a nasal cannula, a manual ventilation device, a face mask, inhaler, endotracheal tube, SCOOP catheter, or any other delivery circuit. The NO generation capabilities can be integrated into any of these devices, or the devices can be used with a NO generation device as described herein. For instance, a mask could contain a NO generator within it to facilitate continuous sterilization of inspired air.

Infected patients are administered NO with a variety of methods, including but not limited to a ventilator, CPAP, a face mask, and a breathing mouthpiece. In some embodiments, gas passing through the NO device is propelled by a patient's inspiratory effort (self-breathing). In some embodiments, for example patients receive continuous high flow therapy (e.g. 8 lpm for neonates and 70 lpm for adults) with either air or 02-enriched air as the carrier gas.

As with conventional NO therapy, nitrogen dioxide ($NO_2$), the result of nitric oxide oxidation, is monitored to ensure safe levels. Nitrogen dioxide is water soluble, forming nitric acid when it enters water. Acceptable limits of $NO_2$ are dependent on the exposure time. For example, at one time, the OSHA limit for an 8-hour workday was 5 ppm of $NO_2$. It follows that high dose NO treatments lasting 8 hours should stay below 5 ppm $NO_2$ and the lower the $NO_2$ level, the better. $NO_2$ levels greater than 5 ppm at shorter durations may be clinically relevant if supported by a clinical risk/benefit analysis. It will be understood that the $NO_2$ limit can vary. Selection of an acceptable $NO_2$ limit can be a function of one or more of the following parameters: NO dose, patient condition, criticality of NO therapy, duration of treatment, fraction of breaths dosed, inhaled oxygen levels, breath rate, and scrubber type.

Various features of a high dose NO generation and delivery device can decrease the level of $NO_2$ within the product gas. For example, soda lime scrubbers can be located within the NO generation device and/or in other locations between the device and the patient to absorb $NO_2$ such as a delivery tube, humidifier, mask, inspiratory limb, etc. Since $NO_2$ is formed by the oxidation of NO, the transit time from the plasma chamber to the patient can be minimized, thereby minimizing the time that NO can oxidize.

The NO oxidation rate is proportional to the square of the NO concentration. Another approach to reducing inhaled $NO_2$ levels is to dilute high concentration product gas exiting the plasma chamber of a NO generation device as soon as possible to benefit from the fact that NO oxidation rate is proportional to gas pressure. Soda lime is comprised of one or more alkaline materials including one or more of sodium hydroxide, calcium hydroxide and potassium hydroxide. It should be understood a scrubber is not limited to soda lime scrubbers, and that various $NO_2$-selective scrubbing materials can be used, including but not limited to ascorbic acid, 4-Hydroxy-TEMPO, and TEMPOL (formally 4-hydroxy-2,2,6,6-tetramethylpiperidin-1-oxyl, a heterocyclic compound).

System Overview

FIG. 1 illustrates an exemplary embodiment of a NO generation system 10 that includes components for reactant gas intake 12 and delivery to a plasma chamber 22. An optional gas conditioner is included in the system if the source of the reactant gas is uncontrolled. The gas conditioner can include one or more of particulate filtration, dehumidification, VOC removal, NOx removal and other steps. In some embodiments, reactant gas comes from a pressurized source, making the need for an internal pump optional. A flow controller maintains known flow rates through the plasma chamber to facilitate accurate NO production. In some embodiments, the flow rate through the plasma chamber is constant for one or more dose levels. In some embodiments, the reactant gas flow rate is variable. In some embodiments, the reactant gas flow rate is proportional to the NO production level.

The plasma chamber 22 includes one or more electrodes 24 therein that are configured to produce, with the use of a plasma generation circuit 28 (such as a microwave circuit), a product gas 32 containing a desired amount of NO from the reactant gas. The system includes a controller 30 in electrical communication with the plasma generation circuit 28 and the electrode(s) 24 that is configured to control the concentration of NO in the product gas 32 using one or more control parameters relating to conditions within the system and/or conditions relating to a separate device for delivering the product gas to a patient and/or conditions relating to the patient receiving the product gas. In some embodiments, the plasma generation circuit is a high voltage circuit that generates a potential difference across an electrode gap. In some embodiments, the plasma generation circuit is a radio frequency (RF) power generation circuit delivering RF power to one or more RF electrodes. In some embodiments, the RF power operates around 13.56 MHz with power in the 50-100 W range, however other power ranges can be effective depending on electrode design, production targets and reactant gas conditions. In some embodiments, RF power operates around 2.45 GHz for improved coupling and excitation of $N_2$ molecules. The controller 30 is also in communication with a user interface 26 that enables a user to interact with the system, view information about the system and NO production, and control parameters related to NO production.

In some embodiments, the NO system pneumatic path includes a pump pushing air through a manifold 36. The manifold is configured with one or more valves; three-way valves, binary valves, check valves, mass flow controllers, and/or proportional orifices. The treatment controller 30 controls the flow of the pump, the power in the plasma and the direction of the gas flow post-electrical discharge. By configuring valves within the manifold (not shown), the treatment controller 30 can direct gas to the manual respiration pathway, the ventilator pathway or the gas sensor chamber for direct measurement of NO, $NO_2$ and $O_2$ levels in the product gas. In some embodiments, respiratory gas (i.e. treatment flow) is directed through an inspiratory flow cartridge that measures the flow of the respiratory gas and merges the respiratory gas with NO product gas.

The output from the NO generation system in the form of the product gas 32 enriched with the NO produced in the plasma chamber 22 can either be directed to a respiratory or other device for delivery to a patient, or can be directed to a plurality of components provided for self-test or calibration of the NO generation system. In some embodiments, the system collects gases to sample in two ways: 1) gases are collected from a patient inspiratory circuit near the patient and pass through a sample line 48, a filter 50, and a water trap 52, or 2) gases are measured directly from the pneumatic circuit as they exit the plasma chamber 22. In some embodiments, product gases are shunted with a shunt valve 44 to the gas sensors after being scrubbed but before dilution into a patient airstream. Shunting of flow of product gas to the gas sensors may consist of the entire product gas flow or a portion of the product gas flow. In some embodiments, the gas sensors measure NO and/or $NO_2$ in the primary flow of product gas from the plasma chamber (no shunting) to enable continuous flow to the patient. In some embodiments, product gases are collected from an inspiratory air stream near the device and/or within the device post-dilution. Within the gas analysis portion of the device, the product gas passes through one or more sensors to measure one or more of temperature, humidity, concentrations, pressure, and flow rate of various gasses therein.

Figure 2:
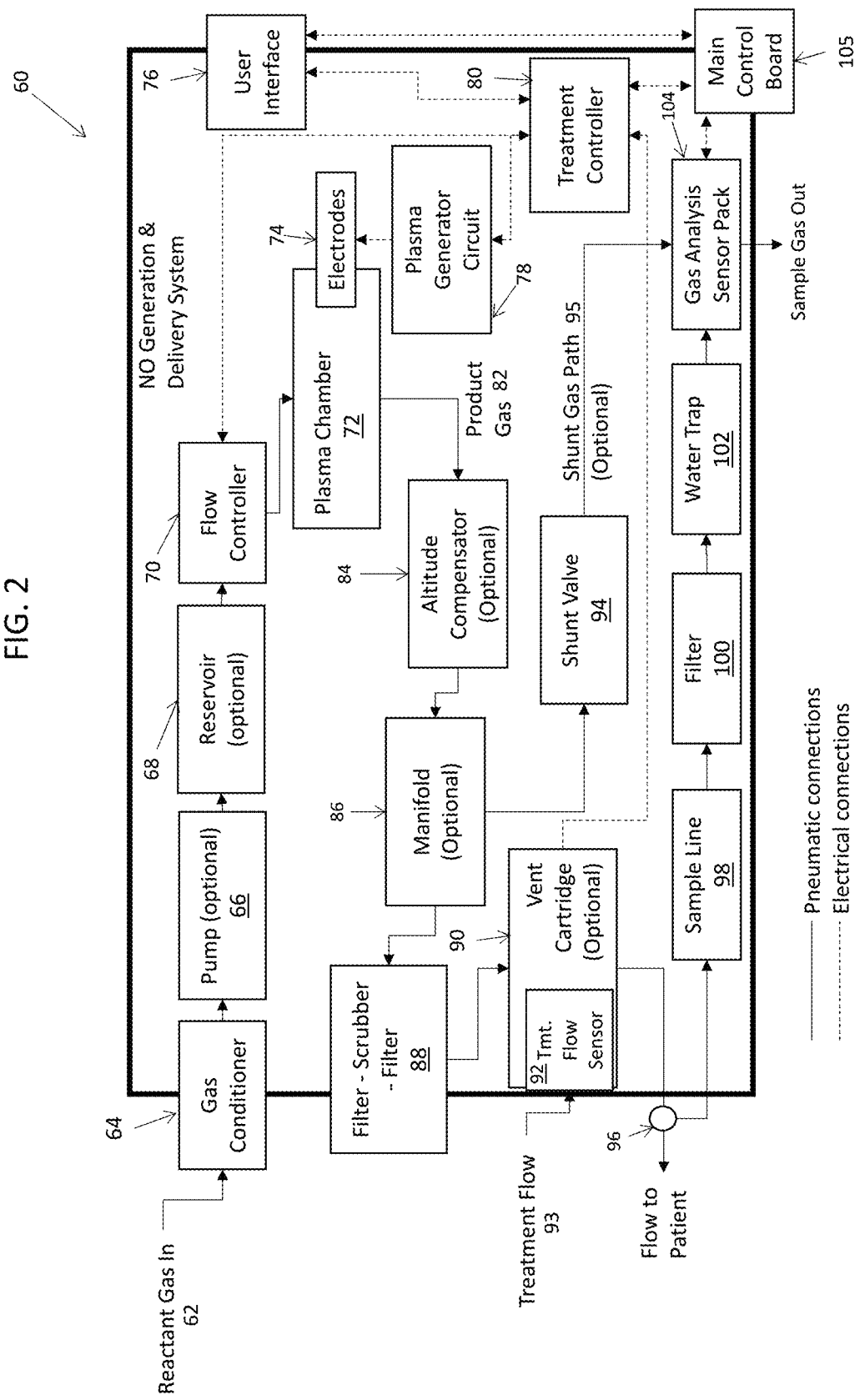
FIG. 2 is an exemplary embodiment of a system for generating NO-enriched product gas.

FIG. 2 depicts an embodiment of a NO generation and delivery system 60. Reactant gas 62 enters the system through a gas conditioner 64. The gas conditioner includes one or more of particulate filters, $NO/NO_2$ scrubbers, VOC scrubbers, and a humidity-altering stage. A pump 66 is used to propel gas through the system. Whether or not a system includes a pump can depend on the pressure of the reactant gas supply. If reactant gas is pressurized, a pump may not be required. If reactant gas is at or near atmospheric pressure, a pump or other means to move reactant gas through the system is typically required. A reservoir 68 after the pump attenuates rapid changes in pressure and/or flow from a pump. Coupled with a flow controller 70, the reservoir, when pressurized, can enable a system to provide flow rates to the plasma chamber 72 that are greater than the pump 66 flow rate for brief periods of time (pulsatile gas flow). This enables the use of a smaller, lighter, quieter and more efficient pump because a pump can operate continuously instead of generating peak flows instantaneously. Electrodes 74 within the plasma chamber 72 are energized by a plasma generation circuit 78 that produces high voltage inputs based on desired treatment conditions received from a treatment controller 80. A user interface 76 receives desired treatment conditions (dose, treatment mode, etc.) from the user and communicates them to the main control board 105. The main control board 105 relays to the treatment controller 80 the target dose and monitors measured NO concentrations from the gas analysis sensor pack 104. The main control board 105 monitors the system for error conditions and generates alarms, as required.

The reactant gas 62 is converted into product gas 82 when it passes through the plasma chamber 72 and is partially converted into nitric oxide and nitrogen dioxide. An altitude compensator 84, typically consisting of one or more valves (for example, proportional, binary, 3-way), is optionally used to provide a back-pressure within the plasma chamber 72 for additional controls in nitric oxide production. Product gases pass through a manifold 86, as needed, to reach a filter-scrubber-filter 88 assembly that removes nitrogen dioxide from the product gas. From the filter-scrubber-filter 88, product gas is introduced to a patient treatment flow directly, or indirectly through a treatment flow cartridge 90. In some embodiments, the treatment flow cartridge 90 includes a sensor 92 that measures the treatment flow 93. The treatment flow measurements from the sensor 92 serve as an input into the reactant gas flow controller 70 via the treatment controller 80. The sensor 92 measures one or more properties of the treatment gas from the following list: flow rate, pressure, water content/humidity, and oxygen level. After product gas 82 is introduced to the treatment flow, it passes through inspiratory tubing. In the treatment flow line, a fitting 96 is used to pull a fraction of inspired gas from the inspiratory flow, through a sample line 98, filter 100, water trap 102 and Nafion tubing to prepare the gas sample and convey it to gas sensors 104. Sample gas exits the gas analysis sensor pack 104 to ambient air. In some embodiments, sample gas is scrubbed for $NO/NO_2$ prior to release to atmosphere (not shown). In some embodiments, the system 60 can optionally direct gas through a shunt valve 94 and shunt gas path 95 directly to the gas sensor pack and out of the system. In some embodiments involving the shunt valve 94, the manifold 86 includes a valve (not shown) to block flow to the filter-scavenger-filter when the shunt valve 94 is open.

Figure 3:
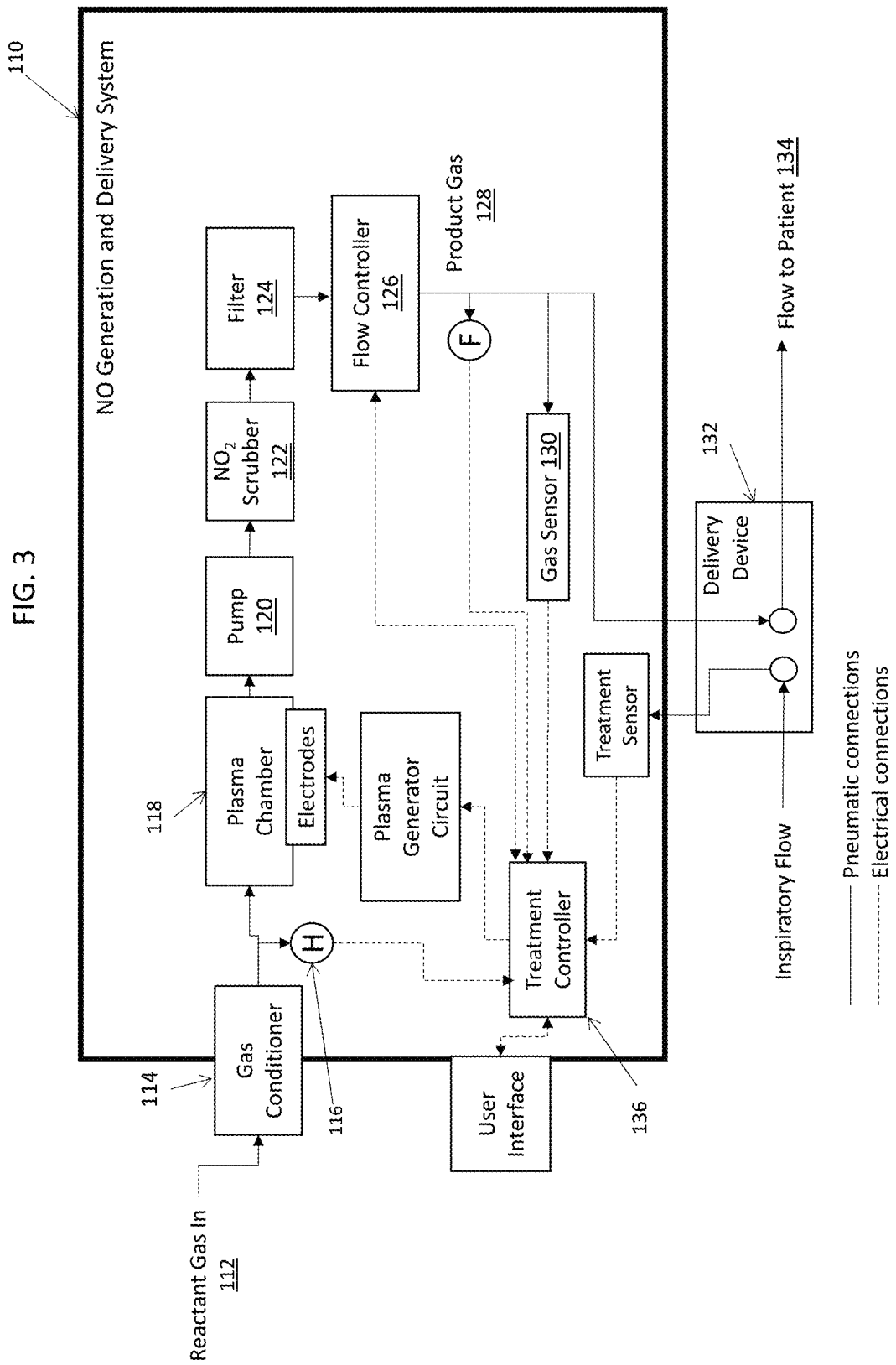
FIG. 3 is an exemplary embodiment of a system for generating NO-enriched product gas.

FIG. 3 depicts another embodiment of a NO generator. Reactant gas 112 enters the system 110 and passes through a gas conditioning component 114 that does one or more of filter for particulates, remove VOCs, remove NOx, remove SOx, adjust water content. After the gas conditioning component 114, the reactant gas passes by a humidity sensor 116. The humidity sensor 116 can be utilized to detect whether or not the reactant gas humidity is at the target humidity. The humidity measurement can also be used an input to the NO generator controls for compensation for water content in the reactant gas. As reactant gas passes through a plasma chamber 118, NO and $NO_2$ are formed from the elevated temperature of the plasma. The gas exiting the plasma chamber is referred to as "product gas."

Product gas passes through a pump 120, a $NO_2$ scrubber 122, and a particulate filter 124 prior to arriving at a flow controller 126. In some embodiments, the flow controller is in the form of a simple, binary valve. In some embodiments, the flow controller is in the form of one or more mass flow controllers with flow feedback from a flow and/or pressure sensor. Product gas 128 passes by one or more optional gas sensors 130 that indicate the quantity of NO and/or $NO_2$ in the product gas stream. In some embodiments, this information can be utilized for closed-loop control of NO production. In some embodiments, this information is utilized to detect whether or not the $NO_2$ scrubber is at or near the point of exhaustion. Product gas exits the device and passes through a delivery device 132 to a patient inspiratory gas stream 134.

The NO generator shown in FIG. 3 can be used to measure inspiratory activity. This can be accomplished by measuring one or more of pressure, flow, temperature, tube strain, sound levels, and other means. In the embodiment shown, the sensor receives a pneumatic signal from the inspiratory stream (e.g. pressure). In some embodiments, the sensor is located in the delivery device and the connection to the NO generator is electrical (e.g. flow sensor in the inspiratory stream).

A treatment controller 136 receives user inputs for patient parameters and dose level. Typically, a software-controlled, electro-mechanical device, the treatment controller utilizes user inputs and sensor inputs to generate plasma and flow control parameters that govern the production and delivery of NO to the patient.

Figure 4:
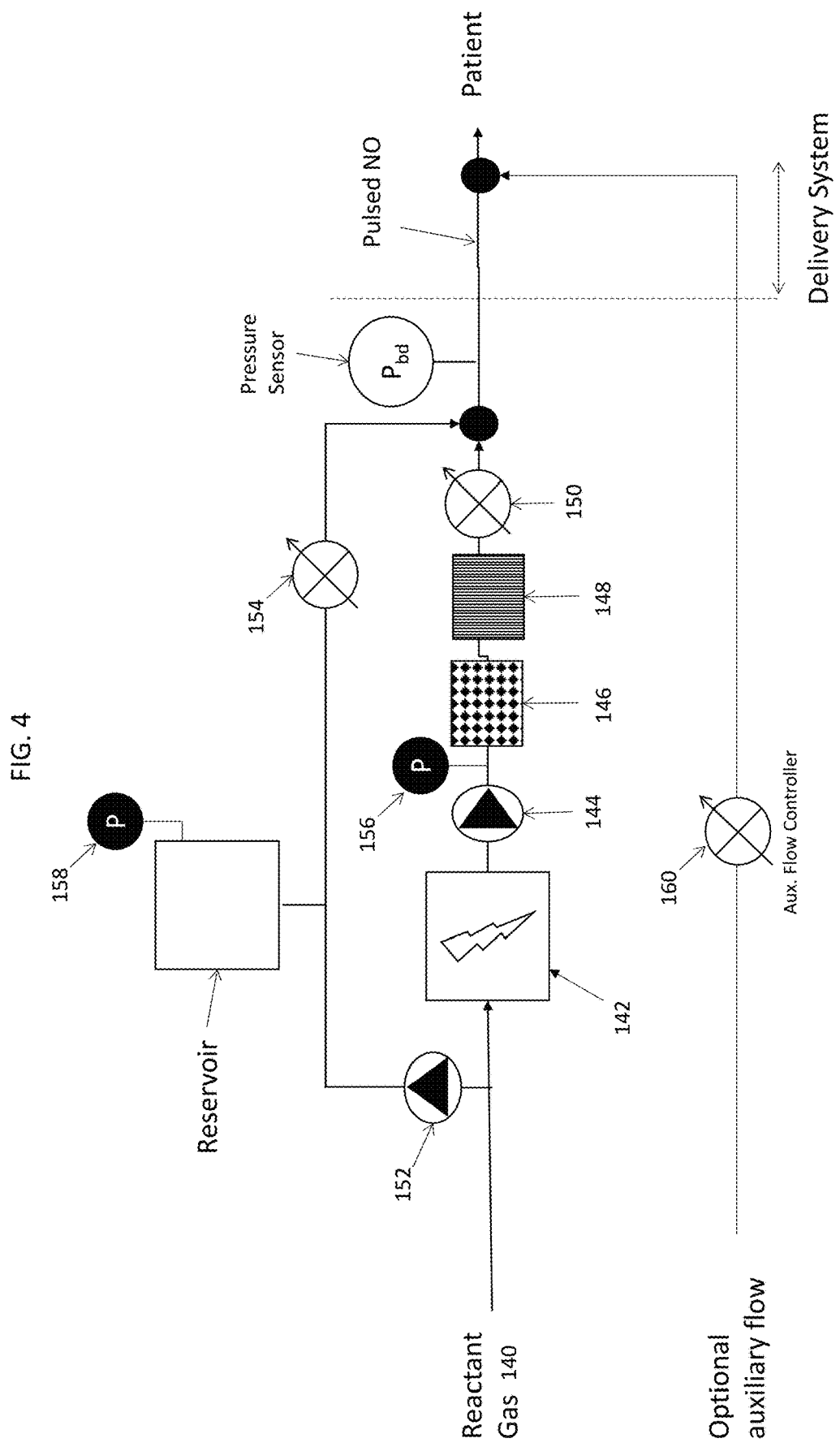
FIG. 4 is an exemplary embodiment of a system for generating NO-enriched product gas having a recirculation flow path.

FIG. 4 depicts another exemplary NO generation and delivery system that includes a recirculation feature. Reactant gas 140 enters the system and can be from a dry source (for example, house air, from a gas cylinder, etc.) or be at least partially dried by a portion of the system (not shown). At least partially drying of the reactant gas is required to prevent condensation within the pressurized portions of the system when the water content within the gas is sufficiently high. The flow bifurcates into a plasma flow path and a bypass flow path. The plasma flow path consists of a plasma chamber 142, a pump 144, a scrubber 146, a particle filter 148, and an exit flow controller 150 (mass flow controller, valve, etc.). As reactant gas passes through the plasma chamber, plasma between the electrodes of the chamber convert a portion of the $N_2$ and $O_2$ within the reactant gas to NO and $NO_2$. The bypass flow path consists of a pump 152 and a volume and exit flow controller 154 (mass flow controller, valve, etc.). The volume can be a discrete accumulation chamber or just consist of pneumatic tubing. The system operates by filling the pressurized reservoirs to a target pressure, as indicated by the pressure sensors 156, 158. When a patient initiates a breath, the system detects the inspiratory event with one or more method including pressure sensor (shown), flow sensor, communication from a concomitant treatment device (e.g. ventilator, CPAP). In response to the triggering event, the system releases pressure from the scrubber to the delivery system, followed by a pulse of pure reactant gas from the pressurized reservoir. This design prevents NO from aging within a non-scrubbed portion of the system between breaths, thereby decreasing inhaled $NO_2$ levels. Furthermore, less NO is generated overall because NO is only released into the patient inspiratory volume. This provides for an increase in battery life, electrode service life, and scrubber service life. In some embodiments, the flow rate through the plasma chamber is constant and the NO production level is constant as the NO is released from the scrubber in boluses. Boluses of NO can be short (10-200 msec) or long (200-1000 msec), depending on the breath rate and the zone within the breath that is being targeted for treatment (e.g. entire lung, deep lung, upper lung).

FIG. 4 depicts an optional auxiliary flow that can be used to provide one or more of additional oxygen and dilution to achieve a variable (e.g. user specified) target inhaled NO concentration. In some embodiments, the NO generator delivers a constant production level of NO and the auxiliary flow varies to vary dilution level and achieve a target inhaled concentration. The auxiliary flow rate can be varied manually by a user, or automatically controlled by either the NO generation device or a separate device (e.g. CPAP, Ventilator). In some embodiments, the auxiliary flow is constant. In some embodiments, the auxiliary flow is pulsatile, synchronized with patient inhalation. The NO generator can include a flow sensor 160 within the auxiliary flow to achieve one or more of the following: synchronized NO pulses with auxiliary flow, and maintain target inhaled NO concentration.

Figure 5:
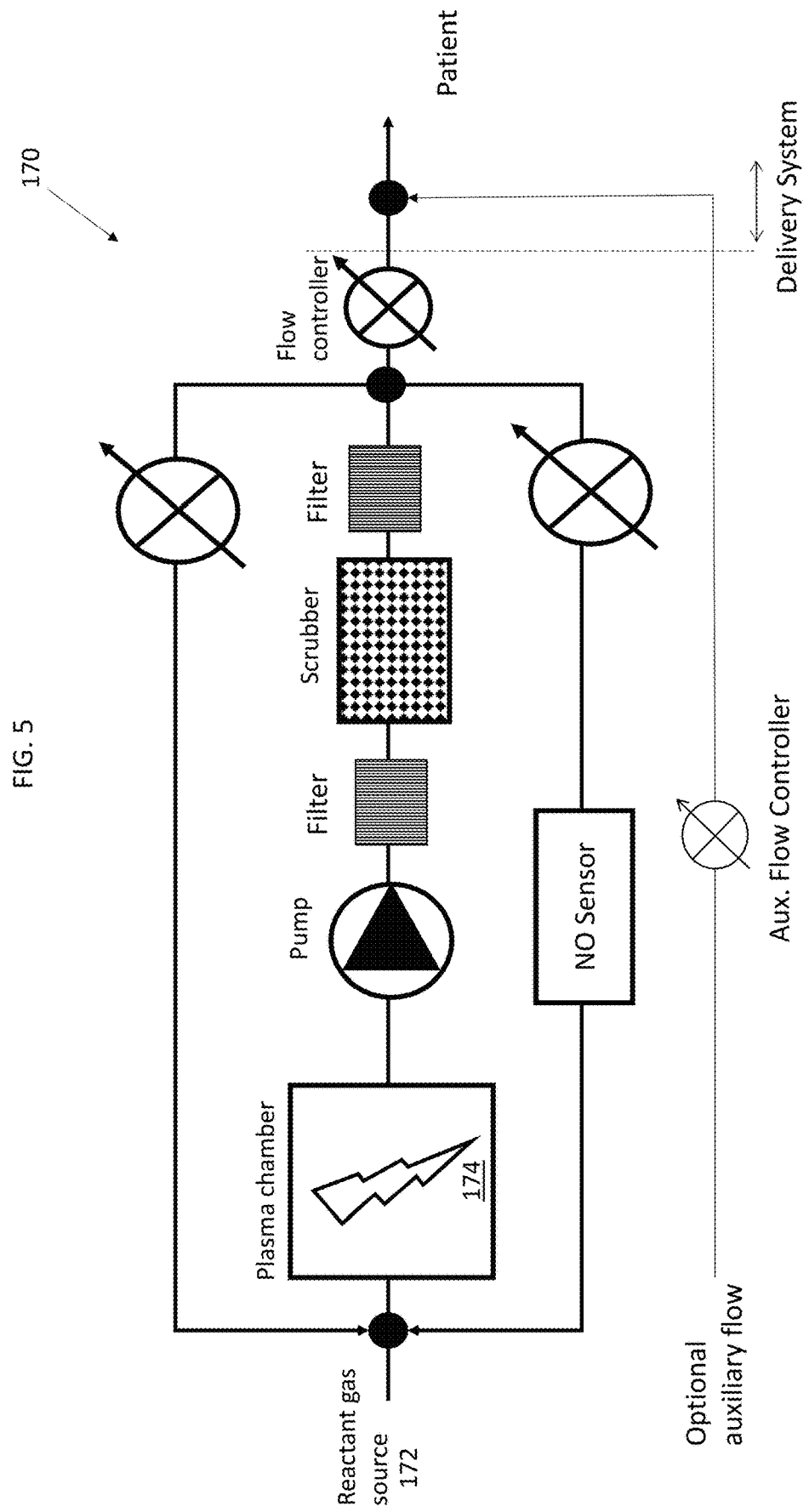
FIG. 5 is an exemplary embodiment of a system for generating NO-enriched product gas having an auxiliary flow path.

FIG. 5 depicts another embodiment of a NO generation system 170 for high concentration NO therapy. Reactant gas 172 enters the system and passes through a plasma chamber 174 where a portion of the reactant gas is converted to NO and $NO_2$, generating a product gas. Flow of gas is propelled by a pump component. Downstream of the pump is a filter-scrubber-filter to remove particles (electrode, scrubber material, and other sources) and $NO_2$ from the product gas. The product gas flow then splits into three paths, each controlled by a flow controller. In some embodiments, the three flow controllers are controlled in a way that pressure upstream of the flow controllers remains constant. One of the flow paths provides a flow of product gas to a NO sensor and returns gas to the entrance of the system. A second path returns gas to the entrance of the system. The third path controls flow of product gas to the patient. In some embodiments, the system controls plasma activity to maintain a constant concentration within the recirculation loop(s), upstream of the third (patient) flow path. In some embodiments, the concentration of product gas within the system ranges from a treatment minimum (150 ppm for disinfection applications) to 10,000 ppm.

Dose Delivery

Constant Inhaled Concentrations

Figure 6:
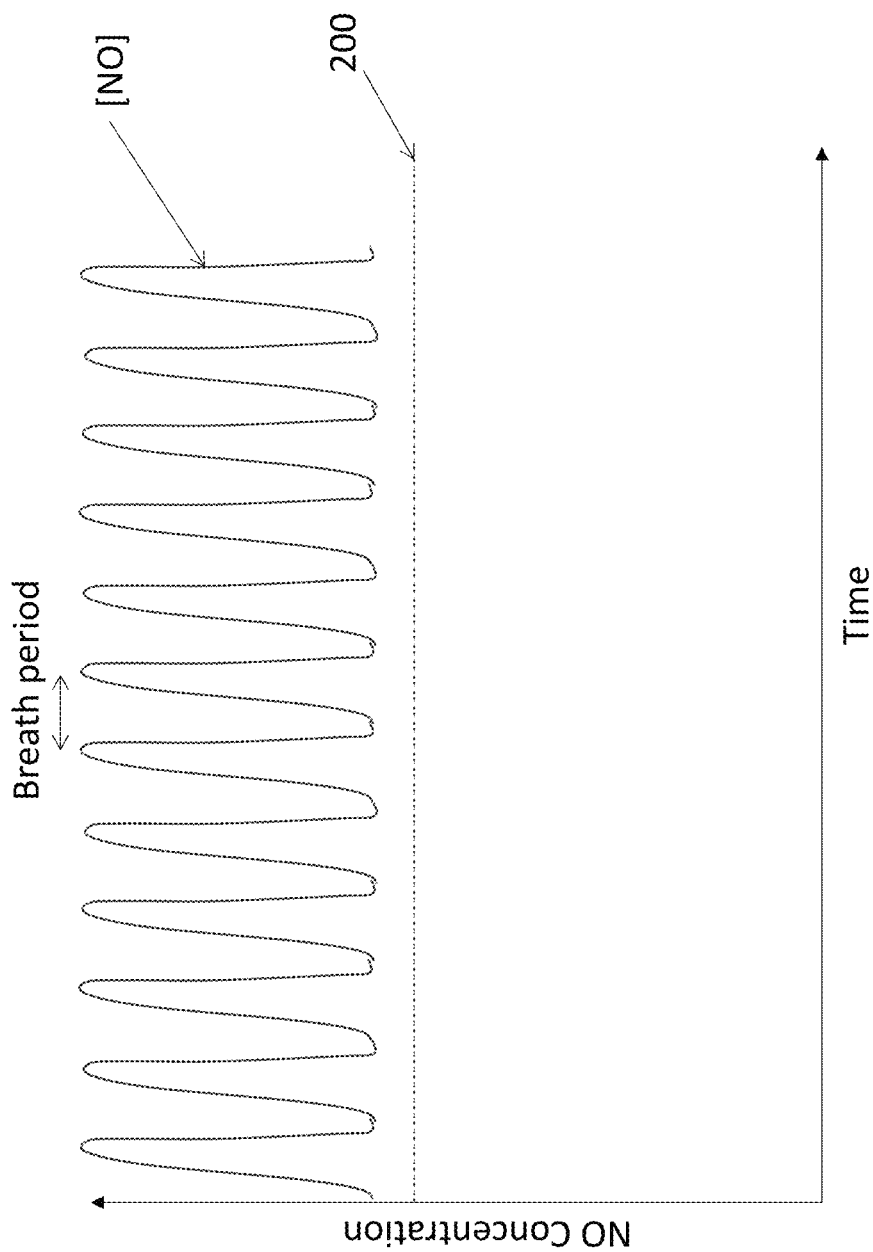
FIG. 6 illustrates an exemplary graph showing a treatment in which NO concentration varies but remains above a bactericidal/viricidal threshold.

In some embodiments, the inhaled concentration during disinfecting NO therapy is constant. This can provide an even NO dose throughout the lung of the patient. Constant NO generation and injection into the inspiratory flow produces constant NO concentrations in constant inspiratory flows. The same results occur when NO from a tank is delivered constantly to a constant inspiratory flow. When inspiratory flow is pulsatile, as in ventilator treatments, constant NO production results in variable concentrations of NO within the inspiratory pathway. Periods of high inspiratory flow have lower concentration from the constant flow of NO, and periods of low inspiratory flow have higher concentration. These variations in NO concentration are not necessarily an issue in high dose NO therapy so long as the minimum concentration within the inspired gas is greater than the bactericidal/viricidal/fungicidal concentration required to be therapeutic. FIG. 6 depicts a graph showing a treatment in which NO concentration varies but remains above a bactericidal/viricidal/fungicidal threshold (shown as line 200).

Proportional Flow

In some embodiments, a high-concentration therapy NO generator delivers constant concentration NO to the inspiratory limb in proportion to the inspiratory flow rate, creating a constant concentration of NO in the inspired gas.

Pulsed Flow

In some embodiments, NO is only introduced to the inspiratory flow during periods of inhalation. This approach conserves NO by ensuring that generated NO is delivered to the patient. This efficiency with NO production results in increases in battery life, electrode life, and scrubber life for example. Pulsed NO flow can also allow for NO to be stored within the device, which can provide a longer residence time within the scrubber which can provided a higher level of scrubbing efficiency (percent $NO_2$ removal). Pressurized scrubbers can remove 95 to 100% of the $NO_2$ that enters the scrubber. The scrubber also removes $NO_2$ that forms due to oxidation of NO within the scrubber. Pulsed NO can be delivered near the patient, thereby decreasing the exposure time of high concentration NO to high concentration oxygen, resulting in less NO oxidation.

Mixing Element

In some embodiments, a mixing element is placed within the inspiratory limb to mix NO and inspiratory gas post-NO injection. Similarly, a mixing element can be used to mix oxygen with inspiratory gas and/or NO after introduction of oxygen to the inspiratory gases. In some embodiments, oxygen is introduced to the inspiratory flow at the latest possible point (e.g. ET tube, Patient Wye connector, proximal ventilator tubing, mask, scoop catheter, nasal cannula prong) to minimize oxidation of NO which increases significantly with oxygen concentration.

Face Mask

In some embodiments, NO is delivered to a patient through a face mask. As a patient exhales, exhaled gases can contain levels of NO and $NO_2$ which can collect in the environment. In some embodiments, a face mask includes a $NO_2$ and/or NOx scrubber that scrubs exhaled gases before release from the system. In some embodiments, the NOx scrubber is made one or more materials including one or more of potassium permanganate, activated carbon, soda lime, and TEMPO. In some embodiments, a filter, such as a HEPA filter, is used to filter infectious particles from the exhaled gas from a mask.

Secondary Pump

In some embodiments, the inspiratory flow pressure can exceed the pressure within the NO generation system. In some embodiments, a NO generation system includes a product gas pump that increases the pressure of product gas so that it can flow into a pressurized flow of inspiratory gas. In some embodiments, the pump operates at a constant rate to pressurize product gas. In some embodiments, the product gas pump flow rate varies in relation to the inspiratory flow pressure. In some embodiments, the product gas pump flow rate is proportional to the inspiratory flow rate. In some embodiments, a NO generation system operates at a pressure that is always higher than the inspiratory gas so that product gas can always flow towards the patient.

NO Generation in Inspiratory Flow

Given that a NO generator sources $N_2$ and $O_2$ from the atmosphere, it does not dilute $O_2$ levels in the same way that tank NO can. Tank NO is comprised of NO in a balance of nitrogen. Due to the fixed concentration of NO gas within the tank, increased doses of NO require an increased volume of NO which decreases inspired $O_2$ levels. In contrast, a NO generation device generates NO in a reactant gas flow containing $N_2$ and $O_2$. When additional NO is required, plasma activity can be altered to convert a greater portion of the reactant gas to NO without increasing the amount of reactant gas and altering inspiratory oxygen dilution significantly. As a result, the level of dilution of inspiratory flow from a NO generation device can be lower than that of tank-sourced NO. This can be important for patient treatments where high inspired oxygen concentrations are required. For example, during low dose NO therapy (0 to 80 ppm), it can be important to not dilute the inspiratory flow more than 10% with NO-containing gas. This limit stems from a desire to not dilute 100% $O_2$ cases more than 10% and due to the risk of interfering with concomitant therapies, such as ventilators that may alarm in the presence of excessive changes in gas volume/pressure within the ventilator circuit. For high dose NO treatment, there is not the same limitation to dilution, owing to the fact that 100% $O_2$ is not typically used. Given that 100% $O_2$ is not typically used in high-dose NO treatments, $N_2$ and $O_2$ are present within the inspiratory gas enabling NO to be generated within the entire inspiratory flow in some cases. In some embodiments, NO is generated in a side stream sourced from the inspiratory flow. In some embodiments, ambient air is sourced for NO generation and merged with inspiratory flow. In some embodiments, $N_2$ and $O_2$-containing gas is sourced from a cylinder or hospital air supply. In some embodiments, $N_2$ and/or $O_2$-containing gas is sourced from an oxygen concentrator. The higher the concentration of NO in the NO-containing gas, the lower the level of inspiratory flow dilution is required to achieve a target NO dose. Lower levels of dilution decrease the risk of affecting concomitant therapies. For example, ventilators can accommodate a certain level of difference between output gas and input gas. When a NO device is added to the ventilation circuit, gas volume is added from the NO device and subtracted from the flow for gas sensor measurements. The net volume change to the inspiratory circuit should be minimized to minimize disruption to the ventilator treatment.

Variable Production

When NO is generated and delivered at a constant concentration and flow rate into a dynamic inspiratory flow, the inhaled concentration can vary. For example, this can be the case in a CPAP application where gas flow rate is little to none (slow flow rate) between breaths and then surges as the patient inspires. With constant NO generation and delivery, periods of low inspiratory flow, i.e. between breaths, result in higher NO concentrations than periods of high inspiratory flow rate. The location of the zone of high concentration NO with respect to the patient depends on the length of tubing between injection point and patient. This zone of high concentration can be leveraged to improve overall device efficiency if the system can be designed so that the zone of high concentration NO is the volume of gas that is inspired by the patient. In some embodiments, NO is generated continuously at a low level that sufficiently doses the slow-moving gas between breaths and ensures that the slow moving, accurately dosed gas is inspired. In some embodiments, a NO generator only generates plasma during the slow flow rate between breaths to save energy while ensuring that the slow-moving, accurately dosed gas is inspired. Ensuring that the slow moving, accurately dosed gas is inspired is a function of the slow flow rate and the inspiratory gas volume between the NO injector and the patient. This volume can be comprised of tubing, a bag, a rebreather mask, a humidifier, a gas sample port, fittings and other inspiratory pathway components. These approaches effectively pre-load a lung's worth of air at the correct concentration while running at much lower production rates than would be needed to accurately dose the peak inspiratory flows. It can be used in applications where the volume of gas between the NO generator and the patient is well-controlled.

In some embodiments, a NO device is configured to dose a bias flow with a target NO concentration. The volume of tubing between the NO device and the patient is sized to be as large or greater than the tidal volume of the patient so that the volume of inspired gas comes from bias flow. In this case, the bias flow needs to be of sufficient volumetric flow rate to replace the entire tubing volume between breaths. For example, consider a patient breathing at ten 500 ml breaths per minute at an inspiration to expiration ratio of 1:2. The breath period is 6 seconds (60 seconds/10 bpm). The inspiratory time is 2 seconds and the expiratory time is 4 seconds. The tubing volume should be 500 ml or more so that it can be filled with evenly dosed NO gas. To ensure that the tubing is completely purged between breaths, the bias flow must be sufficiently high. If the tubing volume is 500 ml (1.3 m of a 22 mm ID ventilator tube), for example, the bias flow must be at least 500 ml/4 sec, or 125 ml/sec, or 7.5 lpm. This method eliminates the potential for the patient to breath under-dosed inspiratory gas associated with the inspiratory bolus. As an example, if the patient inhales at a rate of 52.5 lpm, a 7-fold increase in flow rate (52.5/7.5=7), the concentration of gas dosed by the system during inspiration will be 7 times less than the target. Thus, if the NO generation device delivers sufficient NO to dose a constant flow of 7.5 lpm of inspiratory gas, the patient will breath evenly dosed NO despite there being volumes of gas generated during inspiration that are underdosed. The under-dosed gas sweeps by the patient during patient exhalation and the patient inspires accurately dosed gas in phase with the bias flow. This approach works for all respiratory rates, so long as the bias flow is high enough to purge the inspiratory limb between breaths and the volume of the inspiratory limb is as large or greater than the inspiratory volume. Faster respiratory rates, provide less time to purge the gas volume between injector and patient, requiring faster bias flows to purge the gas volume in time. It follows that slower respiratory rates result in greater time to purge the gas volume. In some embodiments, the bias flow is faster than necessary, i.e. it purges the gas volume between NO injector and patient in less time than the duration of exhalation and pause prior to the next inspiration. In this case, a NO device may only introduce NO to the inspiratory limb during the latter part of the bias flow phase so that the gas volume to be inspired is primed with sufficient NO just before patient inhalation.

This concept of being in phase with the bias flow provides a means of NO dose control. If breathing gas accurately dosed during the bias flow provides a maximal level of NO, lower levels of NO can be delivered to the patient by being less in phase. For example, in a system that delivers NO constantly to accurately dose a bias flow, if the inspiratory limb is shortened, the volume of accurately dosed gas that enters the patient will be less, thereby decreasing the delivered dose. In some embodiments, the early portion of a breath can be dosed accurately, and the latter portion of the breath can be dosed at a lesser extent or not at all. In this case, the volume of tubing between NO generator and patient can have less volume than the tidal volume because later portions of the breath will be supplied by gas that was flowing faster than the bias flow at the point of injection and will have lower concentration.

Zero Bias Flow

In some patient treatments, there is little to no flow past the NO device between breaths. This is the case with some ventilators and CPAP machines as well as when a patient is providing the inspiratory flow themselves. For example, a NO device can deliver NO into an inspiratory limb during a period of zero bias flow (patient exhalation) at the target inhaled concentration thereby filling the inspiratory volume with an accurate number of moles of NO. When the patient inhales, the inspiratory volume enters the patient, delivering the entire bolus of NO to the patient when the inspiratory limb volume is less than the inspired volume. Positioning of the NO bolus within the inspiratory limb and coordination with the inspiratory flow device is important for accurate and reliable patient dosing with this approach. Benefits of this approach include reducing the total amount of NO required to be generated, owing to the accurate and complete delivery of the NO. This reduction in NO generation enables increases in battery life, electrode service life and scrubber service life.

Dose Accuracy

Acceptable Concentrations

As mentioned earlier, significant variations in NO concentration can be deemed acceptable for disinfection treatment so long as the minimum inhaled NO concentration is therapeutic. For example, fluctuations of about 150 ppm to 300 ppm during the inspiratory cycle have been deemed acceptable in some cases. In other examples, fluctuations of about 150 ppm to 1350 ppm NO have been deemed acceptable. Acceptance of fluctuations can depend on many factors, including the duration of treatment, and/or susceptibility of the target microbe to NO concentration. When inspiratory flows are variable, it is important to standardize the therapy, parameters, and dosing vernacular related to it. In some embodiments, the minimum NO concentration level of a dynamic inspiratory NO concentration is specified for a therapy. In some embodiments, the average inspiratory NO concentration of a dynamic NO concentration is specified. One or more of Root Mean Square (RMS) average NO production rate, arithmetic mean NO production rate, max NO inspiratory concentration, standard deviation of inspiratory NO concentration and other related factors have also been utilized to specify and/or characterize a NO treatment dose. In some embodiments, a NO delivery device is configured to deliver NO at a particular concentration or mass per breath to a total number of breaths (e.g. 100 breaths). In this case, the system monitors patient breathing directly (sensors on the patient or in the patient flow) or indirectly (from sensors or concomitant therapy devices) in order to count breaths. In some embodiments, a NO delivery device is configured to deliver a number of moles of NO molecules or a mass of NO within a period of time (e.g. x moles in y hours). The moles of NO are delivered within a target range of concentrations (e.g. >minimum lethal concentration for specific pathogen and <concentration that could be harmful to the patient). In some embodiments, a fixed quantity of NO molecules and/or concentration can be delivered in a specific number of breaths over a specified time (e.g. 400 ppm gas in 50 breaths within a 1-hour time period). In this approach, a system may dose a subset of breaths within the treatment window (e.g. 1 hour) instead of dosing every breath. One benefit of this approach is that the system can track a dosing run rate and does not have to accurately detect every breath in order to comply). This approach of limiting the amount of NO delivered over a period of time is a means to mitigate against the potential of methemoglobinemia while ensuring that sufficient dose is also delivered to treat a particular clinical condition (e.g. respiratory infection).

Dose Smoothing

In some embodiments, a variable reservoir is placed within the inspiratory limb to collect inspiratory flow between breaths and homogenize the NO concentration. The reservoir can be positioned in any location between the point of NO injection and the patient's nose/mouth, including but not limited to the inspiratory limb, a non-rebreather mask, or face mask. In some embodiments, NO delivery is constant into a variable flow inspiratory stream. Gas collects within the variable reservoir and mixes between breaths. As the patient breaths, the reservoir empties. Filling and emptying of the reservoir can be passive, active, or both. The inspiratory flow rate is set at or near the patient minute volume so that the reservoir does not over-fill or gradually become empty. In some passive embodiments, the reservoir is an elastomeric balloon, i.e. one made from a material that stretches (latex, silicone, rubber for example). In some passive embodiments, the reservoir is a rigid balloon, i.e. balloon made from a non-elastic material but still flexible (mylar, polyethylene, for example). In some active embodiments, a piston or bellows is actuated to fill and empty out of phase with the patient inspiratory cycle. Actuation of the piston or bellows can be achieved any number of ways, including but not limited to linear motor, motor-driven rack and pinion, crank-rocker mechanisms, balloon displacement in a rigid container, and other embodiments. This variable reservoir approach can attenuate the NO concentration fluctuations associated with constant NO delivery into a variable inspiratory flow by providing a volume and time for NO gas and inspiratory gas to mix.

In some embodiments, a scrubber is located between the variable reservoir and the patient to remove $NO_2$ that can form during residence within the bag. In some embodiments, the variable reservoir is at least partially filled with a scrubber material. In some embodiments, the variable reservoir is at least partially filled with an open-cell foam that is either constructed from or coated with a $NO_2$-scrubbing material.

Dose Ramping

Odors have an absolute threshold of detection and a difference threshold. The absolute odor threshold is the lowest concentration perceptible by the human nose. For NO, the absolute odor threshold is 0.3 to 1 ppm. For $NO_2$, the absolute odor threshold is 0.1 to 0.4 ppm. The difference threshold is the amount that a value needs to change before a person will recognize that change 50% of the time.

High concentrations of NO can be smelled by a patient and can be irritating. In some embodiments of NO treatment, the dose is gradually increased during a treatment session with increments in concentration that are less than the difference threshold. Gradual increases in NO decrease the ability of a patient to perceive high concentrations of NO thereby improving a patient's tolerance to treatment. Gradual increases in NO can also enable a person that is very sensitive to odors to receive NO treatment at all. This approach can also enable a patient to tolerate a longer treatment with NO, notwithstanding methemoglobin limitations. Similarly, NO concentration can be decreased from a maximal level in slow decrements that are imperceptible to the patient. In some embodiments, slow dose changes are utilized in clinical trials to decrease a patient's ability to perceive NO treatment, effectively blinding them in the study.

Dose Decreases

In some embodiments, the initial NO dose is at its maximum at or near the beginning of treatment. The patient is able to accommodate high doses of NO at this time because methemoglobin levels are low. As treatment continues, NO dose can be automatically decreased according to a treatment schedule and/or changes in methemoglobin level. This can prolong exposure to the NO for as long as possible, maximizing the antimicrobial efficacy of the treatment while maintaining patient safety.

Dose Balanced in Nitrogen

In some embodiments, NO is delivered in a balance of nitrogen to infected parts of the lung or to the entire lung. This can only be done in a subset of breaths to avoid hypoxemia, however it can provide higher doses of NO to the lung tissue to fight infection while practically eliminating the risk of $NO_2$ delivery. In an exemplary treatment, a patient breathes normally and receives a breath of 800 ppm NO balanced with $N_2$ every $10^{th}$ breath for 10 minutes. In another embodiment, the patient receives a breath of 200 ppm NO balanced with $N_2$ every minute for 15 minutes.

Prophylactic Prevention of Methemoglobinemia

Methemoglobinemia forms when nitric oxide oxides iron in heme to increase its affinity for oxygen. This results in reduced release of oxygen to tissues. Lethal levels of methemoglobin (MetHg) are 25%, however levels seldom exceed 10% in the clinic. Methemoglobinemia is treated with intravenous doses of a methemoglobin medication, such as methylene blue, ascorbic acid and riboflavin. In the case of a lung infection, the risk of methemoglobinemia must be balanced with the benefit of eliminating the infection. In some embodiments, a methemoglobin medication, such as methylene blue, is administered (e.g. 1-2 mg/kg body weight) to a patient prophylactically prior to and/or during nitric oxide treatment to prevent the onset of methemoglobinemia and enable higher doses of NO to be delivered to the infected lung and airway tissue.

The NO generation and/or delivery device can use a proportional integral derivative (PID) control scheme based on the MetHg measurement to vary NO injection to maintain MetHg below a threshold. In some embodiments, the NO generation and/or delivery device monitors the rate of change (i.e., the slope) of MetHg and adjusts the NO injection accordingly to prevent exceeding a threshold. For example, as the rate of change of the MetHg increase such that the MetHg level is rising at a faster rate, the controller of the NO system can slow down the NO injection or stop the generation of NO until the MetHg falls to an acceptable level or the rate of change of MetHg reaches an acceptable rate. In some embodiments, the NO generation/delivery system can also alarm in the event that indicated MetHg levels exceed a threshold.

Figure 34:
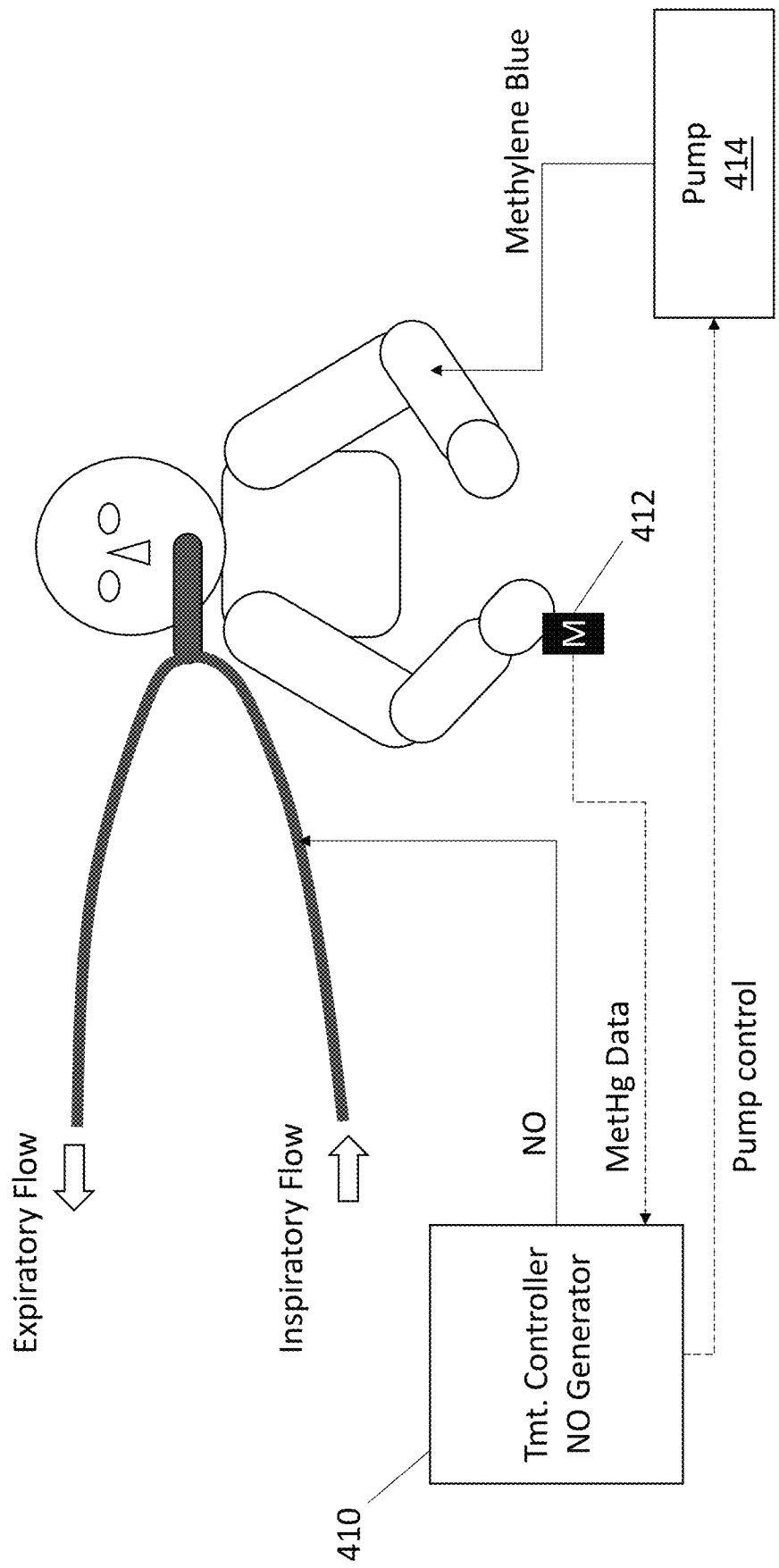
FIG. 34 is an exemplary embodiment of a NO system controller in conjunction with a pump for the delivery of a methemoglobin medication.

In some embodiments, as shown in FIG. 34, a controller 410 of the NO generation and/or delivery system can work in conjunction with methemoglobin medications to keep MetHg at an acceptable level. In some embodiments, a sensor 412 can be used to measure the MetHg level of the patient, and that information can be used by the controller 410 to either vary NO delivery, administer a methemoglobin medication to bring down the MetHg, or both. Various methods can be used to decrease the level of MetHG, including an injection, delivered manually or controlled by the controller of the NO system, or a can be administered orally to a patient. For example, as shown in FIG. 34, a pump 414 or other injection device, can be controlled by the controller 410 to deliver a methemoglobin medication, such as methylene blue, to the patient based on the measured MetHg by the sensor 412 and/or the amount of NO being delivered to the patient.

Treatment Control

Treatment Duration

In some embodiments, a user sets the duration of a NO treatment at the onset of treatment. The duration can be set using a variety of mechanisms, such as by a twisting the rotary knob of an analog timer, setting a digital timer, or selecting a treatment duration from a graphical user interface, for example. In some embodiments, there is a separate start button that initiates treatment. In some embodiments, when the treatment timer runs out, treatment can stop automatically. In some embodiments, an alarm is sounded at the end of the treatment timer and the treatment can stop manually, such as a user shutting down the treatment. In some embodiments, the NO generation system displays time remaining for the treatment.

Treatment End Point

In some embodiments, a NO generation device measures methemoglobin with a sensor or receives a patient methemoglobin measurement from an external device. As high dose NO is delivered, methemoglobin levels can rise. In some embodiments, when methemoglobin levels reach a threshold (e.g. 5%), a NO generation and/or delivery device can respond in one or more of the following ways: stop treatment, generate an alarm, lower the NO dose, and/or pause NO delivery until methemoglobin levels reduce below a second threshold. In some embodiments, the NO dose ramps and ramping ceases when methemoglobin levels reach a particular threshold and NO treatment continues at a constant concentration. In some embodiments, a NO generator displays a methemoglobin measurement on the user interface to inform the user. While the methemoglobin threshold can vary, in some embodiments, a methemoglobin threshold is between 1 and 7%. In some embodiments, resumption of treatment begins when methemoglobin levels drop below 2%. In some embodiments, the methemoglobin level and/or $SpO_2$ level are utilized as inputs into a closed-loop control scheme whereby the NO dose level is varied to do one or more of the following: maximize $SpO_2$, minimize methemoglobin levels, keep methemoglobin levels below a threshold.

Modes of Operation

NO Tank Mode

In some embodiments, a user selects a NO concentration and NO product gas flow rate and the system generates NO gas accordingly, independent of the patient treatment, relying on the user to set the device accurately and route the NO to the patient with appropriate levels of dilution, as applicable. This approach is equivalent to the NO generation device operating like a custom-concentration tank of NO with variable output flow rate.

Manual Mode

In some embodiments, a NO generation system operates in a manual mode, where the user enters the inspiratory flow rate and the desired NO dose, and the NO system produces the desired amount of NO. In some embodiments, the patient minute volume is entered as a value between 5 and 20 lpm in increments of 1-2 lpm. In some embodiments, the target NO level varies from 0.5 to 300 ppm NO. In some embodiments, the inspiratory flow rate is entered by one or more inputs for oxygen flow, air flow and other inspiratory flows. In some embodiments, the NO generation device determines the level of NO production required based on one or more user inputs, such as target NO dose, $O_2$ flow rate, and inspiratory flow rate. This approach provides a user with more controls than other modes and can provide perfect NO concentration dosing when used with an inline reservoir, such as a non-rebreather mask. NO generation is based on user inputs, however, resulting in shifts up or down in inhaled NO concentration related to high or low minute volume estimates provided by the user, respectively. When used in the absence of an inline reservoir for a variable flow treatment, such as CPAP or a ventilator, this approach can result in variable NO concentration over time within the inspiratory limb. NO variations can be acceptable when the minimum inhaled NO concentration is still effective. NO variations can also be acceptable when the system has been designed and deployed to prevent the patient from inhaling under-dosed gas that results from peak inspiratory flows.

Figure 7:
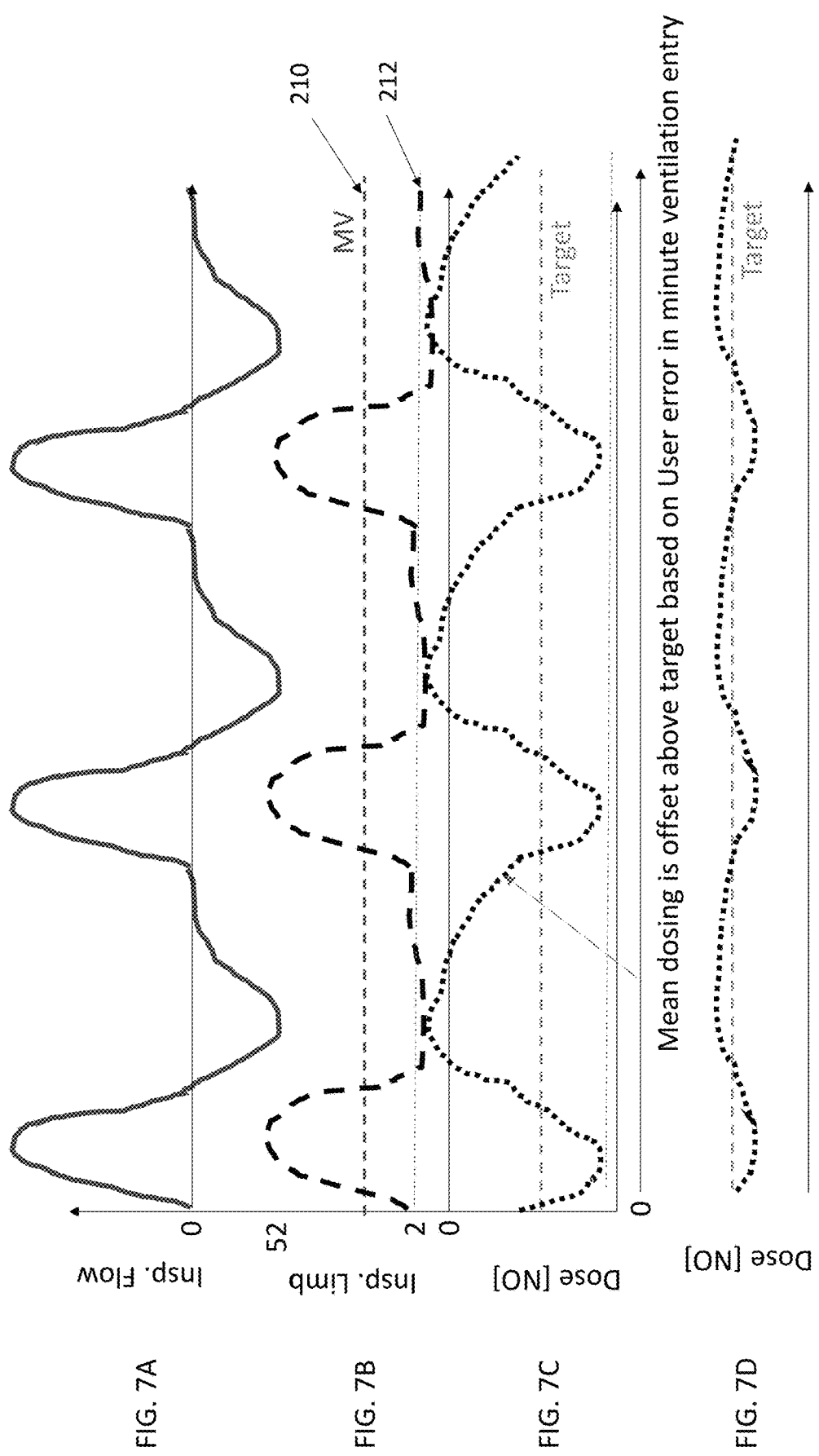
FIG. 7A, FIG. 7B, FIG. 7C, and FIG. 7D depict exemplary graphs showing the dosing performance for a NO generation system operating in manual mode.

FIG. 7A, FIG. 7B, FIG. 7C, and FIG. 7D depict an example of the dosing performance for a NO generation system operating in manual mode on a ventilator with bias flow. FIG. 7A depicts flow within a patient airway where inhalation is a positive value and exhalation is a negative value. FIG. 7B depicts flow within the inspiratory limb where peak flow matches inspiratory flows during inhalation and inspiratory limb flow equals a bias flow during exhalation. The minute volume 210 is the inhaled volume of gas for one minute. While the bias flow can vary, the bias flow 212 in this example is 2 lpm, as indicated in FIG. 7B. FIG. 7C shows a representation of the NO concentration within the inspired gas over time for a constant production NO generation system. NO concentration drops during inhalation and increases during exhalation as the NO generator overdoses the bias flow. In the depicted example, a user has manually input a patient minute volume that is greater than the actual patient minute volume. As a result, the NO generation device is generating more NO than if the user had input the correct minute volume. FIG. 7D depicts the inhaled NO concentration when a reservoir is used in the inspiratory limb to mix gases.

Automatic Mode

In some embodiments, a NO generation system measures the inspiratory flow rate and calculates the NO concentration and flow rate required to sufficiently dose the patient. In some embodiments, the NO generation system measures the inspiratory flow and the oxygen flow separately and calculates the NO concentration and flow rate required to sufficiently dose the patient. In some embodiments, a NO generation system measures the inspiratory flow and the user manually enters the oxygen flow and the device calculates the NO product rate required. These approaches result in similar NO concentration variations as manual mode but can reduce or eliminate the risk of erroneous user input for the patient minute volume. When used with an inspiratory line reservoir, such as a rebreather mask, this approach can deliver perfect NO dosing due to the accurate overall NO generation and mixing within the bag. One implementation detail of an inspiratory line reservoir approach is that the gas flow supplying the bag and the patient minute volume need to balance to prevent the reservoir from gradually increasing or decreasing over time due to mismatch in input flow and output flow. In one embodiment, an inspiratory line reservoir is purposely filled to beyond an expected patient tidal volume before a breath to ensure sufficient gas for inhalation. In that same embodiment, the inspiratory line reservoir is emptied to a consistent volume after patient inhalation and before reservoir filling to ensure a consistent datum for filling with each breath. In some embodiments, that datum is a volume of zero ml of gas within the reservoir. In some embodiments, excess gas that is removed from the reservoir in this way is scrubbed prior to release to atmosphere to remove NO and $NO_2$ from the gas.

Figure 8:
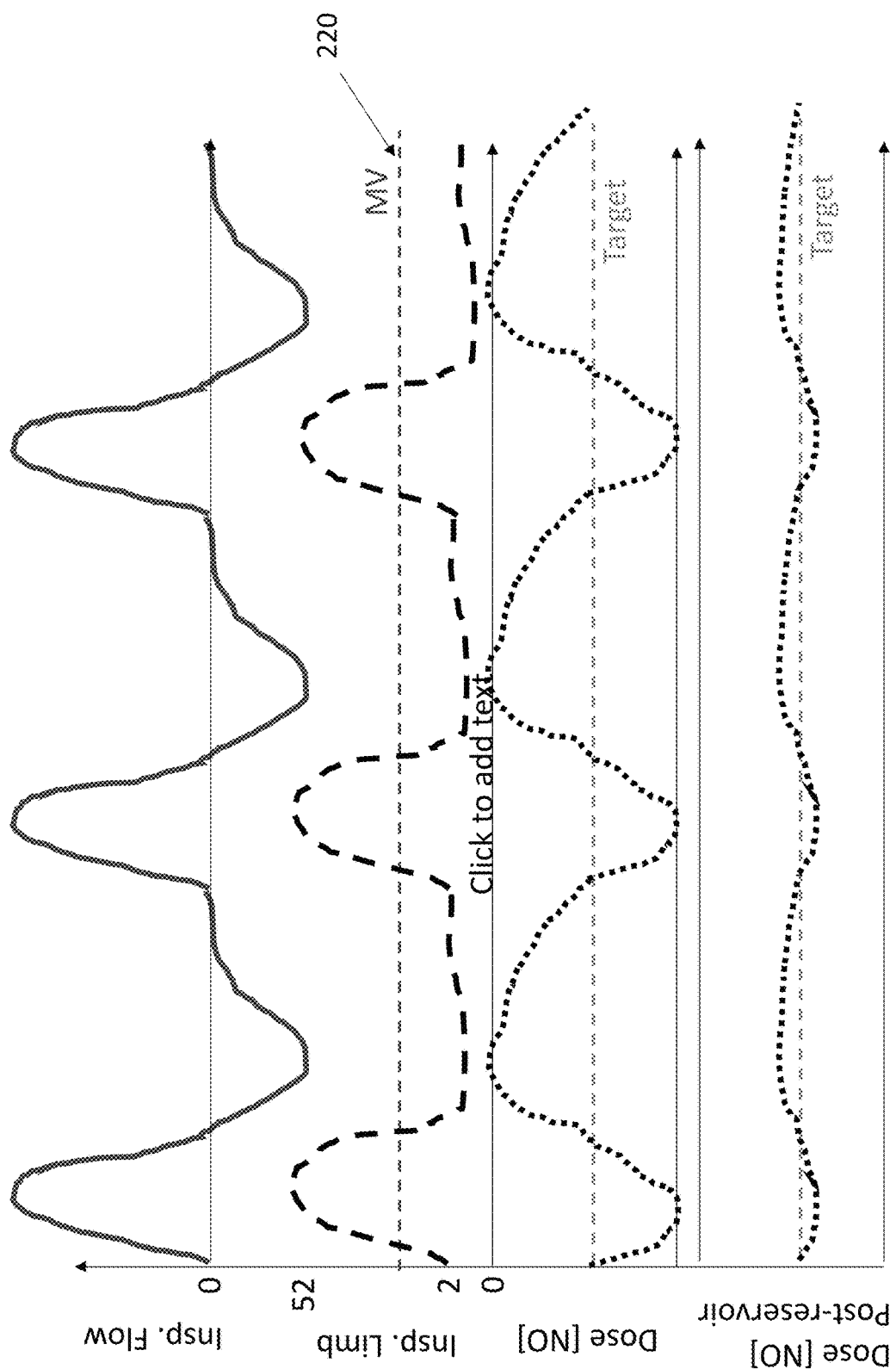
FIG. 8A, FIG. 8B, FIG. 8C, and FIG. 8D depict exemplary graphs showing the NO dose accuracy of a constant production NO device operating in automatic mode.

FIG. 8A, FIG. 8B, FIG. 8C, and FIG. 8D depict the NO dose accuracy of a constant production NO device operating in automatic mode. The curves are similar to those in FIG. 7A, FIG. 7B, FIG. 7C, and FIG. 7D, except that the amount of NO generated is based on the actual minute volume 220 measured by the device instead of a user-input value resulting in the average dose being closer to target. This approach can respond to changes in the patient minute volume automatically. FIG. 7D and FIG. 8D depict the inhaled NO concentration when a reservoir is used in the inspiratory limb to mix gases resulting in a more homogeneous mixture of NO in inspiratory gas over time and less variation in concentration.

External Input Mode

In some embodiments, a NO generator receives patient inspiratory flow information from a separate treatment device, such as a ventilator or CPAP machine and generates NO in sufficient quantity to maintain a user-selected inspired NO concentration. Flow information can include many parameters related to the inspiratory flow, bias flow, including inspiratory pressure, oxygen levels, flow rates, and breath timing information.

Fixed Production Device

In some embodiments, a NO generation system is designed to deliver a specific concentration of NO at a specific flow rate (i.e. fixed NO production). This solution can be useful in its simplicity and treatment consistency. In some embodiments, a NO generation system is configured to generate a constant quantity of NO, leaving the responsibility of diluting the NO to inhaled concentrations to the user.

Fixed Inhaled Concentration Device

In some embodiments, a NO generation system is designed to deliver an appropriate amount of NO to achieve a single inhaled NO concentration at a range of flow rates. In some embodiments, the concentration of NO product gas is held constant and the flow rate of product gas entering the inspiratory flow varies proportionally with the inspiratory flow. This results in constant dilution ratio (merged inspiratory flow+NO product gas flow:NO product gas flow). It follows that the NO product gas concentration is equal to the mathematical product of the dilution ratio and the target inhaled concentration. This approach results in tighter inhaled concentration control which can be advantageous when a particular narrow range of NO concentrations are considered therapeutic and/or safe and results in greater treatment to treatment consistency. As the target inhaled NO concentration increases, it gets closer to the NO concentration safety limit, narrowing the acceptable range of NO concentrations and requiring tighter concentration control for safety.

Bias Flow Dosing Device

In some embodiments, a NO generation device generates NO at a constant rate sufficient to accurately dose the bias flow during a patient inspiratory cycle. In some embodiments, the bias flow rate is entered by the user. In some embodiments, the bias flow rate is measured by the NO generation device. In some embodiments, the bias flow rate is provided by an external device.

Figure 9:
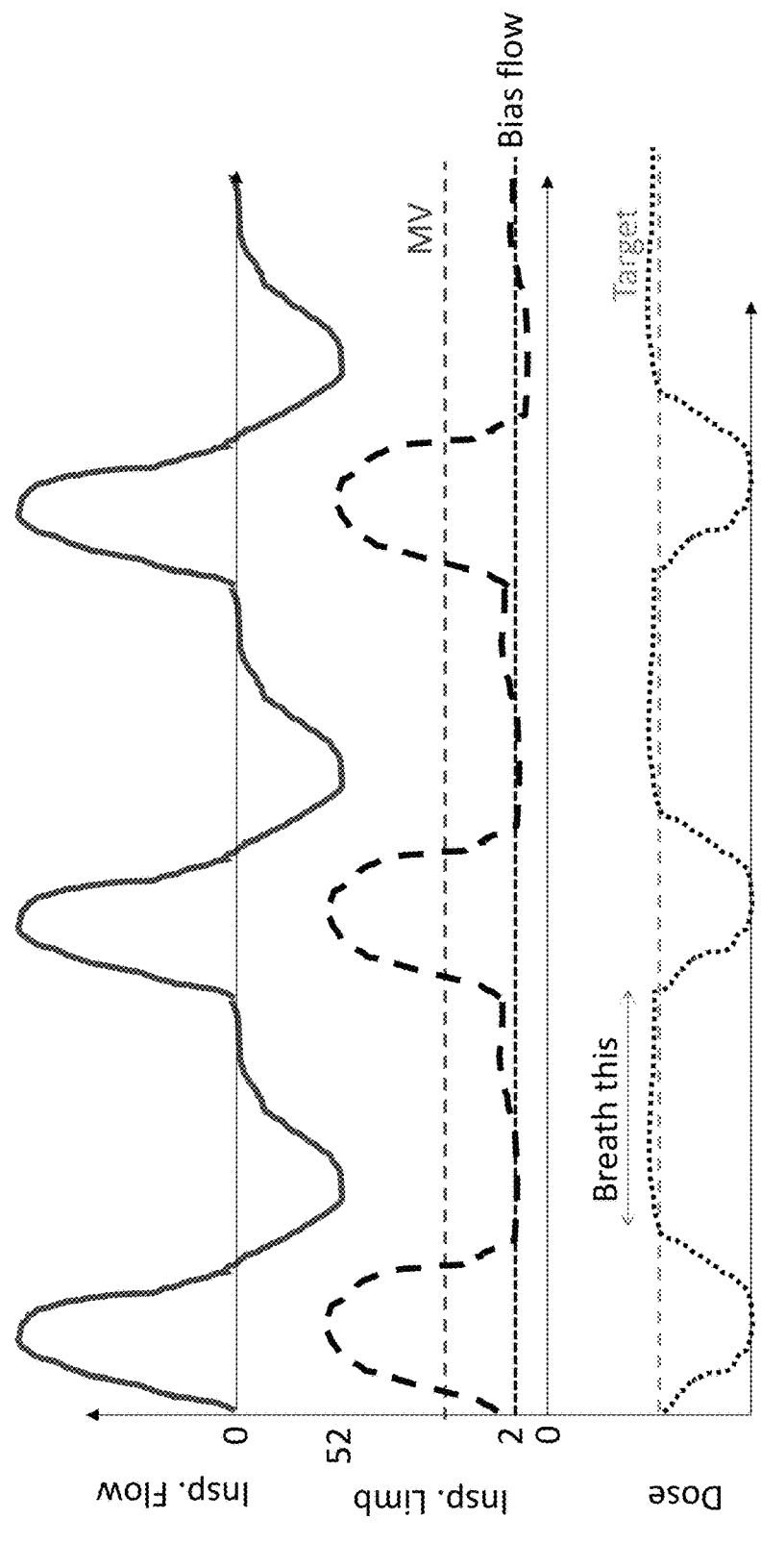
FIG. 9A, FIG. 9B, and FIG. 9C depict exemplary graphs showing inspired concentrations of a system that doses the bias flow.

NO is generated to accurately dose the bias flow with the understanding that inspiratory peak flows will be underdosed. FIG. 9A, FIG. 9B, and FIG. 9C depict the inspired concentrations of a system that doses the bias flow. FIG. 9A shows the inspiratory flow rate. FIG. 9B shows the inspiratory limb flow with bias flow. FIG. 9C shows the NO concentration within the inspiratory limb. So long as the patient breaths the gas generated during the bias flow, the patient will be accurately dosed. This approach requires a combination of bias flow and inspiratory limb volume that are sufficient to generate a column of homogeneous concentration NO within the inspiratory limb for inspiration prior to each breath. When used with a rebreather bag, this approach can result in underdosing since the system is actually making less NO overall. Making less NO overall can require less power to generate less NO, notably in battery-powered applications.

In some embodiments, the delivered patient dose can be varied intentionally by varying one or more of the length of the inspiratory limb and the flow rate in the inspiratory limb to change the phase relationship between inspiration and the timing of the low concentration volume of gas within the inspiratory limb.

In some embodiments, users of a NO generation and/or delivery device can treat themselves with nitric oxide. In one example, a caregiver can prophylactically self-treat with nitric oxide prior to leaving home in the morning and when they return home in the evening. In one embodiment, NO is either delivered to or generated by a face mask that the User wears during treatment. In some embodiments, NO is generated in air that the patient inhales through a tube, like an inhaler. In some embodiments, the NO generation and/or delivery device has an alarm that reminds the user when it is time to treat. A NO generation and/or delivery device can include wireless and wired connectivity to external devices and the Cloud for monitoring device function, monitoring device use, reminding the user to use the device, providing the user with data related to the treatments and other information. In some embodiments, the NO generation device reports to researchers the level of device use during a clinical trial to enable an assessment of patient compliance with a clinical protocol.

It should be clear that the invention is not limited to the modes of operation listed above and that some embodiments comprise combinations of these concepts.

Nitric Oxide Mask

Design

In some embodiments, it can be important for health care providers to be able to sterilize the air that they inhale. This can protect the user from airborne infectious microbes. A mask can also be used to filter exhaled gas for the safety of nearby people.

Various concentrations of inhaled NO can be used to prevent microbial infection. In some embodiments, the use of inhaled NO at concentrations ranging from about 100 ppb to 159 ppm can be used to prevent infection with microbes including viruses, bacteria, fungi, and mycobacteria. In some embodiments, inhaled concentrations up to 300 ppm may be delivered for short exposures. In some embodiments, inhaled concentrations in ranges from about 50 ppm-155 ppm, 50 ppm-200 ppm, 50 ppm-300 ppm may be delivered. In some embodiments, inhaled concentrations exceeding 300 ppm are delivered every nth breath to expose infectious materials to high doses while minimizing the risk of methemoglobinemia.

In some embodiments, the inhaled NO prevents infection or reduces the infective dose of the microbe resulting in a milder illness.

The users of the inhaled NO can include a variety of users, such as health care professionals (e.g. physicians, and nurses), or other professionals or individuals at risk for infections (e.g. family members of an infected host).

The inhaled NO can be administered in a variety of ways. In some embodiments, inhaled NO is administered continuously. In some embodiments, inhaled NO is administered intermittently. For example, the inhaled NO can be delivered twice a day, three times a day, or up to 10 times a day to prevent infections.

In some embodiments, the inhaled NO is delivered in a pulsed manner by sensing inspiratory effort. In some embodiments, the inhaled NO is delivered every nth breath. In some embodiments, the inhaled NO is delivered to a breath according to a timing schedule (every nth minute.

In some embodiments, the inhaled NO is delivered continuously without pulsing.

In some embodiments, the inhaled NO is given for days to months to years.

In some embodiments, the inhaled NO is delivered into a nasal cannula, a facemask, or a whole facemask.

In some embodiments, an oronasal mask can be used to remove infectious particles from the inhaled air. This can be used when the nitric oxide is generated from a stationary or a portable electrical NO generator or from another course.

In some embodiments, the facemask or the nasal cannula itself incorporates an electrical NO generator.

Architecture

System Design

Figure 10:
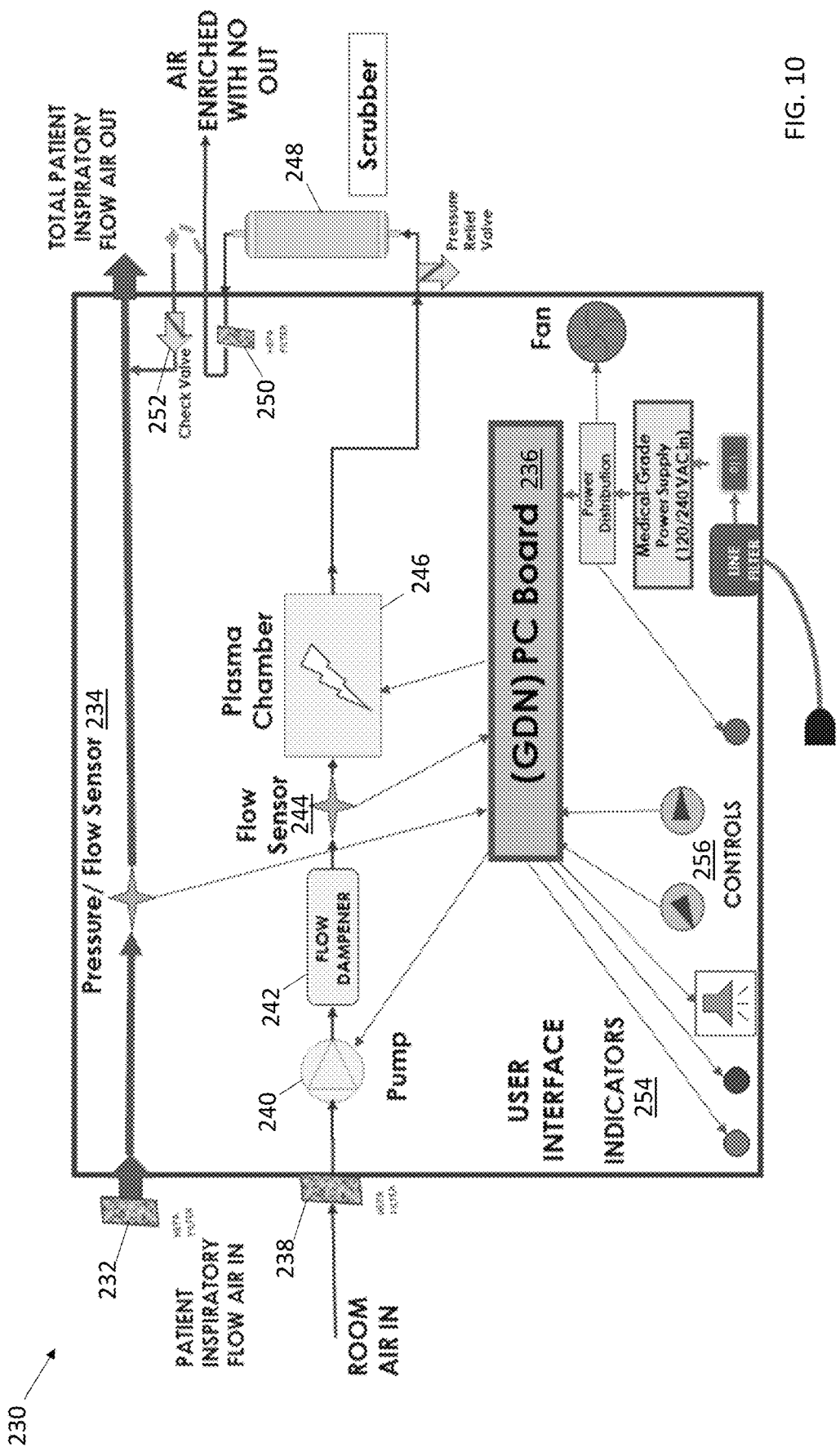
FIG. 10 illustrates an embodiment of a NO generation device.

An exemplary NO generation device 230 is depicted in FIG. 10. As shown in FIG. 10, patient inspiratory air enters the system through a filter 232. The inspiratory flow passes through a pressure/flow sensor 234 connected to the device controller 236 (Generate & Deliver NO, or GDN, board). The inspiratory flow can be from a multitude of sources, including but not limited to house air, a gas cylinder, a ventilator, or a CPAP device. In some embodiments, a patient draws air through a NO device using the inspiratory forces of their diaphragm.

Reactant gas enters this exemplary system (room air in), passing through a filter 238. Other reactant gas conditioning steps are possible (not shown), including but not limited to VOC removal, NOx removal, liquid water removal, water vapor removal, etc. A pump 240 pressurizes the reactant gas and a flow dampener 242 removes some or all of the pressure and flow pulsations from the pump in the reactant gas. Flow dampening improves the accuracy of the reactant gas flow measurement and provides more stable pressure and flow within the plasma chamber for improved NO production consistency. After flowing through a reactant gas flow sensor 244, reactant gas flows into a plasma chamber 246.

Within the plasma chamber are one or more pairs of electrodes. Electrodes can be of many types including but not limited to gliding arc, opposed, parallel, torch, gliding torch, triple electrodes, dielectric barrier, microwave and other types. NO is generated within the plasma chamber when energy in the form of high voltage or RF energy is applied to the electrodes to a level that induces breakdown in the reactant gas between the electrodes. NO-containing product gas passes through a scrubber 248, a filter 250, and a check valve 252 prior to being introduced to the inspiratory flow. In some embodiments, a filter is also located upstream of the scrubber to prevent migration of scrubber media and capture particulate from the electrodes. The check valve ensures unidirectional flow from the NO device into the inspiratory flow with no losses of inspiratory flow. In some embodiments, multiple plasma chambers and/or multiple electrode gaps are utilized simultaneously to generate a target amount of NO.

As shown in FIG. 10, NO gas can be injected into the inspiratory flow at the controller or remain independent of the inspiratory flow as "air enriched by NO." In some embodiments, NO is introduced to the inspiratory flow as soon as possible. This allows for the rapid dilution of the NO, thereby decreasing the rate of NO oxidation into $NO_2$. In some embodiments, the NO-enriched air can be kept separate from inspiratory gases until a point closer to the patient. This can be beneficial in applications of elevated inspired oxygen levels since it reduces the exposure time of NO to high concentration oxygen. In summary, the location for NO injection is related to one or more of the inspiratory oxygen concentration, the reactant gas oxygen concentration, the volume of the delivery path between NO device and the patient, the flow rates of inspiratory gas and NO gas to the patient, the transit time of the NO gas, the NO concentration, and the temperature and pressure of the gases.

Additional features of the system depicted in FIG. 10 include a user interface with indicators 254 for NO treatment, alarms, and warnings. Manual user controls 256 are shown for entering inspiratory flow rate and target inspired NO concentration. The device is powered by AC power that enters the system through a line filter, a medical grade power supply and power distribution circuit. A fan is used to draw air through the device enclosure to keep the internal components at acceptable temperature levels. An illuminated indicator indicates that power is on. In some embodiments (not shown), the system includes batteries to provide energy during a power outage and/or patient transport.

A pressure relief valve between the plasma chamber and scrubber protects the system from over-pressurization resulting from a clogged scrubber, kinked line, clogged filter, failed check valve and excessive inspiratory pressure. In some embodiments, a NOx scrubber is located after the pressure relief valve to scrub product gas before release into the atmosphere. In some embodiments, a pressure relief valve is instrumented with a position sensor, pressure sensor, flow sensor, or other type of transducer that can inform the NO device controller that the valve has been actuated. In some embodiments, a NO device controller monitors the pressure within the NO generation system. In some embodiments, a NO controller ceases reactant gas flow and/or plasma activity when an over-pressure event is detected. In some embodiments, a NO controller generates an audible and/or visual alarm when an over-pressure event occurs.

Figure 11:
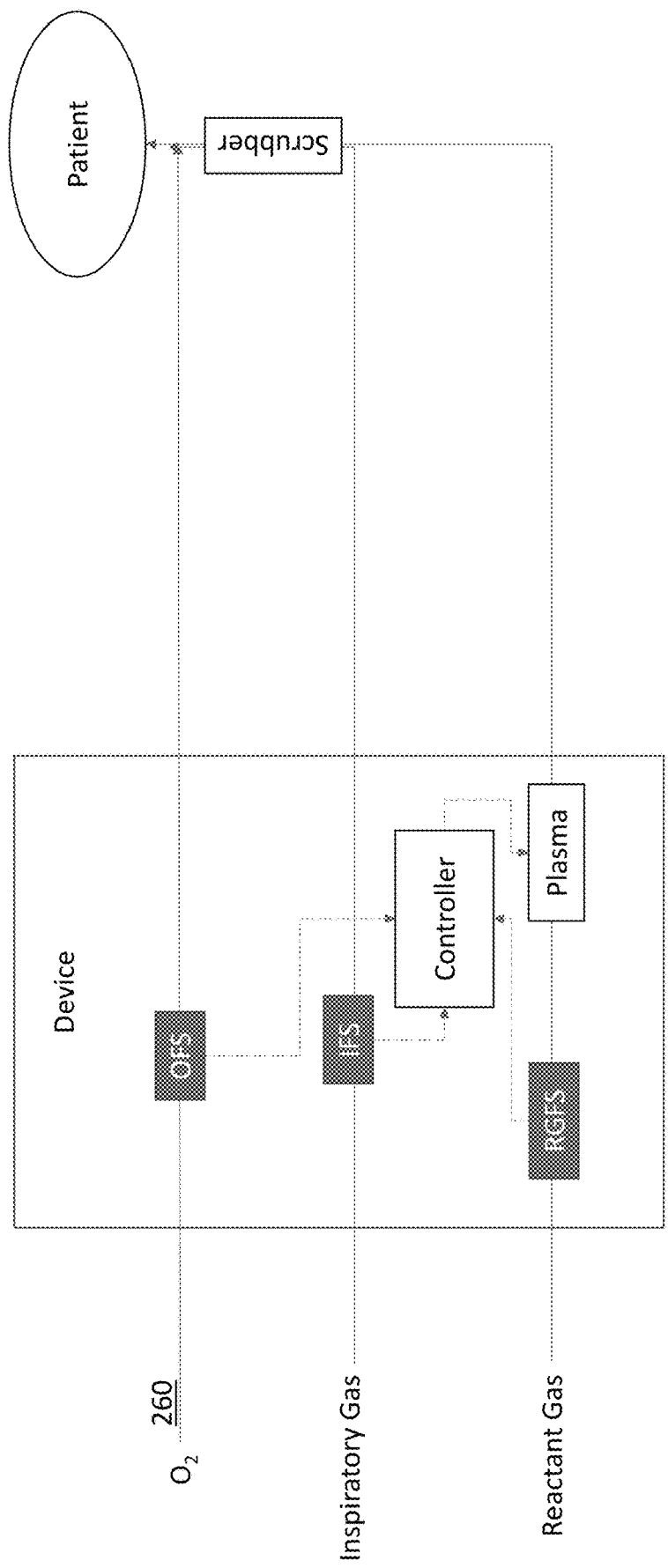
FIG. 11 illustrates an embodiment of a NO generation device.

FIG. 11 depicts a similar system to the one shown in FIG. 10 with the addition of an oxygen flow path 260 through the system. The controller uses a flow and/or pressure sensor to detect oxygen flow. In some embodiments, the measured oxygen flow is added to the inspiratory flow to determine a total inspiratory flow. In some embodiments, NO production is a function of the total inspiratory flow to ensure accurate inspired NO concentration.

In the depicted embodiment, reactant gas is provided from a pressurized source so that no internal pump is required. The scrubber is located within the inspiratory limb, after blending of inspiratory gas and NO containing gas. Oxygen is added last to minimize NO production. In some embodiments, NO gas is scrubbed of $NO_2$ prior to merging with either the inspiratory gas flow or the oxygen gas flow.

Flow Sensors

Flow sensors can be located within the enclosure of the NO generation device, with inspiratory, oxygen and other gases flowing through the NO generation device. Various types of flow sensors can be utilized (e.g. delta-pressure, hot wire, pressure anemometer, ultrasonic, paddle wheel, positive displacement, mass flow, etc.). In some embodiments, pressure, temperature, humidity, and volumetric flow rate are measured and utilized to determine a mass flow rate. In some embodiments, gases are blended within the NO generation device. In some embodiments, gases pass through the NO generation device for measurement purposes but only merge at or near the patient. This approach can help to minimize $NO_2$ formation, for example in cases with elevated inspired oxygen levels, by mixing NO with oxygen as late as possible before patient delivery.

Alternatively, flow sensors can be located remotely from the NO generation device. In some embodiments, separate flow sensors measure oxygen flow to a patient in an oxygen line and the rate of medical air in another line. In some embodiments, external flow sensors connect to the NO generation device wirelessly. In some embodiments, wired connections exist. In some embodiments, a custom tubing set is used for treatments that includes embedded wires for sensor communications. This decreases user-steps and improves system reliability by decreasing the quantity of cables that could be tangled or pulled during treatment.

System Components

Reactant Gas Source

Reactant gas for NO generation can be sourced from house compressed air, a gas cylinder, or ambient air. In some embodiments, separate $O_2$ and $N_2$ tanks are used.

Reactant Gas Filter

Reactant gas can be filtered prior to entering the system. In some embodiments, reactant gas is filtered to 20 microns. In some embodiments, it is filtered to 0.22 micron.

Reactant Gas Scrubber

NO generators that utilize ambient air for reactant gas benefit from purifying the air prior to sending reactant gas through the plasma chamber. This approach decreases the number of compounds that can be created in the plasma chamber and decreases the potential of deposition of solids within the plasma chamber from solid compounds formed plasma chemistry. In some embodiments, reactant gas is scrubbed for VOCs, formaldehyde, ammonia, chloromethane, bleach and other compounds prior to entering the plasma chamber. Reactant gas scrubbers can be constructed of one or more of activated carbon, potassium permanganate, sodium metabisulfite (for formaldehyde), soda lime, acid (e.g. sulfuric acid for ammonia), and other compounds. In some embodiments the scrubber materials are mixed in a single scrubbing unit. In other embodiments, there is a series of scrubbers that the reactant gas passes through to prevent cross-scrubber chemical reactions. For example, acid scrubbers and alkaline scrubbers (soda lime) are separate to prevent reactions.

Reactant Gas Humidity Management

NO generators also can remove some or all of the water content within the reactant gas prior to flowing through the plasma chamber. This reduces the potential of water condensation within the system and makes the plasma chamber inputs more consistent for predictable NO generation.

Gas Flow

Reactant gas flow through a high concentration NO generation device can be the result of a pressure gradient across the device or propelled by a pump. In some embodiments, the NO generation device receives a NO target concentration value from a user, measures the inspiratory gas flow rate and determines an appropriate NO generation level (concentration*flow) accordingly. In some embodiments, a NO generation device is designed to only make one concentration of NO. In some embodiments, a NO generation device operates at a constant flow rate and NO production level. In some embodiments, a NO generation device produces 1500 ppm NO at 10 lpm and relies on the user to plumb the NO into a delivery device.

In some embodiments, part or all of the inspiratory flow serves as reactant gas for the NO generator. This approach is effective for prophylactic treatment of care providers that do not require additional oxygen because the patient is seemingly healthy and can breathe normally. This approach can also work in cases where supplemental oxygen is utilized. In some embodiments, the user provides the $O_2$ concentration within the reactant gas to the NO generation device. In some embodiments, the NO generation device measures the $O_2$ concentration of reactant gas. In embodiments where reactant gas oxygen levels can vary, a NO generation system includes a look-up table or formula to determine plasma parameters required to generate a known quantity of NO. Plasma parameters include, for example, energy, voltage, current, duty cycle, frequency, AC waveform, dithering, etc.

Pressure Relief Valve

In some embodiments, a pressure relief valve is included within the system to protect the system from a downstream obstruction. A pressure relief valve can prevent damage to the scrubber, plasma chamber and other parts of the system. Obstructions can occur due to a myriad of scenarios, including but not limited to a kinked line, a clogged scrubber, failed valve, blocked injector or other issues. When a pressure relief valve is located after the plasma chamber, gas relieved by the valve can contain some level of NO and $NO_2$. In some embodiments, a $NO_2$ and/or NOx scrubber is located in the exhaust path of a pressure relief valve to clean exhausted gas prior to release into the environment.

In some embodiments, a pressure relief valve is included within an inspiratory limb. This can prevent a NO generation system from over-pressurizing the lungs of a patient. In some embodiments, a NO generator includes a pressure sensor that measures inspiratory limb pressure. In some embodiments, a NO generation system ceases delivery of NO to an inspiratory limb when inspiratory limb pressure exceeds a threshold.

Product Gas Scrubber

The process of NO generation also produces $NO_2$. $NO_2$ can be chemically scrubbed from the NO product gas using soda lime, for example. In some embodiments, the scrubber material is packaged in a user-replaceable cartridge. In some embodiments, a scrubber cartridge contains 36 g of soda lime that provides a system with more than 16 hours of treatment at 200 ppm NO in 20 lpm.

Figure 12:
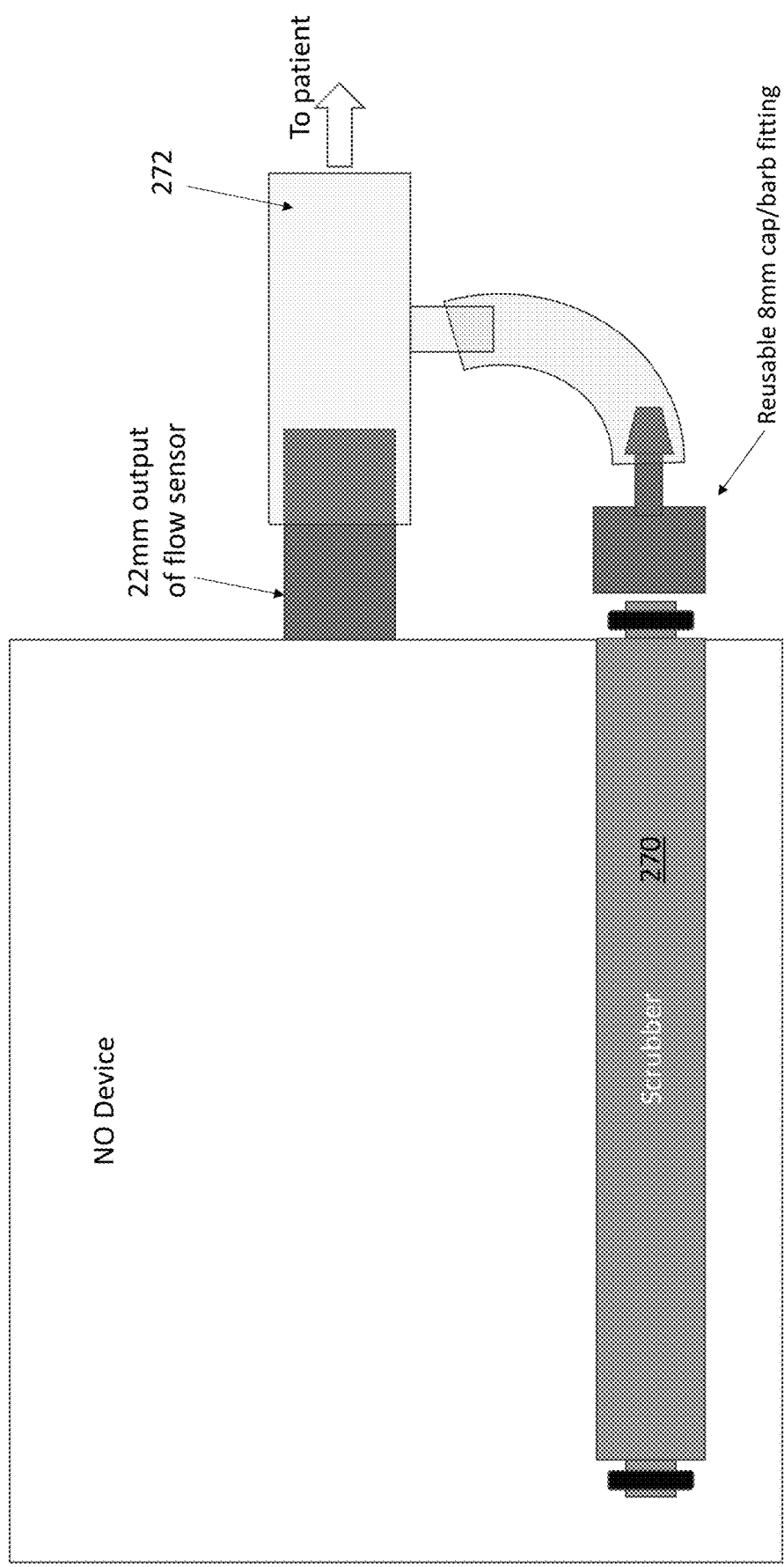
FIG. 12 illustrates an embodiment of a product gas scrubber.

FIG. 12 depicts an embodiment of a product gas scrubber. A scrubber 270 includes an enclosure containing scrubber media and/or sheet material and/or coatings. In some embodiments, the scrubber is removably inserted into the device enclosure with one or more seals ensuring a leak-free pneumatic connection. The seal can be comprised of one or more sealing methods such o-rings, lip-seals, compression seals, or other means. In some embodiments, the raw, unpackaged scrubber material in the form of granules, sheets, coils of sheets, and/or stacks of sheets is replaced alone, thereby reducing waste and weight. In the depicted embodiment, inspiratory flow exits the device enclosure and flows into a tee fitting 272 (for example, a 22 mm tee fitting). One of the legs of the tee fitting is connected to the scrubber while the other leg of the tee directs flow to the patient. In the depicted embodiment, the tee fitting tube connects to the scrubber with an O-ring seal to facilitate establishment and removal of the pneumatic connection to the scrubber. In the depicted design, the inspiratory flow output is a standard 22 mm tapered breathing circuit connection.

Figure 13:
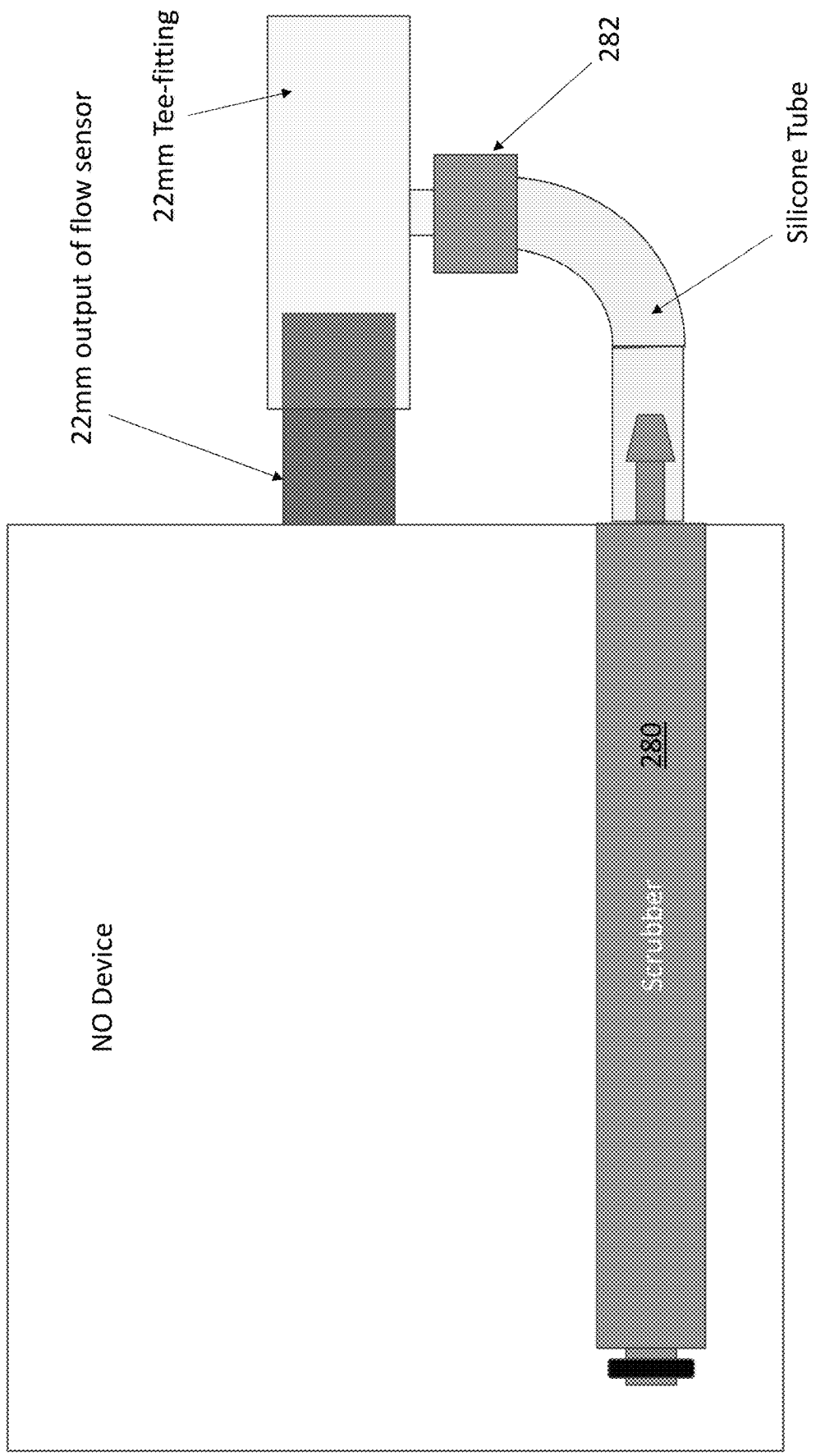
FIG. 13 illustrates an embodiment of a NO generator scrubber.

FIG. 13 depicts an embodiment of a NO generator scrubber design where the scrubber assembly 280 includes a tube for delivery of NO to the inspiratory flow. A luer fitting 282 is shown connecting the scrubber tube to the T-fitting. In other embodiments, an O-ring, compression fitting, and/or barb connection is used.

Inhaled Gas Scrubber

Figure 14:
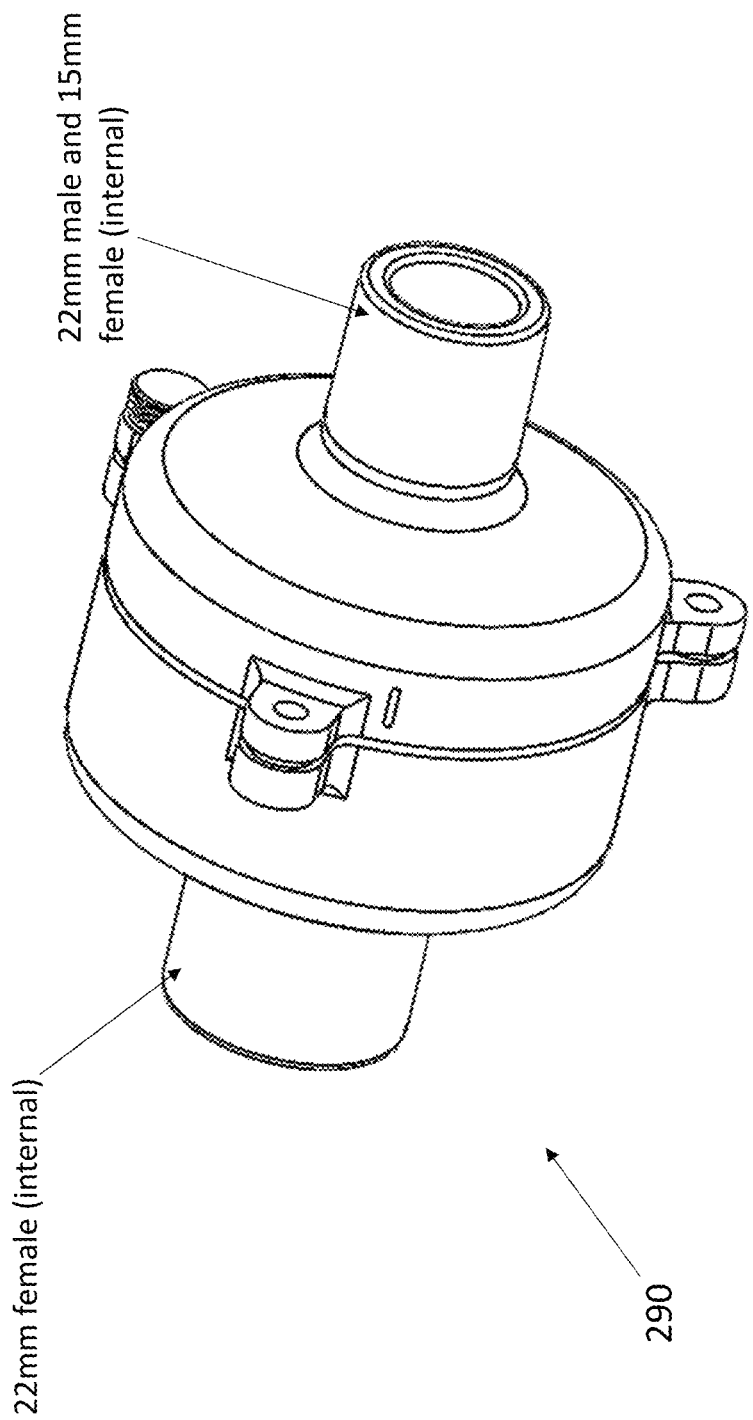
FIG. 14 shows an exemplary inspiratory gas scrubber.
Figure 15:
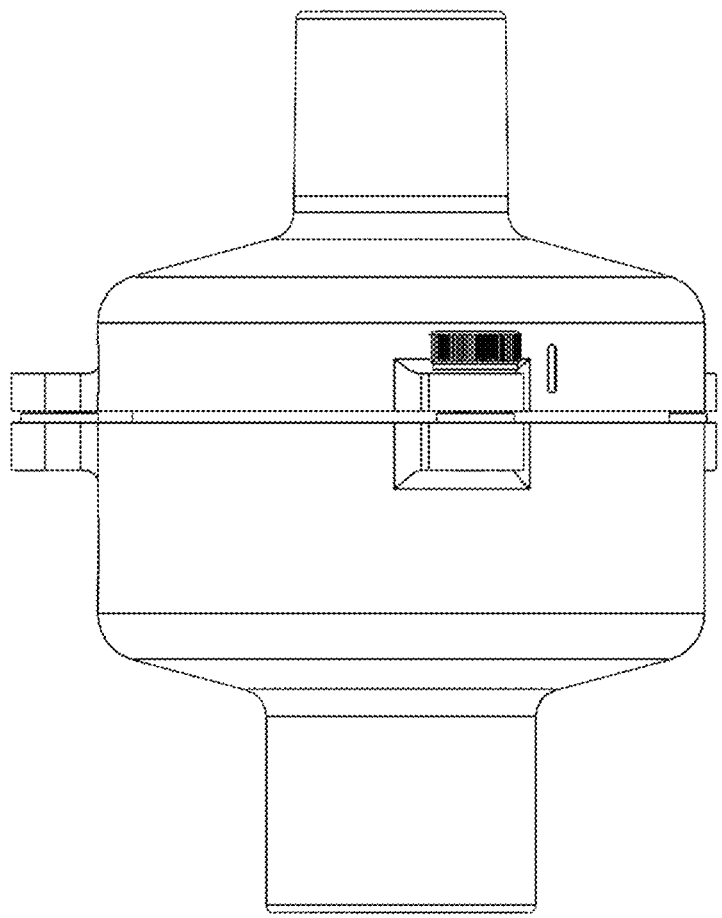
FIG. 15 shows a side view of the scrubber of FIG. 14.

In some embodiments, inspiratory flows of gas are scrubbed for $NO_2$ prior to inhalation. FIG. 14 shows an exemplary inspiratory gas scrubber 290 with 22 mm fittings on either end (for example, a 22 mm female internal connection, and a 22 mm male and 15 mm female internal connection). Two halves of the housing are held together with thumb screws to maintain an air-tight seal. The scrubber housing is filled with scrubber material, such as soda lime, lithium hydroxide, or other $NO_2$ scrubber materials. The scrubber material can be in particle, foam, coating and/or sheet form. In some embodiments, coiled sheet material is utilized. In other embodiments, stacked flat sheets of sheet material are utilized. In some embodiments, the sheet material is flat on both sides and is spaced by an additional material. In some embodiments, the sheet material includes a geometry in the $3^{rd}$ dimension that spaces the sheets apart, permitting gas flow between the layers. In some embodiments, the sheets are sinusoidal wave-shaped. In some embodiments, the sheets have posts or ridges that protrude from the surface and provide gas flow pathways. FIG. 15 is a side view of the scrubber of FIG. 14 showing the thumb screw connections.

In some embodiments, filter material is located within the inhaled gas scrubber assembly after the scrubber material to remove scrubber material particles from the inspiratory gas material. In some embodiments, a separate filter component is connected to the inspiratory gas scrubber by either the patient or clinical user.

Figure 16:
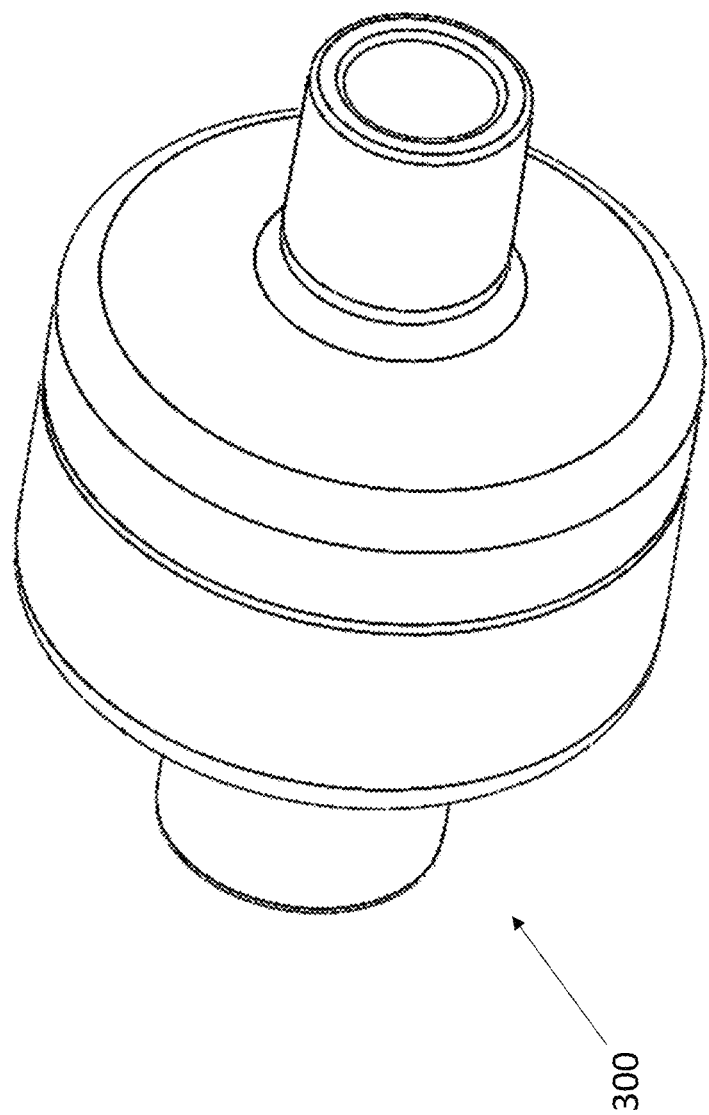
FIG. 16 shows an embodiment of a single-use inspiratory gas scrubber.

FIG. 16 is an embodiment of an inspiratory gas scrubber 300 that is single use. The sides are flush because the design has been sealed in a more permanent fashion, such as by ultrasonic welding, spin welding, thermal bonding or adhesive.

Figure 17:
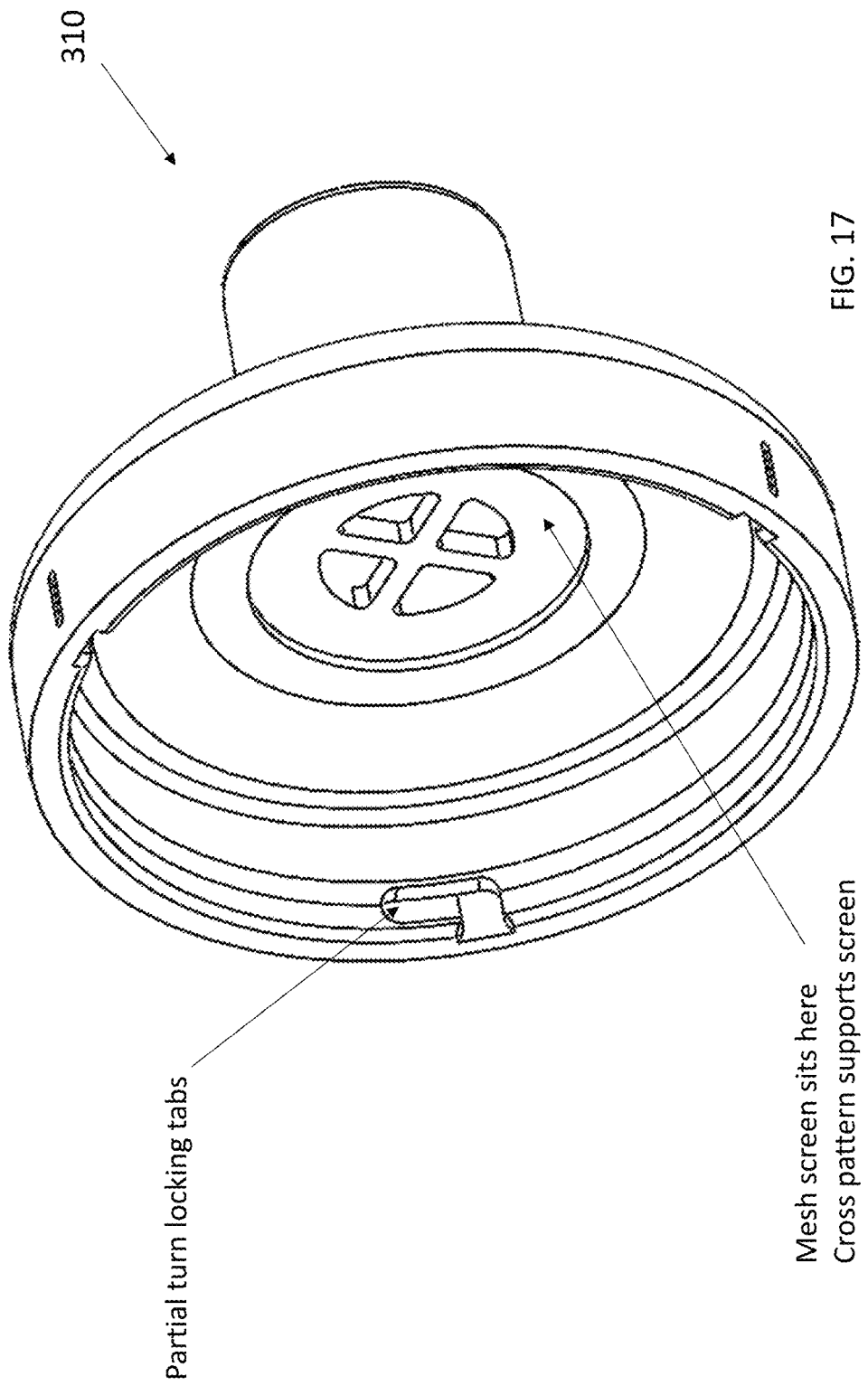
FIG. 17 shows an embodiment of inspiratory gas scrubber design that threads together.
Figure 18:
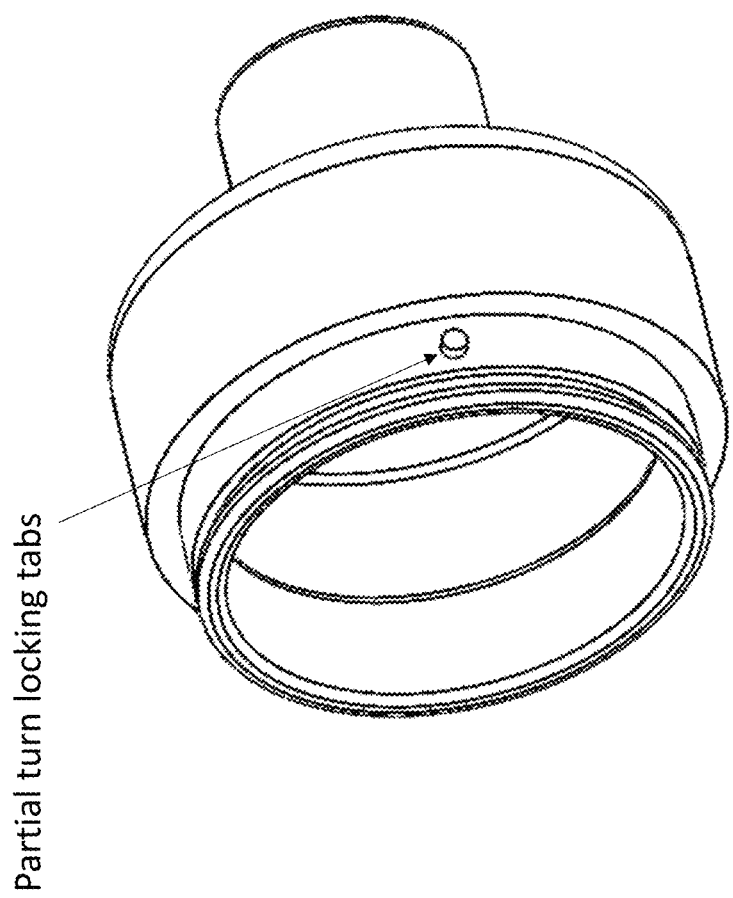
FIG. 18 shows an embodiment of a mating side to the scrubber housing end of FIG. 17.

FIG. 17 depicts an exemplary inspiratory gas scrubber 310 that threads together. A mesh of material in the pneumatic pathway prevents migration of scrubber material into other parts of the system. FIG. 18 depicts the mating side to the scrubber housing end depicted in FIG. 17.

Figure 19:
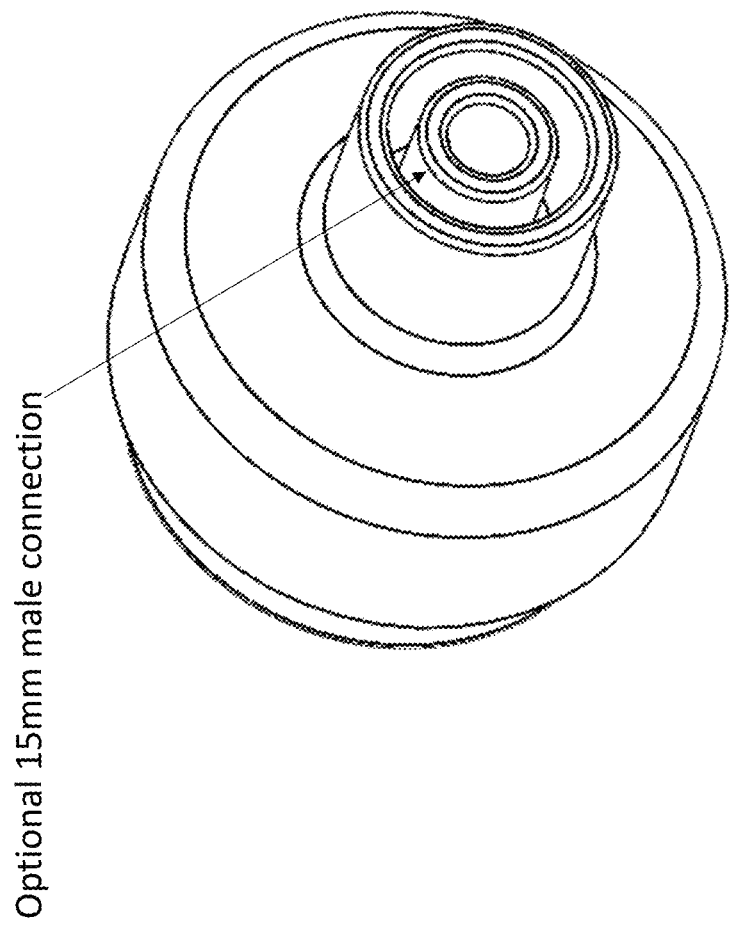
FIG. 19 illustrates an embodiment of a pneumatic connection to an inspiratory line scrubber.

FIG. 19 depicts a pneumatic connection to the inspiratory line scrubber that can accept connections from either a 22 mm (adult) ventilator tube or a 15 mm (pediatric) ventilator tube due to the concentric conical connections.

Figure 21:
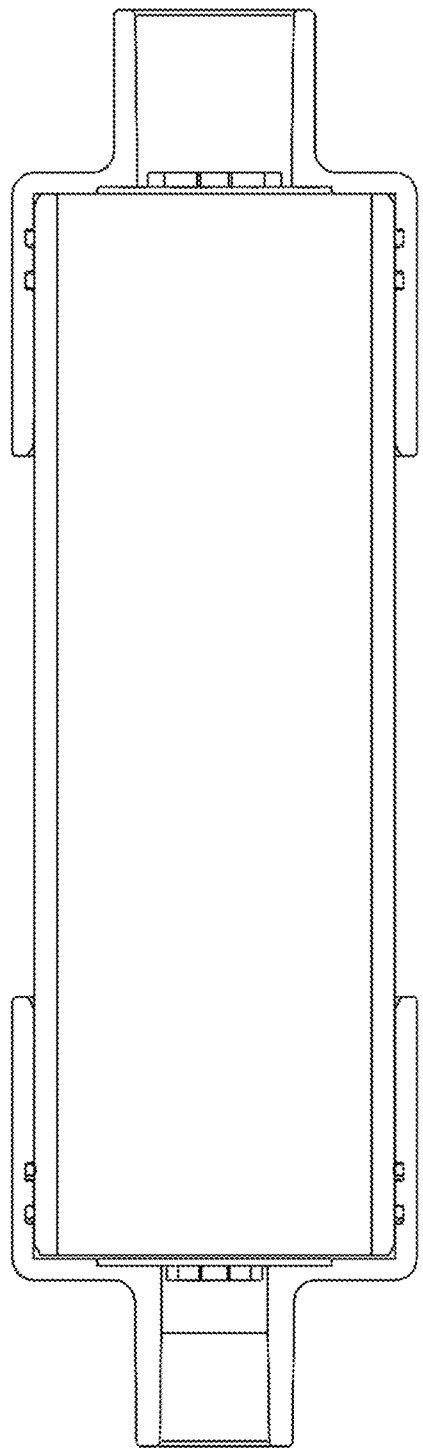
FIG. 21 illustrates a cross-sectional view of the tubular inspiratory gas scrubber shown in FIG. 17.
Figure 22:
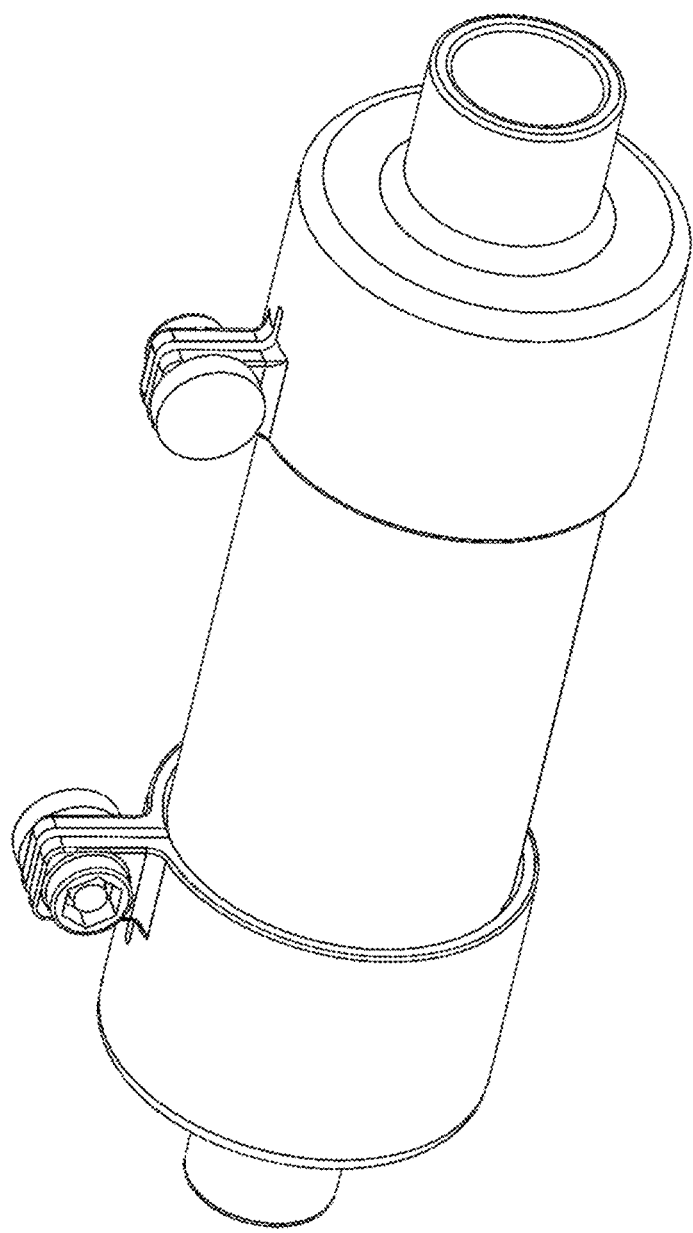
FIG. 22 illustrates a perspective view of the tubular inspiratory gas scrubber shown in FIG. 17.

FIG. 20 depicts an exemplary scrubber 320 comprised of tubing and end fittings. O-ring seals between the caps and the tube prevent losses of NO product gas. The assembly can include filter material before and/or after the scrubber material to capture particulates from the scrubber material and electrodes. FIG. 21 and FIG. 22 show additional views of a tubular inspiratory gas scrubber.

Figure 23:
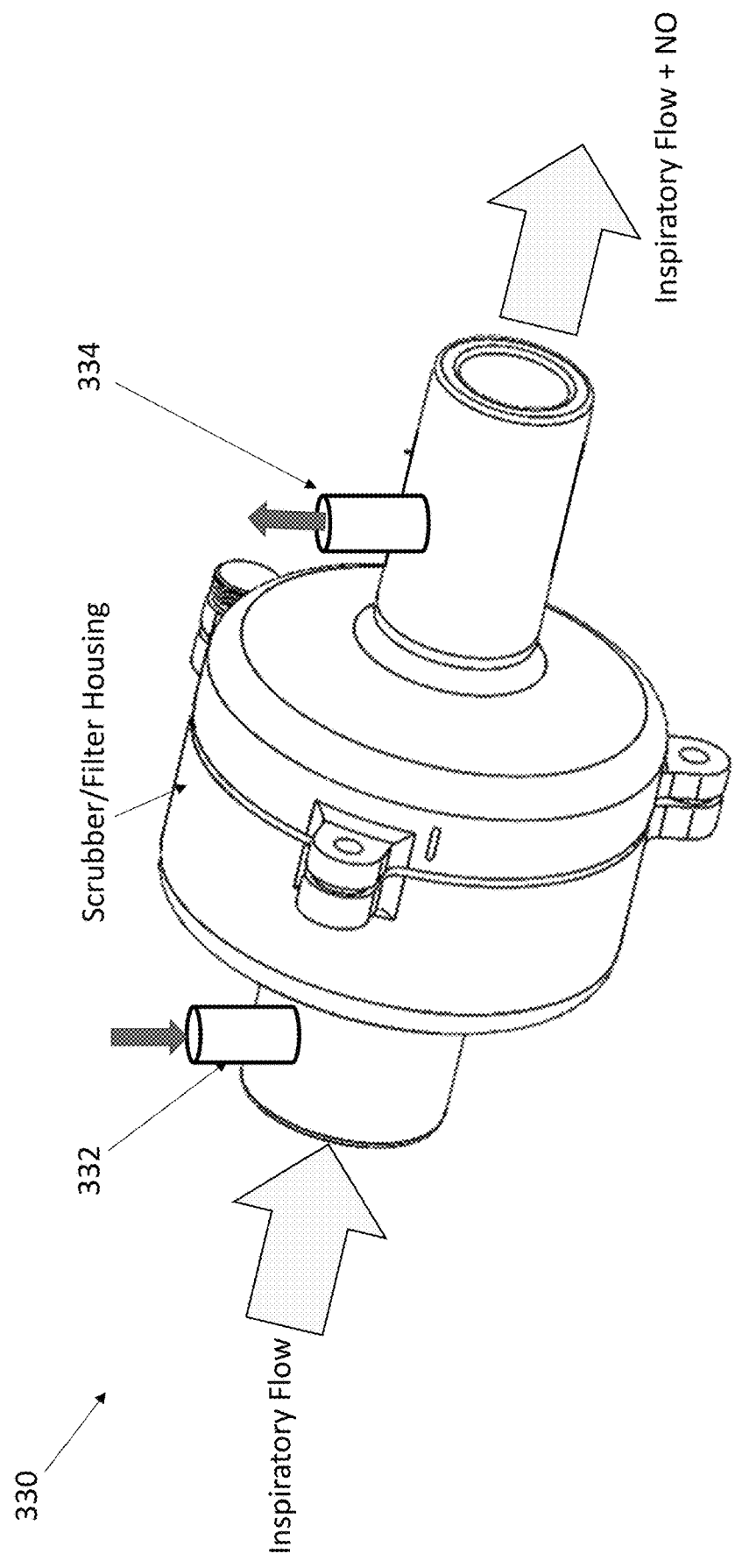
FIG. 23 depicts an exemplary inspiratory line scrubber assembly with NO injection and gas sampling.

FIG. 23 depicts an exemplary inspiratory line scrubber assembly 330 with NO injection using a NO injection port 332 and gas sampling using a gas sample port 334. NO is injected into an inspiratory stream upstream of the scrubber. The NO gas and inspiratory gases mix as they travel through the scrubber. A sample of the mixed gas is pulled from the assembly after the scrubber. In some embodiments, breath detection signals are detected through either the NO delivery or the gas sampling pneumatic paths. In some embodiments, a breath detection sensor is located in the scrubber housing with wired or wireless communication back to the NO generation device. In some embodiments, the scrubber/filter assembly includes or interfaces with an inspiratory flow sensor that communicates with the NO delivery device. In some embodiments, the inspiratory flow measurement is used for one or more of breath detection, inspiratory mass flow measurements, and an input to NO mass flow calculations. This embodiment enables delivery of NO later in the inspiratory limb than is typically done. Current delivery systems rely on mixing within the inspiratory limb tubing to blend the NO and inspiratory gases. This results in long transit time of NO and long residence time of NO with oxygen at elevated concentrations. An inspiratory limb scrubber with NO injection enables late NO injection, closer to the patient, resulting in equivalent mixing, less inhaled $NO_2$ and less NO loss to oxidation.

Electrodes

In some embodiments, a pair of electrodes are separable. One electrode can be replaced while the other electrode residing within the controller can be replaced at a different frequency, if replacement is required at all. In some embodiments, an electrode pair consists of a concentric rod and cylinder. In some embodiments, the outer electrode has a conical shape. The rod wears faster than the cylinder due to its lower surface area. In some embodiments, the rod is part of a replaceable cartridge. In some embodiments, the rod is part of a scrubber cartridge, reducing the number of use steps required to maintain electrodes. A similar approach can be achieved with the center electrode consisting of a needle, a cone or a point. The outer electrode can be in the form of a ring as well. Neither electrode has to be constrained to round shapes. For example, the outer electrode could be square in cross-section or some other polygon shape. In some embodiments, the outer electrode has splines that increase the electrical field between inner and outer electrode in discrete regions to facilitate break-down of the reactant gas.

Environmental Compensation

In some embodiments, a NO generation device includes a sensor to measure the characteristics of reactant gas. Reactant gas parameters measured include one or more of pressure, humidity, temperature, $O_2$ concentration, $N_2$ concentration, and flow rate. In some embodiments, ambient pressure, temperature and humidity are measured and used as inputs into the dose control algorithm. These gas measurements can be made before, within, and/or after the plasma chamber. In some embodiments, the controller uses reactant gas and/or ambient gas sensor measurements as an input to determine the reactant gas flow rate and/or plasma sparking characteristics.

Gas Measurement

In some embodiments, a NO device includes a built-in gas analyzer. In some embodiments, a gas analyzer is a separate and/or separable device from a NO generator. In some embodiments, the gas analyzer draws sample gas from a gas source and does one or more of the following: communicates wired or wirelessly with a NO generator, generates alarms, presents gas reading information. In some embodiments, gas measurements from the gas analyzer provide input into a closed-loop control scheme within a NO device to accurately achieve a NO dose target and/or minimize $NO_2$ levels. In some embodiments, the gas analyzer consists of a module that can be inserted in series or parallel with an inspiratory flow stream. In some embodiments, this approach eliminates the need for sample lines, water traps, filters, and the like. In some embodiments, a gas analyzer has one or more sensors for NO, $NO_2$ and $O_2$ that are in fluid communication with the gas within an inspiratory limb. This can reduce the delay of gas sensors by eliminating the transit time of sample gas from an inspiratory limb to a remote gas sensor bench. In addition, a wireless remote gas sensor bench can eliminate the potential for wires and tubes to tangle near the patient. It can also improve gas sensor accuracy because the shorter transit time results in less $NO_2$ formation.

In some embodiments, one or more sensors can be printed on a flex circuit or PCB, for example, to reduce size and weight. In some embodiments, the system can be operated with a coin cell and be disposable. In some embodiments, it wirelessly communicates to a NO generator. In some embodiments, a gas analyzer also measures a gas flow rate.

The gas analyzer can communicate with any of the devices disclosed herein, including but not limited to a NO generation device, a NO delivery device, a ventilator, a handheld device, and a cell phone or other remote device. Communication can be achieved using a variety of methods, including Bluetooth, ethernet, WiFi, etc.

Figure 24:
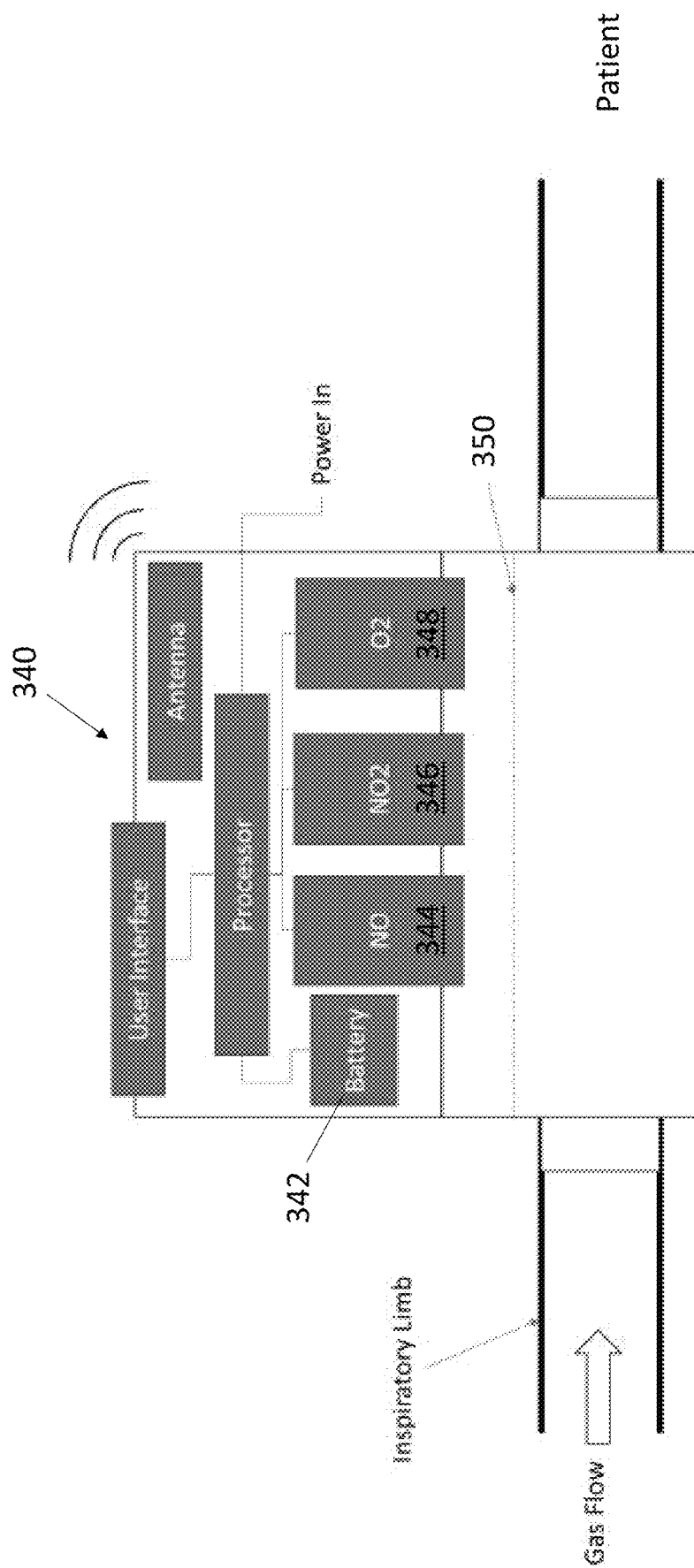
FIG. 24 illustrates an embodiment of a remote gas measurement device with a disposable gas chamber that includes a membrane to protect reusable sensors.

FIG. 24 depicts a remote gas measurement device 340. It features connectors to be integrated into an inspiratory limb. The device receives power from either an external source, internal batteries 342, or both. The embodiment shown communicates wirelessly with other treatment devices, such as a NO generator, medical gas blender, NO delivery system, patient monitor, and/or ventilator. In some embodiments, the inspiratory flow rate is also measured. A user interface can provide real time measurements of gas concentrations using a plurality of sensors 344, 346, 348. The device can enable users to set high and low alarm thresholds for each gas.

The device in FIG. 24 shows an optional membrane 350 between the gas sensors and the inspiratory gas. The membrane can protect gas sensors from direct exposure to patient exhaled gases. The membrane can also prevent liquid water from contacting the gas sensors. In some embodiments, the gas sensors are mounted above the inspiratory limb, as shown to prevent liquid water from contacting the sensors via gravity. In some embodiments, the sensor chamber is warmed to prevent water condensation on the sensors. In some embodiments, the sensor chamber is warmed to 37 deg C. In some embodiments, sensors are calibrated at the temperature that they are warmed to. In some embodiments, gas sensor outputs are temperature-compensated based on the temperature of either the gas sensor chamber, the gas sensor or both.

Continuing with FIG. 24, in some embodiments the gas sensor housing can be separated from a lower housing. The lower housing consists of input and output inspiratory flow connectors, a housing, a connector to the gas sensor module and an anti-microbial membrane. In some embodiments, the antimicrobial membrane is in the form of a fine particle filter. The lower housing is single-patient-use while the upper, gas sensor module can be used for multiple patients. In some embodiments, the lower housing is combined with another common inspiratory limb component, such as a $NO_2$ scrubber, HEPA filter, nebulizer, and/or humidifier.

The removable gas measurement device can communicate using any method, including wired (ethernet, RS232, USB, for example) or wirelessly (Wi-Fi, ZigBee, Bluetooth, Infrared, for example). Devices receiving information from the gas sensor assembly can include but are not limited to NO generation devices, NO deliver devices, ventilators, CPAP systems, hand-held monitors, patient monitors, cell phones, and PCs.

In some embodiments, the gas sensors are printed on a printed circuit board or flex circuit and powered by a coin cell, enabling a very small and lightweight gas analyzer to be constructed. In some embodiments, the gas analyzer is disposable. In some embodiments, the gas analyzer is reusable, requiring only periodic battery changes and cleaning.

Figure 25:
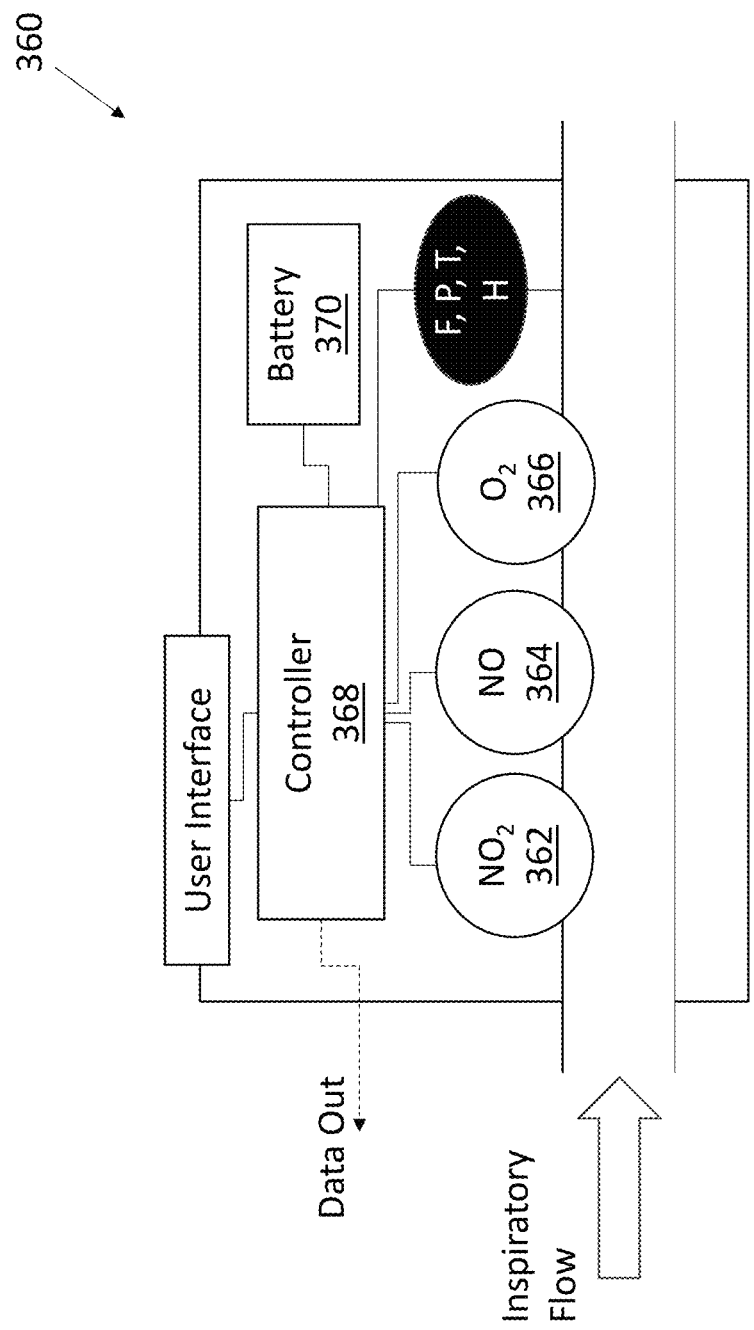
FIG. 25 illustrates an embodiment of a remote gas measurement device that measures inspiratory gases directly.

FIG. 25 illustrates an alternative embodiment of a compact gas analyzer 360. Inspiratory flow enters the system and passes by one or more gas sensors. In some embodiments, $NO_2$, NO and $O_2$ sensors 362, 364, 366 are utilized. In some embodiments, more than one sensor is used for a particular gas for reliability and safety purposes. In some embodiments, redundant gas sensors of different types can be used to prevent common mode failures. For example, photoluminescent, electrochemical, IR spectroscopy, or photoionization detectors can be included. The embodiment in FIG. 25 measures one or more of flow rate, pressure, temperature and humidity for compensation of the measured gas concentrations.

The device in FIG. 25 includes a controller 368 that collects gas concentration data from the gas sensors and reports information to a user interface. A battery 370 powers the system. In some embodiments, the battery is rechargeable. Data exits the system through a wired connection to a NO generator, ventilator, patient monitor or other piece of medical equipment.

In addition to collecting gas concentration data from the gas sensors, the controller can also monitor the health of the sensors, tracking sensor drift and calibration settings. In some embodiments, the controller can step a user through a sensor calibration process whereby the user subjects the sensors to controlled levels of specific gases. Sensor output for each gas concentration is used to generate calibration settings for the sensor. In some embodiments, a gas sensor includes a memory device (e.g. EPROM) that includes information such as the date of manufacture, expiration date, calibration coefficients, sensor battery level, sensor part number, sensor version number, sensor range, and other information.

Figure 26:
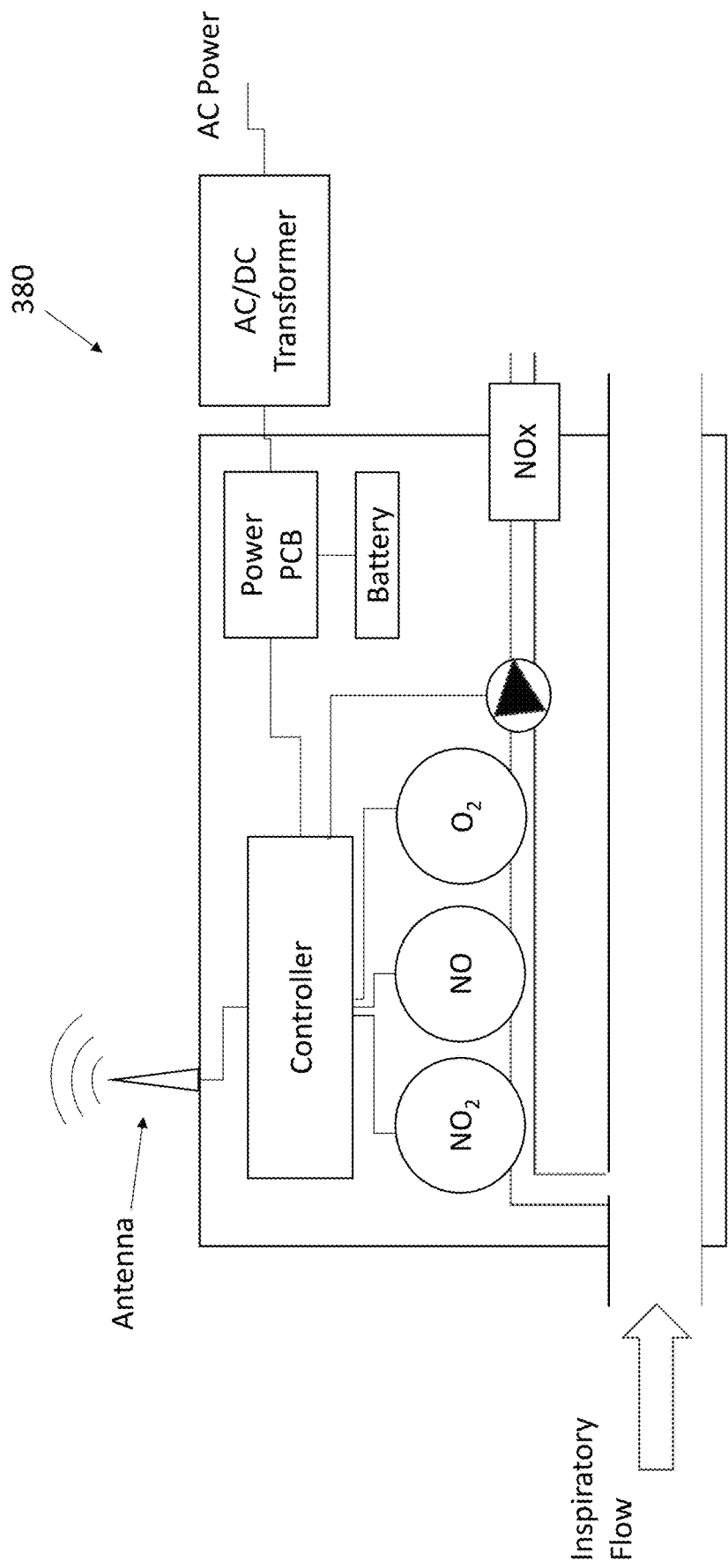
FIG. 26 illustrates an embodiment of a remote gas measurement device that measures inspiratory gases in a sidestream.

FIG. 26 illustrates an alternative remote gas analyzer 380 featuring a side-stream gas analysis path. This approach can allow control of the flow rate of gas flowing past the gas sensors. In the embodiment shown, sampled gas passes through a NOx scrubber prior to release into the ambient environment. In some embodiments, sampled gas is merged back into the inspiratory flow after analysis. In some embodiments (not shown), the analyzer also measures one or more of the following parameters: temperature, humidity, flow rate and pressure of the inspiratory gas flow. In the depicted embodiment, the controller communicates wirelessly with external devices. External devices can include one or more of the following: hospital data system, ventilator, CPAP machine, patient analyzer, NO generation device, NO delivery device, anesthesia machine, inhaler, manual resuscitator and others. The NO analyzer can communicate information including but not limited to gas concentrations, alarm conditions, battery life, temperature, humidity, pressure, and inspiratory flow rate.

The side stream of sample gas is typically a low flow rate (e.g. 100-1000 ml/min). In some treatments, the sampled gas is humidified (e.g. 100% RH at 37 deg C.). In the case of humidified sample gas, some embodiments have one or more of a water trap, humidity exchange tubing, or other means to remove water from the sample before exposing the gas sensors. In some embodiments, the gas sensor chamber is insulated to minimize heat loss around the inspiratory flow tube and prevent condensation. In some embodiments, the gas sensor chamber is actively warmed to 37 deg C. or higher to prevent condensation within the gas sensor pneumatic pathway. In the embodiment depicted in FIG. 26, the pump is located after the gas sensors. This exposes the sensors to a lower pressure than in the inspiratory limb. In some embodiments, a restrictive orifice can be utilized before the gas sensors to further reduce the pressure within the region of the sensors. A reduction in pressure decreases the relative humidity and potential for condensation in the region of the sensors.

Prolonged and/or high dose NO therapy can result in elevated methemoglobin levels. In some embodiments, a NO generation and/or delivery device either includes a methemoglobin measurement capability or communicates with a methemoglobin analyzer. In some embodiments, a NO generation and/or delivery device will not permit NO therapy to begin until a methemoglobin measurement is received. In some embodiments, the NO generation and/or delivery device either stops treatment or lowers the dose in the presence of elevated methemoglobin levels. In some embodiments, a NO generation and/or delivery device cannot start treatment if methemoglobin levels are already high. In some embodiments, a NO generation and/or delivery device can resume treatment automatically when methemoglobin levels return to a particular level.

In some embodiments, a NO generation device limits the amount of NO that can be delivered over a period of time. In some embodiments, a NO generation device permits NO dosing of a specific number of breaths per unit time. For example, 3 breaths every minute, or 20 breaths in an hour. The actual NO dose limitation can be based on one or more of the desired NO dose in mg/hr, the patient size, the patient's lung volume, the patient condition (type of infection for example), measured methemoglobin levels, or $SpO_2$ levels.

The electrodes can be formed from a variety of pure materials, including alloys of hafnium, iridium, tungsten, silver, ruthenium, stainless steel, and platinum. For example, an alloy of iridium-tungsten, platinum-iridium, hafnium iridium, tungsten iridium, tungsten silver can be used.

Figure 27:
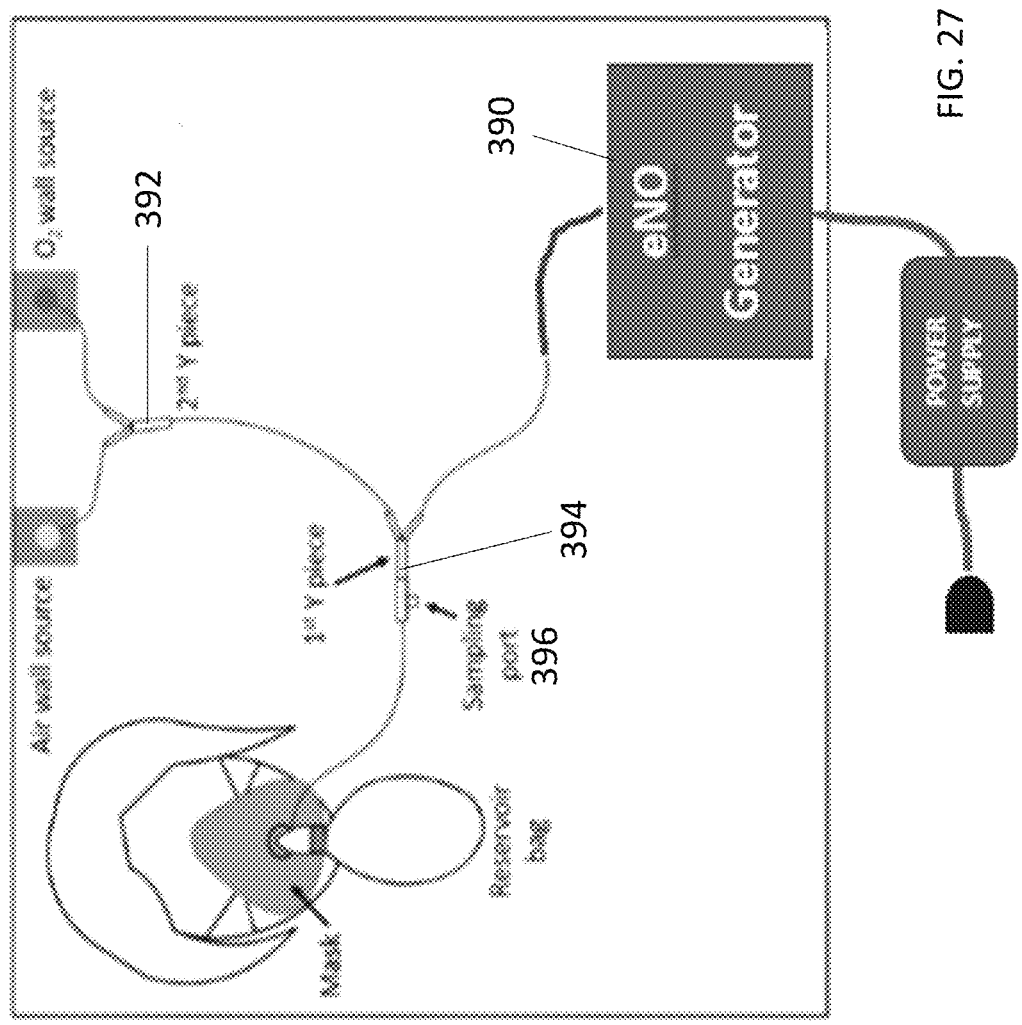
FIG. 27 illustrates an application of NO to a mask with reservoir application.

FIG. 27 depicts an embodiment of a NO delivery system. Oxygen and medical air are sourced from an external supply and provided at target pressure and flow rates. In some embodiments, the air and oxygen pass through a gas blender (not shown). Oxygen and air merge, for example in a Y fitting 392, and travel toward the patient. NO from a NO generation device 390 merges with the air and oxygen flow, for example in a Y fitting 394. A sampling port 396 is located downstream of the NO injection location. In some embodiments, mixing elements are used (not shown) between the injection location and sampling location to ensure that the gas sample is well-mixed prior to sampling. In some embodiments, the sampling location is further downstream from the NO injection location to ensure complete mixing.

In some embodiments, all gas flow rates are constant. This simplifies the task of generating and delivering an accurate amount of NO.

NO/air/$O_2$ gas passes to a patient wearing a non-rebreather mask. The reservoir (bag) connected to the inspiratory line fills between breaths at a slow and constant rate. The patient inhales gas from the reservoir, thereby emptying the reservoir. The gas flow rate filling the reservoir is targeted to match the patient inspiratory minute volume so that the reservoir doesn't fully collapse during inhalation or gradually increase in volume and/or pressure.

Figure 28:
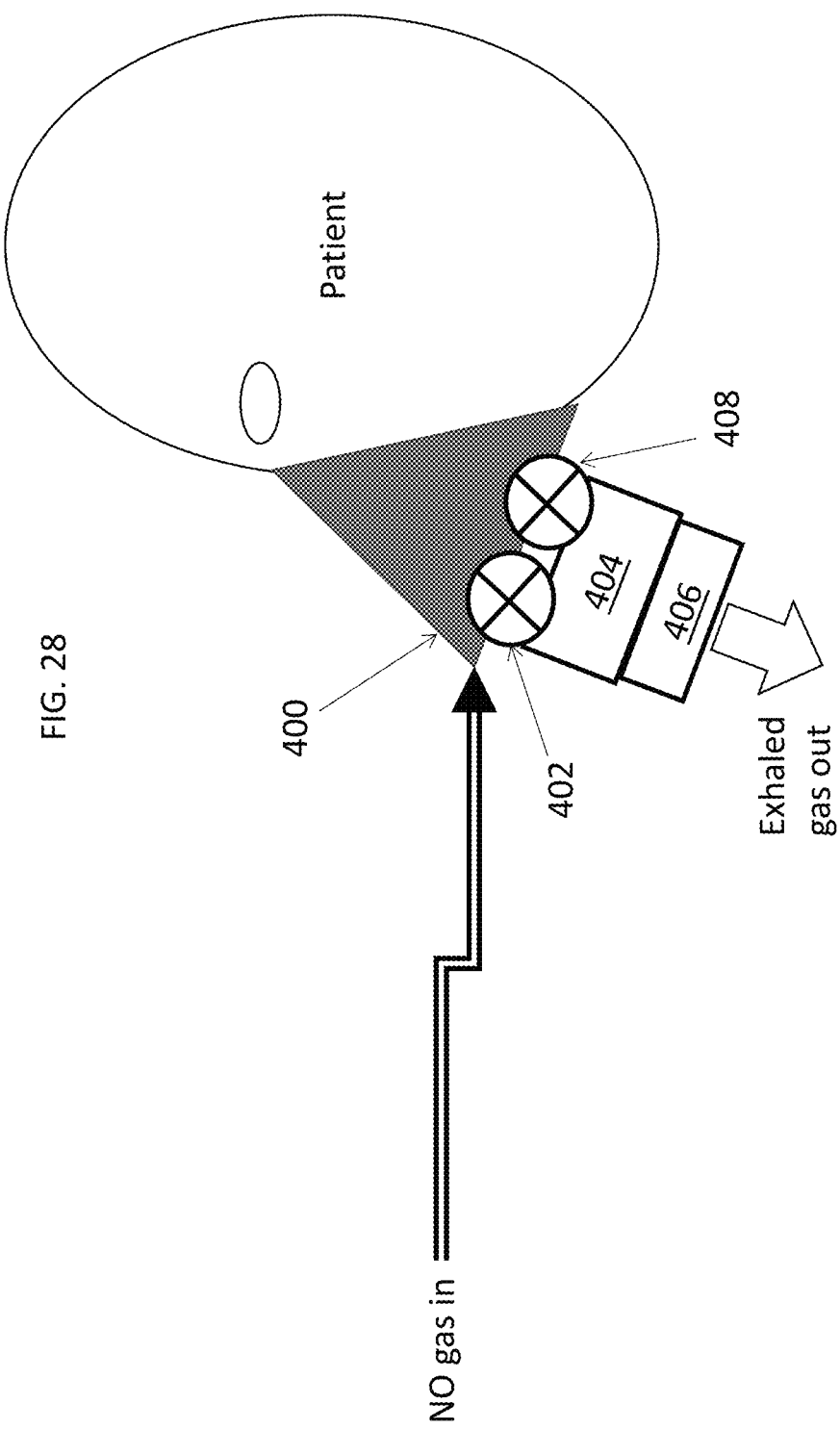
FIG. 28 illustrates a patient mask with filter and scrubber for exhaled gas.

FIG. 28 depicts an exemplary embodiment of a mask 400 for use with inhaled NO therapy. NO-containing gas enters the mask through a line. A rebreather volume (not shown) is optionally used to accumulate NO between breaths as described above. The patient inhales gas from the mask and NO line. When the patient exhales, gas exits through a 1-way valve 402, a scrubber 404, and a filter 406. In some embodiments, the valve is after the scrubber and filter. A pressure relief valve 408 exhausts gas through the scrubber and filter as well. In some embodiments, exhaled gases are vented through a valve in the mask. In some embodiments, exhaled gases exit through the seal between the patient mask and the patient face, however this prevents exhaled gases from being scrubbed and filtered. In some embodiments, exhaled gases exit the system through a valve in the tubing prior to the mask. In some embodiments, exhaled gases are scrubbed for $NO_2$ and/or NO and/or $CO_2$ prior to release. In some embodiments, excessive pressure, as can occur when a reservoir completely fills, is vented to atmosphere with or without scrubbing. In some embodiments, an alarm is generated when a pressure-relief valve is activated. In some embodiments, a pressure relief valve makes an audible sound as gas passes through it (like a whistle or a vibration) to inform the user of a mismatch between patient inspiration and gas supply.

It will be understood that the systems and methods disclosed herein can be used in a variety of clinical applications and infectious indications, including but not limited to:

Cystic Fibrosis (Adult and pediatric)
    Acute infectious exacerbation
    Chronic infection
Infectious Bronchiolitis
    Pediatric related to RSV and other viruses
    Adult bronchiolitis
COPD
    Acute exacerbations including pneumonia
    Chronic Bronchitis
Post Lung Transplant
    acute lung infections
    chronic lung infections
Bronchiectasis
    Acute infectious exacerbations
    Chronic infection
Nontuberculous mycobacterial infection
    Chronic infection
MDR tuberculosis
    Chronic infection
Pneumonia (agnostic to microbe)
    Hospitalized non-ventilated
    Hospitalized ventilated
    Ex-hospital treatment of community acquired pneumonia
    Home ventilation-associated Pneumonia
Asthma
    Acute viral exacerbations
Immune deficiencies, e.g. CVID, post-chemotherapy etc.
    Acute lung infections (for example, bacterial)

EXAMPLES

Exemplary instructions for use of the devices described herein are provided.

Device Description eNOX-200 Nitric Oxide generation system is a portable investigational device that electrically generates Nitric Oxide (eNO) from ambient air using a plasma-based approach and delivers NO concentrations between 100-200 ppm to the patient. The device enables users to customize NO delivery to meet the respiratory needs of a spontaneously breathing patient by automatically accommodating variable inspiratory flow rates or by manually entering expected inspiratory flow rates.

Intended Use

The intended use of the eNOX-200 device is for investigational use only to support IRB-approved clinical trials under an investigational device exemption (IDE) to potentially prevent progression of COVID-19 in spontaneously breathing patients with mild to moderate symptoms and to potentially prevent SARS-Cov-2 infection in healthcare workers. The use specifications (i.e. intended users, use environment, and patient population) are determined by IRB-approved clinical trial protocols.

Theory of Operation

Figure 29:
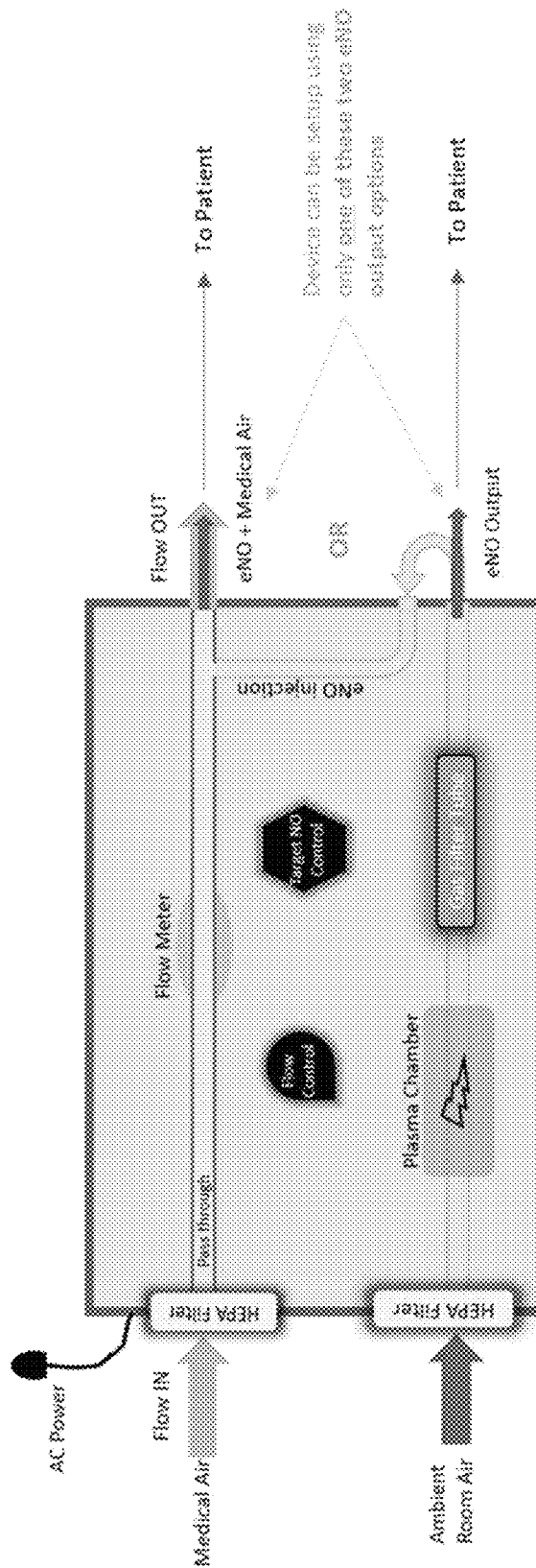
FIG. 29 is an exemplary diagram of a NO generation system.

The eNOX-200 injects a fixed 2.8 L/min flow of electrically produced NO (eNO) into the patient breathing circuit. The flow inspired by the patient is total of eNO flow, medical air flow, and supplemental oxygen flow. The concentration of eNO produced and delivered varies based on the NO concentration target level set by the user and the inspiratory flow of medical air and/or supplemental oxygen delivered to the patient. The schematic diagram of the system is shown in FIG. 29.

The eNOX-200 generates medical grade NO for inhalation from ambient air. A HEPA filter at the ambient room air intake into the eNOX-200 removes unwanted particles and prevents contamination from the room air which then is pumped into the plasma chamber that combines nitrogen and oxygen by plasma technology. A Gas Filter Tube containing soda lime then purifies NO by removing contaminants and nitrogen dioxide (NO2). The resulting gas output is electrically produced NO (eNO), which is a mixture of air and NO. The Gas Filter Tube is a multipatient consumable component which must be changed after 16 hours of unpacking whether it was in use or not within the 16 hours.

The system has two eNO flow output route options for connection to patient breathing circuit: (1) Flow OUT–The eNO gas is injected into the pass-through inspiratory flow channel to mix with medical air to output eNO+medical air into patient breathing circuit, and (2) eNO output–The eNO gas from eNOX-200 can be directly injected into the patient breathing tube.

Figure 30:
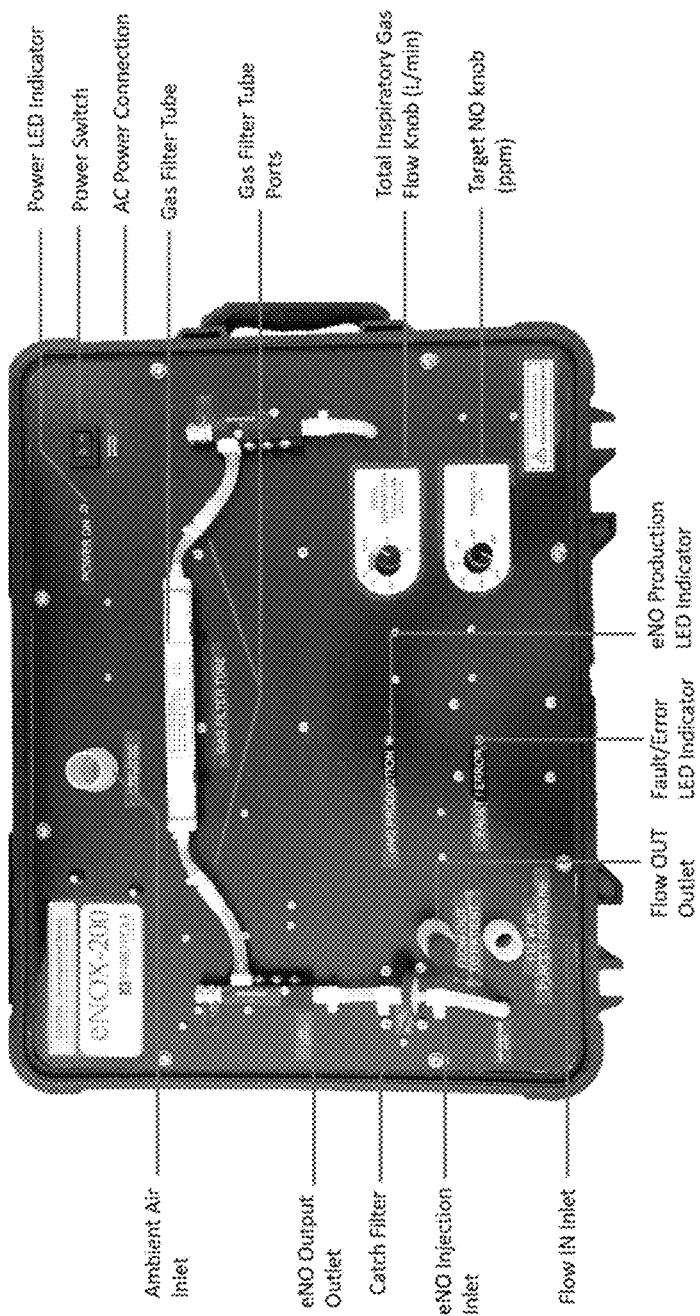
FIG. 30 is an exemplary embodiment of an eNO device showing controls, connectors, and indicators.

FIG. 30 is an exemplary view of an eNO device showing controls, connectors, and indicators. For example, when the Target NO knob is at position OFF, the plasma is not activated, and the system is not creating eNO. The device continues to output at 2.8 L/min air flow without NO. Target concentrations of NO between 100 and 200 ppm are only compatible with total inspiratory flow between 2 and 20 L/min. For total inspiratory flow above 20 L/min the delivered NO concentration to the patient will be lower than the selected Target NO concentration.

TABLE 1

Exemplary controls and connections
CONTROLS

| | |
|---|---|
| Power Switch | Turns the device on and off |
| Target NO (ppm) | Sets the device to deliver desired NO concentration i.e. desired concentration of NO after eNO is diluted and mixed in inspiratory flow. |
| | OFF - The device is not producing Nitric Oxide |
| | 100, 120, 140, 160, 180, 200 - Discrete values of Target NO concentrations in ppm available for selection. |
| Flow (L/min) | Sets the device to automatically measure the set total inspiratory flow rate (AUTO mode) or enables user to manually enter the set total inspiratory flow rate (Manual mode) |
| | Set Inspiratory Flow Rate = Flow rate of pressurized air + Supplemental Oxygen |
| | AUTO - The set flow rate is automatically detected by the device |
| | 2 to 20- The set flow rate values between 2 L/min and 20 L/min. |
| | Visual Indications |
| Power ON | Indicates the power is ON when lit green |
| eNO production | Indicates device is producing eNO when lit blue |
| Fault/Error | Indicates a system fault or a use error is detected when lit red |
| | Blinking - The fault or use error is recoverable by user action |
| | Solid - The fault is unrecoverable |
| | Audio Indications |
| Short beep | Indicates that the device has turned ON. |
| Continuous beeps | Indicates that the device has detected a recoverable fault or user error |
| Continuous tone | Indicates that the device has detected an unrecoverable fault |
| | Connections |
| Ambient Air Filter Port | HEPA filter connection to ensure filtered ambient air is used to produce eNO |
| Gas Filter Tube Ports | Gas Filter Tube connections |
| Flow IN | HEPA Filtered Medical air source connection i.e. Flow IN to the device |
| Flow OUT | Patient breathing circuit connection i.e. flow OUT of the device, to the patient; includes air + eNO |
| eNO Output | eNO (NO + Air) output to be connected either to injection port or to patient breathing circuit. |

The system has two basic modes of operation. In AUTO MODE, the user selects the NO target level and passes the medical air through (Flow IN) inspiratory air flow channel of the device. The system measures the inspiratory air flow and automatically determines the required concentration of eNO to inject into the inspiratory air flow in order to reach the selected target levels of NO concentrations after dilution of eNO into inspiratory air flow. In MANUAL MODE, the user selects the NO target level AND manually selects the flow rate of the inspiratory flow air, which could include either or both medical air flow and supplemental oxygen air flow. The system determines the required concentration of eNO to inject into the inspiratory air flow in order to reach the selected target levels of NO concentrations after dilution of eNO into inspiratory air flow. The system also incorporates additional safety features such as pressure relief valves, and flow sensors, as well as internal software self-monitoring checks to ensure that operational issues are monitored and managed.

System Setup

User may customize and update the patient breathing assembly setup in accordance with an IRB-approved clinical trial protocol. The following are potential configurations for device connection to a patient breathing assembly and/or Non-invasive ventilation. The intent of the figures and text in this section is to demonstrate the type of connections that can be made to and from the eNOX-200 device in different modes of operation. The patient breathing assembly set up shown in the figures below is for reference only.

Figure 31:
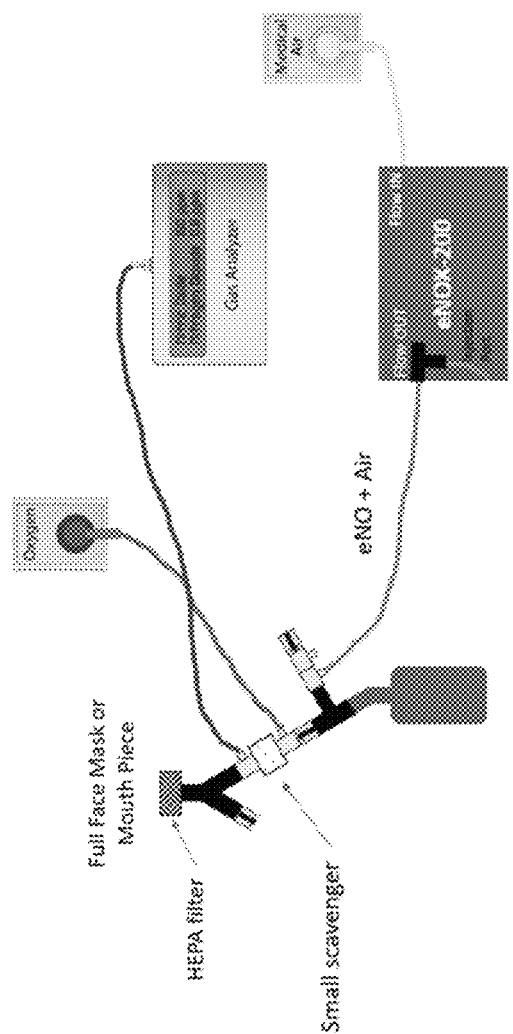
FIG. 31 is an exemplary embodiment of a patient breathing circuit.
Figure 32:
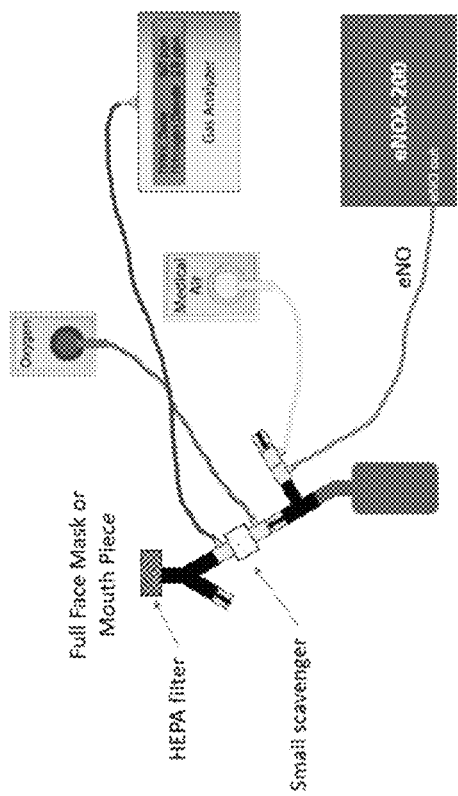
FIG. 32 is an exemplary embodiment of a patient breathing circuit.

If the patient requires supplemental oxygen, connect the supplemental oxygen directly to the patient breathing circuit close the patient face mask, as shown in FIG. 31 (Manual Mode Setup Option A—Medical Air PASSES THROUGH the eNOX-200) and FIG. 32.

The device can be set up to inject eNO into the medical air prior to patient breathing circuit connections, or directly into patient breathing circuit. To inject eNO into the medical air prior to patient breathing circuit, the medical air is passed through the eNOX-200. To inject the eNO directly into the patient breathing circuit, medical air bypasses the eNOX-200. If you are passing medical air through the eNOX-200, set up the system as shown in FIG. 31.

If you are bypassing the eNOX-200 to deliver medical air, set up the system as shown in FIG. 32. Disconnect the eNO Output tubing at the catch filter connection, closer to the eNO injector inlet. Connect the patient breathing circuit to the catch filter luer connection using tubing and adapters as needed. Connect the medical air flow directly to the patient breathing circuit.

Figure 33:
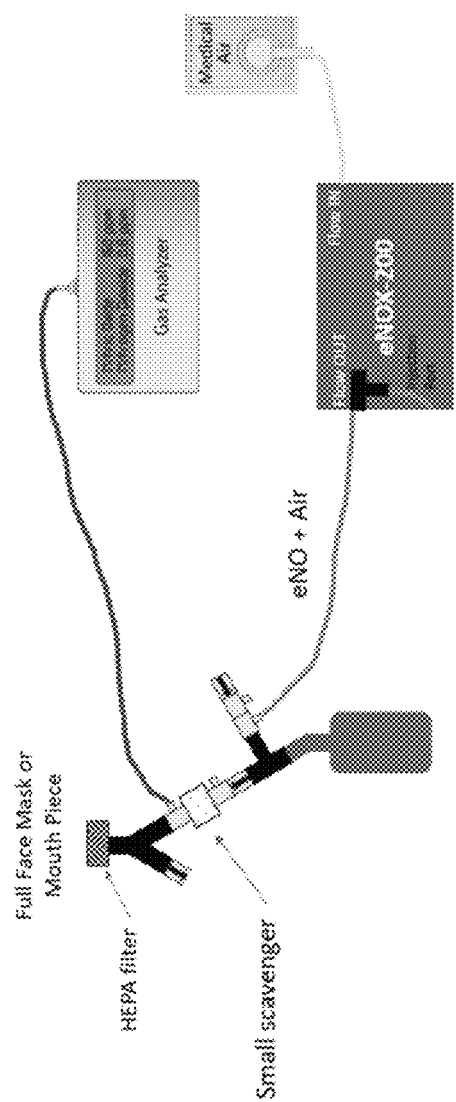
FIG. 33 is an exemplary embodiment of a patient breathing circuit.

If the patient does not require supplemental oxygen, it is recommended to set up the system to pass medical air through the eNOX-200, as shown in FIG. 33. To enable AUTO mode: Connect the inspiratory air flow to the "Flow IN" 22 mm connection, using adapters if needed. Connect the patient breathing assembly to the "Flow OUT" 22 mm connection using 22 mm diameter tube. Confirm that the eNO output tube is connected to injection port.

Delivering NO

An exemplary method for delivering NO includes:
1. Connect the eNOX-200 device to a hospital-grade power source using the power cable provided with the system.
2. Ensure the system is set up and connected to the patient breathing assembly per desired configuration; see System Set Up for examples.
   a. It is recommended to connect 90° connectors to the Flow IN and Flow OUT connections.
   b. Connect a HEPA filter at the Flow IN inlet port.
3. Confirm that the Target NO Knob is turned OFF.
4. Insert a new Gas Filter Tube. If a tube is already inserted, check the "Change by Date" and "Change by Time" fields on the Gas Filter Tube label; see NO Delivery Management for gas filter tube replacement criteria.
   a. Connect, in no specific orientation, the two ends of the gas filter tube to each of the Gas filter luers' connections on the top of the eNOX-200 device.
   b. Secure the gas filter tube in place using the clips on the top of the eNOX-200 device.
5. Connect a HEPA filter at the ambient air filter port.
6. Turn the device ON using the Power Switch. Confirm that device beeps once and eNO LED indicator and Fault/Error LED indicator are lit for 1 second.
7. Confirm that the Power ON LED indicator remains lit green.
8. Connect the patient breathing assembly to the patient and check the system connections are tight and secure. Adjust the circuit parts as needed.
9. Turn the Total Inspiratory Gas Flow knob to one of the following desired mode:
   AUTO Mode—If the patient is not receiving supplemental oxygen and Medical Air passes through the device, select "Auto".
   Manual Mode—If the patient is receiving supplemental oxygen or Medical Air is bypassing the device, manually calculate the total inspiratory flow i.e. supplement oxygen flow rate+Medical Air flow rate and set the Total Inspiratory Gas Flow knob to the calculated value.
10. Turn the Target NO knob to a desired dose. Confirm "eNO Production" LED indicator lights in blue.
11. Confirm that the desired dose of NO is measured by the Gas Analyzer.
12. Confirm that $NO_2$ levels measured by the Gas Analyzer are lower than 2 ppm in absence of supplemental oxygen. Refer to IRB-approved clinical trial protocols for safe limits of $NO_2$ when supplemental oxygen is delivered to the patient.
13. Upon completing a session:
   a. Turn the Target NO Knob to OFF and wait for 30 seconds to allow the device to purge NO out of the internal tubing.
   b. Turn the device OFF using the Power Switch.
   c. Confirm "POWER ON" LED indicator is OFF.
14. Remove and dispose the gas filter tube per hospital's non-hazardous waste disposal policy.

NO Delivery Management

An exemplary method for managing NO delivery includes:
1. After each patient use, replace the HEPA filter at the ambient air filter port and Flow IN port.
2. Replace the multi-patient Gas Filter Tube after 16 hours of unpacking whether it was in use or not within the 16 hours.
   a. Before connecting to the device, ensure the Gas Filter Tube has not passed the expiration date listed on the label affixed on the Gas Filter Tube or the packaging.
   b. Record the date and time the Gas Filter Tube would need replacement in the "Change by" date and time fields available on the label affixed on Gas Filter Tube.
3. Before starting a NO delivery session, confirm the "Change by" date and time fields to ensure the Gas Filter Tube will not need to be replaced during the session.

Alarms and Troubleshooting

TABLE 2

| Troubleshooting | | |
| --- | --- | --- |
| Condition | Possible Cause | Recommended Action |
| Device does not turn ON. | There is no power. | Connect the device to AC power |
| Power ON LED indicator is not lit green. | Target NO knob is set to OFF. | Change the Target NO knob to desired ppm level if NO delivery is intended. |
| eNO Production LED indicator is blinking blue. | The eNO produced is too low for the patient breathing setup including inspired flow rate, sampling, and leaks | If the Total Inspiratory Gas Flow knob is set to Auto, switch to manual mode by selecting the inspiratory flow values on the knob until desired NO levels are reached.<br>If in manual mode, adjust and fine tune the flow selection on knob to a higher value until desired NO ppm is measured on the monitoring assembly. |

TABLE 2-continued

Troubleshooting

| Condition | Possible Cause | Recommended Action |
|---|---|---|
| | | If the measured NO value remains to be lower by 20% or more than desired value, change the target NO to one setting higher. If the problem persists, take the device out of service when possible and contact a Third Pole representative. |
| NO measurement on gas analyzer is reading value higher than set target NO | The eNO produced is too high for the patient breathing setup including inspired flow rate, sampling, and leaks | If the Total Inspiratory Gas Flow knob is set to Auto, manually select the inspiratory flow values until desired NO levels are reached. If in Manual mode, adjust and fine tune the flow to a lower value until desired NO ppm is measured on the monitoring assembly. If the measured NO value remains to be higher by 20% or more than desired value, change the target NO to one setting lower. If the problem persists, take the device out of service when possible and contact a Third Pole representative |
| NO measurement on gas analyzer is reading zero value when eNO Production LED indicator is lit blue. | eNO is produced but not injected into patient breathing circuit. | Check that Gas Filter Tube is connected properly. Check that eNO output tubing is plumbed correctly. Check that all the tubing connections are connected properly with no leaks. If any of the tubing need replacement, please remove the device immediately from service and contact a Third Pole representative. |
| NO2 measurement on gas analyzer is reading value higher than the safety limits and NO measurement on gas analyzer is reading expected value. | The NO2 produced is too high in the patient breathing setup | Purge the bag reservoir used in the patient breathing circuit. Replace the scrubbing material used in patient breathing circuit. Check "Change By" date and time on the Gas Filter Tube label and replace it if needed. If the problem persists, take the device out of service when possible and contact a Third Pole representative. |
| Fault/Error LED indicator is blinking red with continuous audible beeps | Device is not detecting a flow when Total Inspiratory Gas Flow is set to Auto. | Check that Air ambient filter is not occluded. Ensure that medical air flow is ON. Check for disconnection, kinks or occlusion in medical air connection to Flow IN inlet and correct accordingly |
| | Device is detecting back pressure | Ensure a 22 mm diameter tube is used to connected patient breathing circuit to Flow OUT. Check for kinks or occlusion in patient breathing circuit and correct accordingly. If problem persists, check for kinks or occlusion between eNO output and eNO Injector Inlet including Catch Filter and if tubing or filter needs replacement, please remove the device from service immediately and contact a Third Pole representative. |
| Fault/Error LED indicator is lit solid red with continuous audible tone | A critical device failure has been detected. Device is unable to operate, produce NO, or deliver NO. | Turn the device OFF, remove and reconnect AC Power, and turn the device ON. If the problem persists, please remove the device from service immediately and contact a Third Pole representative. |
| Pressure relief valves (PRV1 and PRV2) are making hissing sound | Device is detecting back pressure | Check for kinks or occlusion in patient breathing circuit and correct accordingly. If problem persists, check for kinks or occlusion between eNO output and eNO Injector Inlet including Catch Filter and if tubing or filter needs replacement, please remove the device from service immediately and contact Third Pole representative |

TABLE 2-continued

Troubleshooting

| Condition | Possible Cause | Recommended Action |
|---|---|---|
| White particulates visible in the tube between eNO output and catch filter | Gas Filter Tube malfunction | Replace Gas Filter Tube if white particulates are found during NO delivery sessions. Please remove the device from service when possible and contact Third Pole representative. |

Maintenance

Maintenance of the system can include:

1. The device must be cleaned between patient uses.
2. Clean all exterior surfaces of the device with a soft cloth or a wipe dampened in isopropyl alcohol (70%) or a standard hospital disinfectant solution.
3. Disinfect the device following your institution's guidelines.
4. The device and its components and accessories do not require sterilization.

Technical Specifications

The following is a listing of exemplary technical specifications for the system in the example.

TABLE 3

Physical Characteristics

| Dimensions | 23"H × 19"W × 12"D |
|---|---|
| Weight | 23 lbs |

TABLE 4

System Requirements

| Input Voltage | Global AC power mains at 90-264 V AC @ 50/60 Hz |
|---|---|
| Input Power | 120 VA max |
| Temperature | Operating: 5 to 40° C. |
| Humidity | 15 to 95% RH non-condensing |
| Input Fuse | 4 amps |

TABLE 5

NO Delivery

| NO Target Range | 100-200 ppm |
|---|---|
| eNO Dose Flow | 2.8 L/min fixed flow |
| eNO Dose Accuracy | ±20% of set Target NO ppm |
| eNO Dose Delivery Typical Response Time | 30 seconds |
| Auto mode air flow compatibility | 2-20 L/min |
| Manual mode air flow compatibility | 2-20 L/min |

TABLE 6

Gas Filter Tube

| Use Life | 16 hours after unpacking (whether in use or not) |
|---|---|
| Type | Disposable |

TABLE 7

Device Connections

| Ambient Air Filter Port | 22 mm (to connect HEPA Filter) |
|---|---|
| Flow IN | 22 mm |
| Flow OUT | 22 mm |
| eNO Output | 4.5 mm |

All patents, patent applications, and published references cited herein are hereby incorporated by reference in their entirety. It will be appreciated that several of the above-disclosed and other features and functions, or alternatives thereof, may be desirably combined into many other different systems or application. Various alternatives, modifications, variations, or improvements therein may be subsequently made by those skilled in the art.

What is claimed is:

1. A system for providing nitric oxide, comprising:
at least one plasma chamber configured to ionize a reactant gas to generate a product gas containing nitric oxide;
at least one controller configured to regulate an amount of nitric oxide in the product gas generated in the at least one plasma chamber using one or more parameters as an input to the controller;
one or more sensors configured to collect information relating to at least one of patient information, the reactant gas, the product gas, and an inspiratory gas into which at least a portion of the product gas flows, the sensors configured to communicate the information to the controller to be used as the one or more parameters, at least one of the one or more sensors being configured to collect patient information relating to a methemoglobin measurement; and
an injection pump in communication with the controller, the controller configured to control a delivery of methylene blue from the injection pump based on the methemoglobin measurement and the amount of NO delivered to the inspiratory gas to decrease a methemoglobin level.

2. The system of claim 1, wherein the methemoglobin measurement from the methemoglobin sensor is used by the controller to generate an amount of the product gas based on at least one of a threshold methemoglobin level and a rate of change of the methemoglobin measurement.

3. The system of claim 2, wherein the methemoglobin threshold level is maintained by the controller for a predetermined time.

4. The system of claim 2, wherein the methemoglobin measurement from the methemoglobin sensor is monitored by the controller such that the methemoglobin measurement is maintained at less than the threshold methemoglobin level until a predetermined mass of NO has been delivered to the inspiratory gas.

5. The system of claim 1, wherein the methemoglobin measurement from the methemoglobin sensor is used by the controller to deliver an amount of the product gas based on at least one of a threshold methemoglobin measurement and a rate of change of the methemoglobin measurement.

6. The system of claim 5, wherein a methemoglobin threshold level is maintained by the controller for a predetermined time.

7. The system of claim 5, wherein the methemoglobin measurement from the methemoglobin sensor is monitored by the controller such that the methemoglobin measurement is maintained at less than a threshold methemoglobin level until a predetermined mass of NO has been delivered to the inspiratory gas.

8. The system of claim 1, wherein the methemoglobin sensor is integrated into the system.

9. The system of claim 1, wherein the controller is configured to dynamically change a NO dose using the methemoglobin measurement from the methemoglobin sensor to keep the methemoglobin measurement below a threshold while maximizing quantity of NO delivered.

10. The system of claim 1, wherein the controller is configured to require an initial measurement from the methemoglobin sensor before NO delivery begins.

11. The system of claim 1, wherein the controller is configured to suspend NO generation based on the information from the methemoglobin sensor.

12. The system of claim 11, wherein the controller is configured to resume NO generation when the methemoglobin measurement from the methemoglobin sensor decreases to a threshold level.

13. The system of claim 1, wherein the controller is configured to vary a mass of NO delivered within each breath of the inspiratory gas from zero to a predetermined maximum value to deliver a target mass of NO per unit time.

14. The system of claim 1, wherein a concentration of NO in the product gas is at least 150 ppm.

15. A system for providing nitric oxide, comprising:
at least one plasma chamber configured to ionize a reactant gas to generate a product gas containing nitric oxide;
at least one controller configured to regulate an amount of nitric oxide in the product gas generated in the at least one plasma chamber using one or more parameters as an input to the controller;
at least one sensor configured to detect a methemoglobin measurement in a patient to which at least a portion of the product gas is delivered; and
an injection pump configured to deliver methylene blue to the patient and in communication with the controller, the controller configured to control a delivery of the methylene blue from the injection pump based on the methemoglobin measurement and the amount of NO delivered to inspiratory gas to decrease a methemoglobin level.

16. The system of claim 15, wherein the methemoglobin measurement from the at least one sensor is used by the controller to generate an amount of the product gas based on at least one of a threshold methemoglobin level and a rate of change of the methemoglobin measurement.

17. The system of claim 15, wherein the methemoglobin measurement from the methemoglobin sensor is used by the controller to deliver an amount of the product gas based on at least one of a threshold methemoglobin measurement and a rate of change of the methemoglobin measurement.

18. The system of claim 15, wherein the controller is configured to suspend NO generation based on information from the methemoglobin sensor.

19. The system of claim 18, wherein the controller is configured to resume NO generation when the methemoglobin measurement from the methemoglobin sensor decreases to a threshold level.

\* \* \* \* \*